(12) United States Patent
Durst et al.

(10) Patent No.: US 11,208,393 B2
(45) Date of Patent: Dec. 28, 2021

(54) METHODS FOR EXTRACTION, PROCESSING, AND PURIFICATION OF A SELECTED FAMILY OF TARGET COMPOUNDS FROM CANNABIS

(71) Applicant: Nectar Health Sciences Inc., Victoria (CA)

(72) Inventors: Tony Durst, Ottawa (CA); Jay Van Der Vlugt, Victoria (CA); Amanda Saikaley, Ottawa (CA)

(73) Assignee: Nectar Health Sciences Inc., Victoria (CA)

( * ) Notice: Subject to any disclaimer, the term of this patent is extended or adjusted under 35 U.S.C. 154(b) by 0 days.

(21) Appl. No.: 17/285,443

(22) PCT Filed: Jun. 12, 2020

(86) PCT No.: PCT/CA2020/050825
§ 371 (c)(1),
(2) Date: Apr. 14, 2021

(87) PCT Pub. No.: WO2020/248077
PCT Pub. Date: Dec. 17, 2020

(65) Prior Publication Data
US 2021/0309629 A1    Oct. 7, 2021

Related U.S. Application Data

(60) Provisional application No. 62/891,013, filed on Aug. 23, 2019, provisional application No. 62/860,382, filed on Jun. 12, 2019.

(51) Int. Cl.

| | | |
|---|---|---|
| *C07D 311/80* | (2006.01) | |
| *C07C 215/40* | (2006.01) | |
| *C07D 453/04* | (2006.01) | |
| *C07D 487/08* | (2006.01) | |
| *C07D 487/04* | (2006.01) | |
| *C07C 211/63* | (2006.01) | |

(52) U.S. Cl.
CPC .......... *C07D 311/80* (2013.01); *C07C 211/63* (2013.01); *C07C 215/40* (2013.01); *C07D 453/04* (2013.01); *C07D 487/04* (2013.01); *C07D 487/08* (2013.01)

(58) Field of Classification Search
CPC .................................................. C07D 311/80
See application file for complete search history.

(56) References Cited

U.S. PATENT DOCUMENTS

| | | | |
|---|---|---|---|
| 9,376,367 B2 * | 6/2016 | Herkenroth | ............. C07C 51/42 |
| 9,730,911 B2 | 8/2017 | Verzura et al. | |
| 10,059,684 B2 | 8/2018 | Changoer et al. | |
| 10,239,808 B1 | 3/2019 | Black et al. | |
| 10,246,431 B2 | 4/2019 | Changoer et al. | |
| 10,406,453 B2 | 9/2019 | Ko et al. | |
| 10,413,843 B2 | 9/2019 | Ko et al. | |
| 10,478,747 B2 | 11/2019 | Ko | |

FOREIGN PATENT DOCUMENTS

| | | |
|---|---|---|
| CA | 2866787 A1 | 4/2013 |
| WO | 2019/057994 A1 | 3/2019 |
| WO | 2020/016875 A1 | 1/2020 |

OTHER PUBLICATIONS

International Search Report issued in International Application No. PCT/CA2020/050825 dated Aug. 28, 2020 (3 pages).
Written Opinion issued in International Application No. PCT/CA2020/050825 dated Aug. 28, 2020 (6 pages).
Notice of Allowance issued in corresponding CA Application No. 3,105,910 dated Mar. 11, 2021 (1 page).

* cited by examiner

*Primary Examiner* — Matthew P Coughlin
(74) *Attorney, Agent, or Firm* — Osha Bergman Watanabe & Burton LLP

(57) ABSTRACT

Disclosed are methods for separating, recovering, and purifying tetrahydrocannabinolic acid (THCA) salts from an organic solvent solution comprising a mixture of cannabinoids. The methods comprise solubilizing the mixture of cannabinoids in a selected C5-C7 hydrocarbon solvent, adding thereto a selected amine to thereby precipitate a THCA-amine salt therefrom, dissolving the recovered THCA-amine salt in a selected solvent and then adding thereto a selected antisolvent to thereby recrystallize a purified THCA-amine salt therefrom. The recrystallized THCA-amine salt may be decarboxylated to form a mixture of Δ9-tetrahydrocannabinol (Δ9-THC) and amine. The Δ9-THC amine mixture may be acidified to separate the amine from Δ9-THC. The recovered Δ9-THC may be concentrated to produce a highly purified Δ9-THC. Also disclosed are THCA-amine salts produced with amines selected from groups of diamines, amino alcohols, and tertiary amines.

32 Claims, 29 Drawing Sheets

| | |
|---|---|
| Compound: | CBD-V |
| Signal: | DAD1A |
| Exp. RT: | 2.996 |
| Corr. Coeff.: | 0.999219 |
| Residual: | 14.66874 |
| RF RSD%: | |
| $R^2$: | 0.99844 |
| Formula: | y = ax + b |
| a: | 2.17877 |
| b: | 13.86985 |
| c: | 0.00000 |
| d: | |

| | |
|---|---|
| Compound: | THC-V |
| Signal: | DAD1A |
| Exp. RT: | 5.029 |
| Corr. Coeff.: | 0.998914 |
| Residual: | 20.46903 |
| RF RSD%: | |
| $R^2$: | 0.99783 |
| Formula: | y = ax + b |
| a: | 2.04858 |
| b: | 0.00000 |
| c: | 0.00000 |
| d: | |

| | |
|---|---|
| Compound: | CBD |
| Signal: | DAD1A |
| Exp. RT: | 5.303 |
| Corr. Coeff.: | 0.998795 |
| Residual: | 22.36350 |
| RF RSD%: | |
| $R^2$: | 0.99759 |
| Formula: | y = ax + b |
| a: | 2.12389 |
| b: | 0.00000 |
| c: | 0.00000 |
| d: | |

| | |
|---|---|
| Compound: | CBG |
| Signal: | DAD1A |
| Exp. RT: | 5.490 |
| Corr. Coeff.: | 0.999159 |
| Residual: | 18.66113 |
| RF RSD%: | |
| R^2: | 0.99832 |
| Formula: | y = ax + b |
| a: | 2.11730 |
| b: | 0.00000 |
| c: | 0.00000 |
| d: | |

| | |
|---|---|
| Compound: | CBD-A |
| Signal: | DAD1A |
| Exp. RT: | 5.840 |
| Corr. Coeff.: | 0.999937 |
| Residual: | 10.30874 |
| RF RSD%: | |
| R^2: | 0.99987 |
| Formula: | y = ax + b |
| a: | 3.90496 |
| b: | 0.00000 |
| c: | 0.00000 |
| d: | |

| | |
|---|---|
| Compound: | CBG-A |
| Signal: | DAD1A |
| Exp. RT: | 6.511 |
| Corr. Coeff.: | 0.998842 |
| Residual: | 43.52347 |
| RF RSD%: | |
| R^2: | 0.99768 |
| Formula: | y = ax + b |
| a: | 4.21677 |
| b: | 0.00000 |
| c: | 0.00000 |
| d: | |

| | |
|---|---|
| Compound: | CBN |
| Signal: | DAD1A |
| Exp. RT: | 6.892 |
| Corr. Coeff.: | 0.999823 |
| Residual: | 22.29990 |
| RF RSD%: | |
| R^2: | 0.99965 |
| Formula: | y = ax + b |
| a: | 4.98620 |
| b: | 0.00000 |
| c: | 0.00000 |
| d: | |

| | |
|---|---|
| Compound: | Δ9-THC |
| Signal: | DAD1A |
| Exp. RT: | 7.532 |
| Corr. Coeff.: | 0.999038 |
| Residual: | 19.36267 |
| RF RSD%: | |
| R^2: | 0.99808 |
| Formula: | y = ax + b |
| a: | 2.04445 |
| b: | 0.00000 |
| c: | 0.00000 |
| d: | |

| | |
|---|---|
| Compound: | Δ8-THC |
| Signal: | DAD1A |
| Exp. RT: | 7.811 |
| Corr. Coeff.: | 0.998742 |
| Residual: | 18.73847 |
| RF RSD%: | |
| R^2: | 0.99749 |
| Formula: | y = ax + b |
| a: | 1.74128 |
| b: | 0.00000 |
| c: | 0.00000 |
| d: | |

| | |
|---|---|
| Compound: | CBC |
| Signal: | DAD1A |
| Exp. RT: | 8.545 |
| Corr. Coeff.: | 0.999200 |
| Residual: | 41.44812 |
| RF RSD%: | |
| R^2: | 0.99840 |
| Formula: | y = ax + b |
| a: | 4.83302 |
| b: | 0.00000 |
| c: | 0.00000 |
| d: | |

| | |
|---|---|
| Compound: | THC-A |
| Signal: | DAD1A |
| Exp. RT: | 9.007 |
| Corr. Coeff.: | 0.998955 |
| Residual: | 30.12272 |
| RF RSD%: | |
| R^2: | 0.99791 |
| Formula: | y = ax + b |
| a: | 3.07164 |
| b: | 0.00000 |
| c: | 0.00000 |
| d: | |

| Name | RT | Peak Area % | Amount [ng] | Concentration [μg/mL] |
|---|---|---|---|---|
| CBG-A | 6.565 | 7.30 | 7.340 | 1.4680 |
| THC-A | 9.013 | 92.70 | 124.928 | 24.9857 |

| Name | RT | Peak Area % | Amount [ng] | Concentration [μg/mL] |
|---|---|---|---|---|
| CBG-A | 6.554 | 2.79 | 3.253 | 0.6505 |
| THC-A | 9.013 | 97.21 | 151.894 | 30.3787 |

| Name | RT | Peak Area | Amount [ng] | Concentration [µg/mL] |
|---|---|---|---|---|
| CBG-A | 6.551 | 3.79 | 5.012 | 1.0025 |
| Δ9-THC | 7.547 | 3.04 | 6.471 | 1.6942 |
| THC-A | 9.012 | 93.18 | 165.354 | 33.0707 |

| Name | RT | Peak Area | Amount [ng] | Concentration [µg/mL] |
|---|---|---|---|---|
| CBG-A | 6.544 | 3.57 | 5.458 | 1.0916 |
| THC-A | 9.009 | 95.30 | 195.031 | 39.0063 |

| Name | RT | Peak Area % | Amount [ng] | Concentration [µg/mL] |
|---|---|---|---|---|
| CBG-A | 6.558 | 1.76 | 2.262 | 0.4524 |
| Δ9-THC | 7.571 | 3.12 | 8.338 | 1.6672 |
| THC-A | 9.016 | 93.89 | 159.699 | 31.9398 |

| Name | RT | Peak Area % | Amount [ng] | Concentration [µg/mL] |
|---|---|---|---|---|
| CBG-A | 6.562 | 1.82 | 2.550 | 0.5099 |
| THC-A | 9.013 | 98.18 | 184.722 | 36.9443 |

| Name | RT | Peak Area % | Amount [ng] | Concentration [µg/mL] |
|---|---|---|---|---|
| CBG-A | 6.561 | 3.17 | 6.958 | 1.3916 |
| THC-A | 9.017 | 96.74 | 282.030 | 56.4060 |

| Name | RT | Peak Area % | Amount [ng] | Concentration [µg/mL] |
|---|---|---|---|---|
| THC-A | 9.014 | 100.00 | 181.952 | 36.3903 |

| Name | RT | Peak Area % | Amount [ng] | Concentration [µg/mL] |
|---|---|---|---|---|
| CBG-A | 6.543 | 2.57 | 4.605 | 0.9210 |
| THC-A | 9.010 | 96.52 | 236.993 | 47.3986 |

| Name | RT | Peak Area % | Amount [ng] | Concentration [µg/mL] |
|---|---|---|---|---|
| THC-A | 9.007 | 100.00 | 285.377 | 57.0753 |

METHODS FOR EXTRACTION, PROCESSING, AND PURIFICATION OF A SELECTED FAMILY OF TARGET COMPOUNDS FROM CANNABIS

CROSS-REFERENCE

This application claims the benefit of U.S. Provisional Patent Application No. 62/860,382 filed Jun. 12, 2019, its entire contents hereby incorporated by reference. This application also claims the benefit of U.S. Provisional Patent Application No. 62/891,013 filed Aug. 23, 2019, its entire contents hereby incorporated by reference.

TECHNICAL FIELD

Various embodiments disclosed herein generally relate to methods for processing mixtures of phytochemicals extracted from plant biomass feedstocks. More specifically, this disclosure pertains to methods for separating and purifying tetrahydrocannabinol compounds from plant extracts recovered from *Cannabis sativa* plant biomass feedstocks.

BACKGROUND

It is well known that plants from the Cannabaceae family produce at least two different classes of terpenophenolic phytochemicals that can affect human physiology and metabolism. The most prominent of these molecules are tetrahydrocannabinol (THC) and cannabidiol (CBD).

Cannabaceae is a small family of flowering plants that includes about 170 species grouped in 11 genera that include *Cannabis* (hemp, marijuana). It is well known that the number of species in the *Cannabis* genus is disputed. The *Cannabis* genus is most commonly considered to comprise one specie, i.e., *Cannabis sativa*. However, the *Cannabis* genus may be also be separated by some, into three subspecies i.e., *Cannabis sativa, Cannabis indica*, and *Cannabis ruderalis*. Furthermore, some consider that the *C. sativa* nomenclature includes *C. ruderalis*. It is to be noted that herein, the term *Cannabis* sp. is meant to include all species and subspecies of the *Cannabis* genus.

*Cannabis* sp. are known to produce at least 113 distinct cannabinoids and over 50 terpenes that are concentrated in viscous resins produced in plant structures known as glandular trichomes. Trichomes are located at about the axial growing tips of *Cannabis* plants. Perhaps the most recognized cannabinoids are tetrahydrocannabinol (THC) and cannabidiol (CBD). It is well known that THC has significant but temporary psychoactive effects (i.e., hallucinogenic) on mammalian physiology and for this reason, various formats of *Cannabis* sp. plant materials and extracts are consumed for recreational use. It is also well known that CBD does not have psychoactive effects (i.e., hallucinogenic) but does have significant calming and pain relief effects. As an aggregate group of compounds, *Cannabis* terpenes are known to provide characteristic distinct aromas and flavors. It is also known that terpenes interact with cannabinoids to modulate the physiological effects of cannabinoids.

It is also well known that fiber-type cannabis, commonly known as hemp, has relatively high levels of CBD with very low levels or no levels of THC and consequently, is considered to have no or only minimal psychoactive and/or anxiogenic effects. The term "hemp" derives its definition from legal and/or regulatory distinctions for fiber-type cannabis strains and cultivars that stably and reproducibly have less than 0.3% THC in the USA. In Canada, a "List of Approved Cultivars for the 2019 Growing Season: Industrial Hemp Varieties Approved for Commercial Production" released by Health Canada (https://www.canada.ca/en/health-canada/services/drugs-medication/cannabis/producing-selling-hemp/commercial-licence/list-approved-cultivars-cannabis-sativa.html), listed 52 approved hemp cannabis cultivars in Canada.

Cannabinoid compounds used for both recreational and medicinal purposes are almost exclusively extracts that have been solubilized and recovered from cannabis plants. The most commonly known and widely used cannabis extraction methods are based on the use of organic solvents. Some drawbacks associated with such methods include poor or inconsistent yields and high costs associated with extraction and purification of extract and toxicity of some of the extraction solvents. Government regulations and security for cannabis plants are also an important consideration that adds to the overhead cost of producing extracts containing cannabinoid compounds.

From a technical standpoint, conventional extraction methods using non-aqueous solvents, and the like are too crude or too complex, inefficient, time consuming, and/or expensive. Conventional methods of extraction that have been used to separate the above and other constituents of botanical materials, and to produce enriched extracts of same, include maceration, decoction, and extraction with aqueous and non-aqueous solvents, and distillation. While there is a wide variety of extraction technologies to be applied to botanical materials, such extraction methodologies do not retain as many extracted target molecules once the solvent is removed. In particular, no conventional extraction technology allows for sufficient extraction and purification of the cannabinoid compounds without substantial loss or transformation of the target compounds. Furthermore, extraction solvents used in current methodologies are not effectively removed from the extracted materials without significant simultaneous loss of target molecules.

A significant challenge in assuring the delivery of consistent reproducible quality and content of extracts, including cannabinoid extracts of THC and CBD, is due to natural variations of endogenous phytochemicals that occur in plants. The chemical "fingerprint" of a particular species of a botanical can vary widely depending on the age of the plant, time of harvest, soil conditions, weather conditions, and myriad other factors. It is known that botanicals with very different phytochemical profiles will have different therapeutic effects, even if the botanicals are recovered from the same plant species. Standardization of botanical extracts provides the batch-to-batch reproducibility of a final product. A standardized extract has a concentration of marker compound that is known to a high degree of accuracy, and because both the amount of botanical material that is extracted and the amount of a carrier that may be added can be varied, it is possible to compensate for natural variability in the plant material. Also, if endogenous phytochemical active components of a standardized botanical extract are administered to patients in known quantities, then the treatments following prognosis of a diseases can be monitored. Therefore, there is a need for standardized and reproducible extracts of botanicals, including extracts derived from *C. sativa*.

SUMMARY

The embodiments of the present disclosure generally relate to methods for separating, recovering, and purifying one or more tetrahydrocannabinol phytochemicals (referred to herein as "THCs") from crude extracts prepared from a cannabis plant biomass samples.

Some embodiments of the present disclosure generally relate to methods for solubilizing concentrated complex extract mixtures comprising cannabinoids and cannabis phytochemicals, that were solvent-extracted from *Cannabis sativa* biomass after which, the solvents may have been removed thereby concentrating the extracts.

According to some aspects, the concentrated extract mixtures may be selectively solubilized in an organic solvent such as an alkane or a petroleum ether thereby producing solvent-solubilized cannabis extract mixtures. Those skilled in this art will understand that petroleum ethers are distillation fractions of low molecular weight aliphatic hydrocarbons having low boiling point (b.p.) ranges of about 30° C. to about 100° C.

According to some aspects, a selected amine may be added to and commingled with a solvent-solubilized cannabis extract mixture to thereby precipitate a THCA-amine salt. The precipitated THCA-amine salt may be washed one or more times with a selected alkane and then dried to produce a dry purified THCA-amine salt.

According to some aspects, a dried washed THCA-amine salt may be purified by re-solubilization in a selected organic solvent after which, a purified THCA-amine salt may be recrystallized from the solution by addition thereto of a selected antisolvent. Alternatively, a dried washed THCA-amine salt may be solubilized into a solution by warming the THCA-amine salt until it is dissolved and then, the THCA-amine salt may be recrystallized by cooling the solution. The purified recrystallized THCA-amine salt may be washed one or more times with a selected alkane and then dried to produce a dried purified THCA-amine salt.

According to some aspects, the purified THCA-amine salt may be decarboxylated by adding and dissolving the THCA-amine salt into a sodium carbonate solution and mixing the solution at about 100° C. for about 4 hr to thereby form an oil comprising $\Delta^9$-THC and the amine. The decarboxylated $\Delta^9$-THC may be dissolved into a selected alkane solvent or alternatively, may be dissolved into a low-boiling petroleum ether. The dissolved amine may then be partitioned from the dissolved $\Delta^9$-THC by the addition of aqueous HCl thereby forming an aqueous layer containing the amine therein, and an organic layer containing the $\Delta^9$-THC therein. After separation and removal of the aqueous layer, the solvent may then be removed from the organic layer thereby producing an oil containing therein highly purified $\Delta^9$-THC.

Some embodiments disclosed herein related to methods for the use of selected amines to produce purified THCA-amine salts. A selected amine may be added to an alkane-solubilized complex mixtures of cannabinoids to precipitate therefrom a THCA-amine salt. The precipitated THCA-amine salt may be washed one or more times with a selected alkane solvent, and then dried to produce a purified THCA-amine salt.

According to some aspects, a suitable amine for precipitating a THCA-amine salt may be selected from a group of diamines, for example, 1,8-diazabicyclo[5.4.0]undec-7-ene (DBU), 1,5-diazabicyclo[4.3.0]non-5-ene (DBN), 1,4-diazabicyclo[2.2.2]octane (DABCO), tetramethylethylenediamine (TMEDA), and the like.

According to some aspects, a suitable amine for precipitating a THCA-amine salt may be selected from a group of amino alcohols such as dimethylethanolamine (DMEA), piperidineethanol, and the like.

According to some aspects, a suitable amine for precipitating a THCA amine salt may be selected from a group of tertiary amines, for example, triethylamine, ethyldiisopropylamine (Hunig's base), quinine, and the like.

According to some aspects, a suitable amine for precipitating a THCA amine salt may be a secondary amine, for example, dicyclohexylamine.

BRIEF DESCRIPTION OF THE DRAWINGS

The present invention will be described in conjunction with reference to the following drawings in which.

DETAILED DESCRIPTION

Figure 1A:
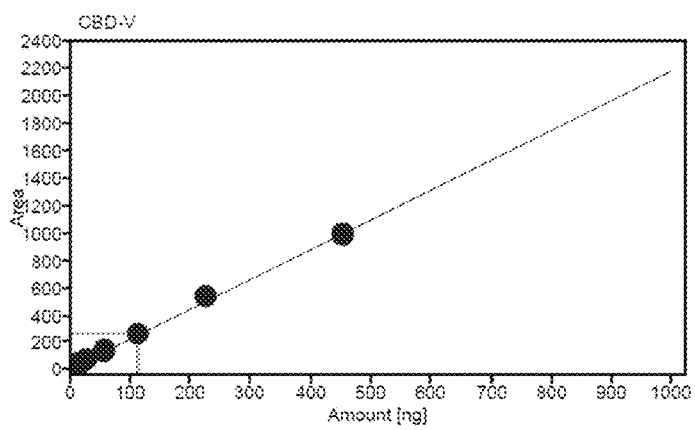
FIG. 1A is a chart showing a linear calibration curve for cannabidivarin (CBDV)

No language or terminology in this specification should be construed as indicating any non-claimed element as essential or critical. All methods described herein can be performed in any suitable order unless otherwise indicated herein. The use of any and all examples, or example language (e.g., "such as") provided herein, is intended merely to better illuminate example embodiments and does not pose a limitation on the scope of the claims appended hereto unless otherwise claimed.

It should be noted that if the stereochemistry of a structure or a portion of a structure is not indicated with, for example, bold or dashed lines, the structure or the portion of the structure is to be interpreted as encompassing all stereoisomers of it. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

Throughout this specification, the word "comprise", or variations such as "comprises", "comprising", "including", "containing", and the like, will be understood to imply the inclusion of a stated element or integer or group of elements or integers but not the exclusion of any other element or integer or group of elements or integers, unless the context requires otherwise.

To facilitate understanding of this example embodiments set forth herein, a number of terms are defined below. Generally, the nomenclature used herein and the laboratory procedures in biology, biochemistry, organic chemistry, medicinal chemistry, pharmacology described herein are generally well known and commonly employed in the art. Unless defined otherwise, all technical and scientific terms used herein generally have the same meaning as commonly understood in the art to which this disclosure belongs. In the event that there is a plurality of definitions for a term used herein, those in this written description shall prevail unless stated otherwise herein.

As used herein, the singular forms "a", "an", and "the," may also refer to plural articles, i.e., "one or more", "at least one", "and/or", are open-ended expressions that are both conjunctive and disjunctive in operation. For example, the term "a cannabinoid" includes "one or more cannabinoids". Further, each of the expressions "at least one of A, B, and C", "at least one of A, B, or C", "one or more of A, B, and C", "one or more of A, B, or C" and "A, B, and/or C" means A alone, B alone, C alone, A and B together, A and C together, B and C together, or A, B and C together. The term "an entity" refers to one or more of that entity. As such, the terms "a", "an", "one or more", and "at least one" can be used interchangeably herein.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller subranges are also included. The upper and lower limits of these smaller ranges are also included therein, subject to any specifically excluded limit in the stated range.

The terms "about" or "approximately" as used herein, mean an acceptable error for a particular recited value, which depends in part on how the value is measured or determined. In certain embodiments, "about" can mean one or more standard deviations. When the antecedent term "about" is applied to a recited range or value it denotes an approximation within the deviation in the range or value known or expected in the art from the measurement method. For removal of doubt, it shall be understood that any range stated in this written description that does not specifically recite the term "about" before the range or before any value within the stated range inherently includes such term to encompass the approximation within the deviation noted above.

As used herein, the terms "cannabis" and "cannabis biomass" encompass whole *Cannabis sativa* plants and also parts thereof which contain cannabinoids and cannabis phytochemicals, such as the aerial parts of the plants or isolated leaves and/or flowering heads and/or seeds. The term also encompasses freshly harvested cannabis plant material and also plant material, cannabis plant material that was dried after harvesting. Dried cannabis plant material may be in a loose form or alternatively, may be baled into square bales or rectangular bales or round bales or alternatively, may be compressed into cubes or pellets or cubes. Dried cannabis plant material may be separated into two or more components wherein one component comprises the cannabis stalks and stems, and a second component comprises the leaves, trichomes, and flowers. The second component may be further separated into leaves and trichome/flower components and the trichome/flower components may be separated into trichome and flower components. The separated dried cannabis plant material components may be stored in a loose form and/or processed into a baled form and/or processed into a compressed form. The separated dried cannabis plant material components may be packaged and stored in a packaging material.

Freshly harvested and/or dried harvested cannabis biomass may be processed with a selected solvent to separate and recover therefrom in a crude extract, a complex mixture of cannabinoids and cannabis phytochemicals.

The term "cannabinoid" as used herein encompasses cannabidiol (CBD), cannabidiolic acid (CBDA), cannabinol (CBN), cannabigerol (CBG), cannabigerolic acid (CBGA), cannabichromene (CBC), cannabichromenic (CBCA), cannabicyclol (CBL), cannabivarin (CBV), cannabidivarin (CBDV), cannabidivarinic (CBDVA), cannabichromevarin (CBCV), cannabigerovarin (CBGV), cannabigerol monomethyl ether (CBGM), cannabielsoin (CBE), cannabicitran (CBT), among others. The term "cannabinoid" may also be substituted for herein by the acronym "CBD". The term "tetrahydrocannabinol" as used herein encompasses (−)-Trans-$\Delta^9$-tetrahydrocannabinol ($\Delta^9$-THC), $\Delta^8$-tetrahydrocannabinol ($\Delta^8$-THC), iso-tetrahydrocannabinol, tetrahydrocannabinolic acid (THCA), tetrahydrocannabivarin (THCV), tetrahydrocannabivarinic acid (THCVA), among others. The term "tetrahydrocannabinol" may also be substituted for herein by the acronym "THC".

The term "cannabis phytochemicals" as used herein, refers to biologically active compounds produced by *Cannabis sativa* plants, and in particular, to mixtures of terpenes, terpenoids, flavonoids, alkaloids, lignans, omega fatty acids, pigments, and the like, that may be extracted and separated from cannabis biomass by solvent extraction. The term "phytochemical" as used herein, refers to a single biologically active compound that has been separated from a mixture of phytochemicals.

The term "solvent" as used herein, is used herein to denote a liquid or gas capable of dissolving a solid or another liquid or gas. Non-limiting examples of solvents include alcohols such as methanol, ethanol, propanol, isopropanol, butanol, C3-C7 hydrocarbon solvents such as alkanes and ethers having b.p. less than 110° C., toluene, ethyl acetate, acetone (also known as propanone), dichloromethane, 1,4-dioxane, tetrahydrofuran, acetonitrile, supercritical carbon dioxide ($CO_2$), subcritical $CO_2$, hot water, supercritical $H_2O$, subcritical $H_2O$, and the like.

As used herein, the term "antisolvent" refers to a solvent that may be used to precipitate a target compound or molecule from another solvent in which the target compound or molecule is completely dissolved whereby, as the antisolvent is added to the solvent containing the dissolved target compound or molecule, the precipitation process is initiated by nucleation of the target compound or molecule followed by the formation of solid particles.

The term "crude precipitate" as used herein means the solids and/or oils produced by a chemical reaction between a selected organic base with a mixture of cannabinoid carboxylic acids present in a crude cannabis extract. The "crude precipitate" may also be referred to herein as a "crude isolate" or a "carboxylic acid salt" or a "precipitated cannabinoid".

The term "purified precipitate" as used herein means the solids and/or oils remaining after the crude precipitate is washed with a selected solvent such as, for example, with ethyl acetate at 40° C. A purified precipitate may also be produced via a recrystallization process wherein the crude precipitate is dissolved in a heated solvent and then cooled to an appropriate temperature to induce crystallization. Alternatively, the crude precipitate may be dissolved in a solvent which readily dissolves both the desired purified precipitate and the impurities present in the crude precipitate, followed by addition of an antisolvent in which the desired purified precipitate is insoluble and the impurities remain in solution. Subsequent filtration yields the purified precipitate. The "purified precipitate" may also be referred as a "purified isolate" or a "purified cannabinoid precipitate" or a "purified cannabinoid carboxylic acid".

As used herein, the term a "standardized solvent-solubilized crude extract" refers to a crude extract that has been adjusted by the addition or removal of a solvent to adjust the concentrations therein of one or more bioactive markers, such as THCA, to a selected target range in comparison to the concentrations of the one or more bioactive markers in a reference solution, using analytical methods known to those skilled in these arts. For example, suitable analytical methods include HPLC methods and the like.

Without being bound by any theory of operation or mechanism of action, the examples of embodiments disclosed herein are based in part, on an unpredicted/unexpected discovery that use of an amine having a suitably placed heteroatom such as oxygen or nitrogen, can effectuate the transfer of the acidic proton from the carboxylic acid to the amine by stable/strong hydrogen bonding in the ammonium ion, as shown below, and thereby drive the acid-base reaction to completion and facilitate the crystallization of the desired salt as shown in Eqn 1 and Eqn 2:

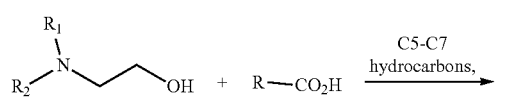

Eqn 1

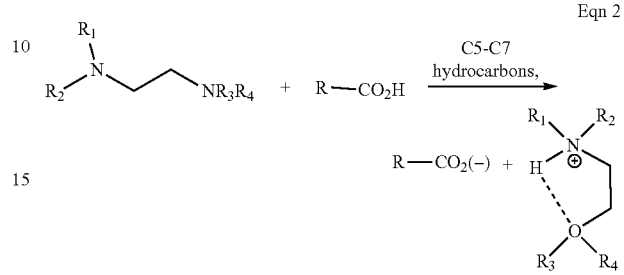

Eqn 2

It was surprisingly discovered that some amines precipitated THCA salts from crude *C. sativa* extracts solubilized in certain organic solvents such as, for example, C5-C7 low-boiling hydrocarbon solvents including alkanes and petroleum ethers. The amine-precipitated THCA salts, also referred to herein as THCA-amine salts, have very low solubilities in a number of organic solvents at room temperature and therefore, may be washed with those organic solvents to remove more soluble impurities and produce highly purified THCA-amine salts.

Figure 23:
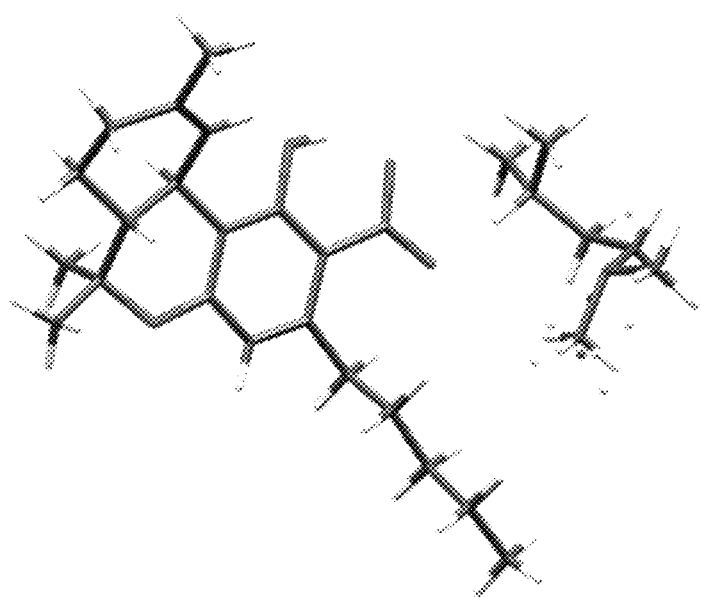
FIG. 23 shows the X-ray structure of the THCA-TMEDA salt.

For example, it was discovered that certain amino alcohols and particularly N,N-dialkylethanolamines such as N, N.dimethylaminoethanol and piperidineethanol, readily produce solid salts with THCA that are present in solvent-solubilized crude extracts comprising complex mixtures of cannabinoids and cannabis phytochemicals, despite the relatively high acidity of their ammonium ions [$(CH_3)_2$ $NHCH_2OH^+$ pKa=9.3]. It was also discovered that 1,3-diamines such as tetramethylethylenediamine (TMEDA, pka of the protonated TMEDA is 9.0) and 1,4-diazo [2,2,2] bicyclooctane (DABCO, pka of the protonated DABCO=8.9), also precipitate THCA-amine salts having characteristics similar to those produced with the aforementioned amino alcohols. The strong hydrogen bonding in the ammonium ion of the salt as shown below may raise the melting point of the desired salt since it makes that portion of the molecule more rigid and better able to fit into a lattice. This is shown clearly in the X-ray structure of the THCA-TMEDA salt (FIG. 23).

It was further discovered that the diamines 1,5-diazabicyclo[4.3.0]non-5-ene (DBN) and 1,8-diazabicyclo[5.4.0] undec-7-ene (DBU) readily form salts upon reacting with THCA solubilized in organic solvents, and it was observed that such THCA-amine salts remain as solids at ambient room temperatures. DBN and DBU are very strong bases with rigid bicyclic structures and with a pKa value of 13.5.

(2)

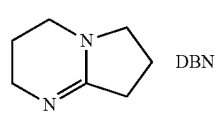

DBN (3)

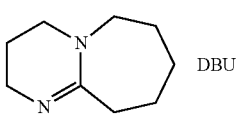

DBU

It was further discovered that amines such as tertiary amines such as quinine, N,N-diisopropylethylamine (also known as Hunig's base), and such as triethylamine, also form solid THCA-amine salts from solvent-solubilized crude C. sativa extracts. It was further discovered that a secondary amine, dicyclohexylamine, also forms solid THCA-amine salts from solvent-solubilized crude C. sativa extracts.

This surprisingly contrasts with the observations that many other equally and even more basic amines including benzylamine, cyclohexylamine, tert-butlyamine, piperidine, dicyclohexylamine, tributlyamine, tripropylamine, and isopropylcyclohexylamine failed to produce solid salt precipitates when added to solvent-solubilized crude cannabis extracts known to comprise THCA. Furthermore, it was observed that weakly acidic amines such as aromatic and heteroaromatic amines, for example aniline and N,N-dimethylaniline, whose conjugate bases have species with pKa values lower than 5, failed to give even insoluble oil salts when added to a solution containing THCA. In these cases, the equilibrium for salt formation is not as favorable as with the much more basic amines, as shown in Eqn 3:

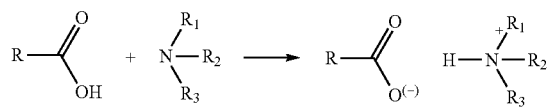

Eqn 3

Therefore, according to an embodiment of the present disclosure, it was discovered that, at an ambient temperature, addition of an equivalent amount of DMEA into an organic hydrocarbon solvent containing therein a complex mixture of cannabis compounds extracted from C. sativa plant biomass (i.e., a crude extract), results in an immediate phase separation THCA-amine salt from the complex solvent mixture into an oil form that may be subsequently precipitated into a solid salt form. The structure of the precipitated THCA-amine salt produced in the above reaction can be verified by $^1$H NMR spectroscopy which shows the expected 6:1:1 ratio of the hydrogen nuclei due to the dimethylamino group [2.6 ppm, s, 6H] present in the basic component, the remaining single hydrogen ion on the aromatic ring [6.2 ppm, s, 1H] and the alkene H [6.8 ppm, broad s, 1H] due to the THC moiety.

The precipitated THCA-amine salt may be recrystallized and purified by (i) first slurrying and at least partially dissolving the salt in a selected volume of a solvent such as, for example, ethyl acetate or heptane or a mixture thereof, and then (ii) slowly adding a selected suitable solvent such as hexane or heptane or pentane or petroleum ether until recrystallization of the THCA into a purified salt form commences.

Alternatively, the precipitated THCA-amine salt can be dissolved in a minimum of a suitable organic solvent by heating, and the cooling to thereby cause recrystallization to occur.

Then, the recrystallized THCA salt may be dissolved in a suitable polar aprotic solvent, for example ethyl acetate, to which is added a 0.1M-HCl solution to cause partitioning of the mixture into an aqueous layer and an organic solvent layer. Sufficient 0.1M-HCl solution is added until the aqueous layer turns litmus paper a red color. The two resulting layers may be separated using separation processes known to those skilled in this art. HPLC analysis of the partitioned ethyl acetate layer will show the presence of very high-purity $\Delta^9$-THCA (in reference to a $\Delta^9$-THCA standard). Ethyl acetate may be removed from the partitioned organic layer thereby producing very high-purity $\Delta^9$-THCA initially as an oil that solidifies into a powder form.

It is to be noted that crystallization is an important step for separation and purification of THCA. Crystallization involves two key steps: (i) formation of solid particles from liquid solution (nucleation) and (ii) growth due to the deposition of additional substances on existing particles. The thermodynamic driving force behind both steps is the difference in chemical potential between solution i.e. liquid phase and crystal i.e. solid phase. In practice, the difference can be represented by supersaturation, which is defined as the difference between the actual concentration of the crystallizing substance in the solution and its saturation concentration. Generally, crystallization of cannabinoids in a solvent mixture is a function of temperature and time. For example, a way to induce crystallization is to lower the temperature below the saturation point of a particular constituent that can then precipitate out of the solution as a solid. Crystallization may also be induced by providing seed crystals to the mixture and/or by scratching an inner surface of the vessel wherein the mixture is contained.

According to some embodiments of the present disclosure, other suitable amine bases, in addition to DMEA, that may be used in the methods disclosed herein to precipitate THCA-amine salts from solvent-solubilized crude C. sativa extracts, include without limitation DMEA, dicyclohexylamine, piperidineethanol, TMEDA, DBU, DBN, DABCO, N,N-diisopropylethylamine (Hunig's base), quinine, dicyclohexylamine, and the like.

An embodiment of the present disclosure pertains to an example method for separating out, recovering, and purifying THCA in the form of a THCA-amine salt, from a crude extract comprising a mixture of cannabinoids and cannabis phytochemicals recovered from processing cannabis biomass, and then converting the purified THCA-amine salt into a purified $\Delta^9$-THC product. The example method comprises the steps of:

1. assaying a crude C. sativa extract to determine the concentration of THCA therein;
2. adding to and commingling a first organic solvent with the crude extract to reduce the THCA content therein to a level within a selected target range in reference to a THCA standard, thereby producing a standardized solvent-solubilized crude extract;
3. adding and mixing into the standardized solvent-solubilized crude extract, a selected volume of a selected amine whereby the amine reacts with THCA in an acid-base reaction, thereby forming and precipitating a crude THCA-amine salt;
4. separating and recovering the precipitated crude THCA-amine salt from the standardized solvent-solubilized crude extract;
5. washing the recovered crude THCA-amine salt with a selected second organic solvent one or more times to thereby produce a washed THCA-amine salt;
6. re-solubilizing the washed THCA-amine salt in a selected third organic solvent;
7 crystalizing the solubilized THCA-amine salt by cooling and optionally adding a selected antisolvent, to thereby produce a purified crystallized THCA-amine salt;
8. decarboxylating the purified THCA-amine salt to produce an oil comprising $\Delta^9$-THC and amine;

9. solubilizing the oil comprising $\Delta^9$-THC in a selected fourth organic solvent to thereby partition therefrom an organic layer containing a highly purified $\Delta^9$-THC oil and the amine, and an aqueous layer;
10. separating the organic layer containing the highly purified $\Delta^9$-THC and the amine from the aqueous layer;
11. acidifying the organic layer to partition therefrom an organic layer containing highly purified $\Delta^9$-THC in the form of an oil, and an aqueous layer containing the amine; and
12. concentrating the highly purified $\Delta^9$-THC oil by volatilization of the fourth organic solvent therefrom.

According to an aspect, a suitable first organic solvent for use in step 2 may be a C5-C7 hydrocarbon such as an alkane or a low b.p. petroleum ether. Particularly suitable alkanes include such as heptane, hexane, pentane, their isomers, and the like. It is optional if so desired, to solubilize the crude *C. sativa* extract in a selected volume of the first organic solvent prior to assaying the crude *C. sativa* extract in step 1.

According to an aspect, a suitable target range for adjusting the THCA content to in step 2 may be from about 20 mg/mL to about 150 mg/mL. A particularly suitable target range may be from about 30 mg/mL to about 70 mg/mL. A preferred target range may be from about 31 mg/mL to about 47 mg/mL.

According to another aspect, a suitable amine for use in step 3 may be a N,N-dialkylethanolamine such as DMEA, piperidineethanol, and the like. Alternatively, a suitable amine may be a 1,3-diamine such as TMEDA, DABCO, and the like. Alternatively, a suitable amine may be DBN, DBU, dicyclohexylamine, Hunig's base, triethylamine, quinine, and the like.

According to another aspect, the standardized solvent-solubilized crude extract may be spiked with a selected volume of denatured alcohol prior to step 3 of adding and mixing the selected amine thereinto. A suitable volume of denatured alcohol may be selected from a range of about 2% to about 10% by volume of the standardized solvent-solubilized crude extract. Alternatively, the standardized solvent-solubilized crude extract may be spiked with a selected volume of acetone prior to adding and mixing the selected amine thereinto. A suitable volume of acetone may be selected from a range of about 4% to about 20% by volume of the standardized solvent-solubilized crude extract.

According to another aspect, a suitable second organic solvent for washing the recovered crude THCA-amine salt in step 5, may be a C5-C7 hydrocarbon solvent such as an alkane or a petroleum ether. Suitable alkanes include heptane, hexane, pentane, their isomers, and the like. Particularly suitable alkanes are heptane and hexane.

According to another aspect, a suitable third organic solvent for resolubilizing the washed THCA-amine salt in step 6, may be one of ethyl acetate, ethanol, methanol, dichloromethane, toluene, and the like. A particularly suitable solvent for resolubilizing the washed THCA-amine salt in step 7, may be ethyl acetate heated to about 60° C.

According to another aspect, a suitable antisolvent for recrystallizing the solubilized THCA salt in step 7, may be an alkane such as one of heptane, hexane, pentane, and the like. Additionally, water may be a suitable antisolvent if an alcohol has been selected as the third solvent.

According to another aspect, the recrystallized purified THCA salt may be decarboxylated in step 8, by adding the THCA salt into a sodium carbonate ($Na_2CO_3$) solution, then heating the mixture under constant mixing at a temperature selected from a range of about 90° C. to reflux for a period of time selected from a range of about 2 hr to about 18 hr, thereby producing an oil comprising $\Delta^9$-THC and amine in the $Na_2CO_3$ solution. A suitable concentration of $Na_2CO_3$ solution to use for this step is from a range of about 1% to about 15% (w/v). A particularly suitable concentration of $Na_2CO_3$ solution is from a range of about 2.5% to about 10% (w/v), for example, about 5% (w/v). A particularly suitable temperature for this decarboxylation step is about 100° C. A particularly suitable time duration for this decarboxylation step is about 4 hr.

According to another aspect, the $\Delta^9$-THC can be suspended and separated from the $Na_2CO_3$ solution in step 9, by the addition of an alkane to the $Na_2CO_3$ solution to dissolve the $\Delta^9$-THC thereinto and to partition the $Na_2CO_3$ solution into an organic phase containing highly purified d $\Delta^9$-THC and amine therein and an aqueous phase containing the $Na_2CO_3$ solution and residual contaminants separated from the decarboxylated $\Delta^9$-THC.

According to another aspect, the amine may be separated from the $\Delta^9$-THC by acidification of the organic layer with a mineral acid thereby producing an organic layer comprising highly purified $\Delta^9$-THC oil, and an aqueous layer containing the amine. Suitable mineral acids may be HCl or $H_2SO_4$ and the like.

According to some embodiments, the methods disclosed herein may additionally comprise steps for processing *C. sativa* biomass to producing and further processing crude extracts comprising complex mixtures of cannabinoids and cannabis phytochemicals prior to the step of producing a solvent-solubilized crude *C. sativa* extract according to the example method disclosed herein. For example, *C. sativa* biomass may be extracted with an organic solvent, for example, an alkane such as heptane, hexane, propane, butane, pentane, and the like to produce a crude *C. sativa* extract. Alternatively, *C. sativa* biomass may be extracted with an alcohol such as methanol, ethanol, propanol, isopropanol, butanol, and the like to produce a crude *C. sativa* extract. After separating and recovering the crude *C. sativa* extract from the spent biomass, the recovered crude *C. sativa* extract may be concentrated into a crude extract oil form by volatilization of the organic solvent, ideally under reduced pressure.

Another embodiment of the present disclosure pertains to an example method for preparing a crude extract from cannabis biomass, then separating out, recovering, and purifying THCA from the crude extract in the form of a THCA-amine salt, then converting the purified THCA-amine salt into a purified $\Delta^9$-THC product in the form of an oil. The example method comprises the steps of:
1. processing a *C. sativa* biomass in a selected first organic solvent to produce a solvent-solubilized crude extract therefrom;
2. assaying the crude extract to determine the content of THCA therein;
3a. if so desired, adding additional first organic solvent to the solvent-solubilized crude extract to reduce the THCA content therein to a level within a selected range in reference to a THCA standard, thereby producing a standardized solvent-solubilized crude extract;
3b. if so desired, removing some of the first organic solvent from the solvent-solubilized crude extract to increase the THCA content therein to a level within a selected range in reference to a THCA standard, thereby producing a standardized solvent-solubilized crude extract;
4. adding and mixing into the standardized solvent-solubilized crude extract, a selected volume of a selected amine whereby the amine reacts with THCA in an acid-base reaction, thereby forming and precipitating a crude THCA-amine salt;
5. separating and recovering the precipitated crude THCA-amine salt from the standardized solvent-solubilized crude extract;
6. washing the recovered crude THCA-amine salt with a selected second organic solvent one or more times to thereby produce a washed THCA-amine salt;
7 re-solubilizing the washed THCA-amine salt in a selected third organic solvent to thereby produce a solution of the THCA-amine salt;
8. crystalizing the solubilized THCA-amine salt by cooling, and optionally adding a selected antisolvent, to thereby produce a purified recrystallized THCA-amine salt;
9. decarboxylating the purified THCA-amine salt to produce an oil comprising $\Delta^9$-THC and the amine;
10. solubilizing the oil comprising $\Delta^9$-THC in a selected fourth organic solvent to thereby partition therefrom an organic layer containing a highly purified $\Delta^9$-THC oil and the amine, and an aqueous layer;
11. separating the organic layer contacting the highly purified $\Delta^9$-THC organic layer and amine from the aqueous layer;
12. acidifying the highly purified $\Delta^9$-THC organic layer to partition therefrom an organic layer consisting of highly purified $\Delta^9$-THC in the form of an oil, and an aqueous layer containing the amine;
13. separating the aqueous layer from the highly purified $\Delta^9$-THC oil; and
14. concentrating the highly purified $\Delta^9$-THC oil by volatilization of the fourth organic solvent therefrom.

According to an aspect, a suitable first organic solvent for use in step 1 may be a C3-C7 hydrocarbon solvent such as an alkane or a petroleum ether. Suitable alkanes include heptane, hexane, pentane, butane, propane, their isomers, and the like. Particularly suitable alkanes are heptane and hexane. It is optional if so desired, to concentrate the crude C. sativa extract into an oil form and then adding a selected volume of a C5-C5 alkane prior to assaying the crude C. sativa extract in step 2.

According to an aspect, a suitable target range for adjusting the THCA content to in step 3a or 3b may be from about 20 mg/mL to about 150 mg/mL. A particularly suitable target range may be from about 30 mg/mL to about 70 mg/mL. A preferred target range may be from about 31 mg/mL to about 47 mg/mL.

According to another aspect, a suitable amine for use in step 3 may be a N,N-dialkylethanolamine such as DMEA, piperidineethanol, and the like. Alternatively, a suitable amine may be a diamine such as TMEDA, DABCO, DBN, DBU, and the like. Alternatively, a suitable amine may be Hunig's base, triethylamine, quinine, and the like. Alternatively, a suitable amine may be dicyclohexylamine.

According to another aspect, the standardized solvent-solubilized crude extract may be spiked with a selected volume of denatured ethanol prior to adding and mixing the selected amine thereinto. A suitable volume of denatured ethanol may be selected from a range of about 2% to about 10% by volume of the standardized solvent-solubilized crude extract. Alternatively, the standardized solvent-solubilized crude extract may be spiked with a selected volume of acetone prior to adding and mixing the selected amine thereinto. A suitable volume of acetone may be selected from a range of about 4% to about 20% by volume of the standardized solvent-solubilized crude extract.

According to another aspect, a suitable second solvent for washing the recovered crude THCA-amine salt in step 6, may be an alkane such as one of heptane, hexane, pentane, their isomers, and the like. Particularly suitable alkanes are heptane and hexane.

According to another aspect, a suitable third solvent for resolubilizing the washed THCA-amine salt in step 7, may be one of ethyl acetate, ethanol, methanol, and the like. A particularly suitable solvent for resolubilizing the washed THCA-amine salt in step 7, may be ethyl acetate heated to about 60° C. to reflux.

According to another aspect, a suitable antisolvent for recrystallizing the solubilized THCA salt in step 8, may be an alkane such as one of heptane, hexane, pentane, their isomers, and the like. Particularly suitable alkanes are heptane and hexane.

According to another aspect, the recrystallized purified THCA-amine salt may be decarboxylated in step 9, by adding the THCA salt into a sodium carbonate ($Na_2CO_3$) solution, then heating the mixture under constant mixing at a temperature selected from a range of about 90° C. to reflux for a period of time selected from a range of about 2 hr to about 18 hr, thereby producing an oil comprising $\Delta^9$-THC and amine in the $Na_2CO_3$ solution. A suitable concentration of $Na_2CO_3$ solution to use for this step is from a range of about 1% to about 15% (w/v). A particularly suitable concentration of $Na_2CO_3$ solution is from a range of about 2.5% to about 10% (w/v), for example, about 5% (w/v). A particularly suitable temperature for this decarboxylation step is about 100° C. A particularly suitable time duration for this decarboxylation step is about 4 hr.

According to another aspect, the $\Delta^9$-THC and amine can be solubilized and separated from the $Na_2CO_3$ solution in step 10 by the addition of an alkane to the $Na_2CO_3$ solution dissolve the $\Delta^9$-THC therein and to partition the $Na_2CO_3$ solution into an organic phase comprising an oil containing highly purified $\Delta^9$-THC and amine therein and an aqueous phase comprising the $Na_2CO_3$ solution and residual contaminants separated from the decarboxylated $\Delta^9$-THC.

According to another aspect, the $\Delta^9$-THC may be converted into a highly purified $\Delta^9$-THC oil form by acidification of the decarboxylated $\Delta^9$-THC organic layer thereby producing an organic layer comprising highly purified $\Delta^9$-THC oil, and an aqueous layer comprising the amine.

Other embodiments of the present disclosure relate to purified THCA-amine salts that have been precipitated and recovered from solvent-solubilized crude C. sativa extracts with an amine selected from one of DMEA, piperidineethanol, TMEDA, DBU, DBN, DABCO, N,N-diisopropylethylamine (Hunig's base), quinine, triethylamine, dicyclohexylamine, and the like. An example method for producing purified THCA-amine salts comprises the steps of:
1. providing a crude extract comprising a mixture of cannabinoids and cannabis phytochemicals recovered from cannabis biomass;
2. assaying the crude extract to determine the content of THCA therein;
3. adding a selected volume of a first organic solvent to crude extract to thereby adjust the THCA content therein to within a selected range in reference to a THCA standard, thereby producing a standardized solvent-solubilized crude extract;
4. adding and mixing into the standardized solvent-solubilized crude extract, a selected volume of a selected amine whereby the amine reacts with THCA in an acid-base reaction, thereby forming and precipitating a crude THCA-amine salt;

5. separating and recovering the precipitated crude THCA-amine salt from the standardized solvent-solubilized crude extract;
6. washing the recovered crude THCA-amine salt with a selected second organic solvent one or more times to thereby produce a washed and purified THCA-amine salt;
7 re-solubilizing the washed THCA-amine salt in a selected third organic solvent to thereby produce a solution containing THCA-amine salt;
8. crystalizing the solubilized THCA-amine salt by cooling, and optionally adding with a selected antisolvent, to thereby produce a purified crystallized THCA-amine salt;
9. washing the recovered purified THCA-amine salt with the antisolvent second organic solvent one or more times to thereby produce a washed and purified THCA-amine salt; and
10. drying the purified THCA-amine salt.

Another embodiment of the present disclosure pertains to an example method for separating out, recovering, and purifying THCA in the form of a THCA-amine salt, from a crude extract comprising a mixture of cannabinoids and cannabis phytochemicals recovered from processing cannabis biomass, and then separating therefrom and recovering a highly purified THCA from the THCA-amine salt. The example method comprises the steps of:
1. assaying a crude *C. sativa* extract to determine the concentration of THCA therein.
2. adding to and commingling a first organic solvent with the crude extract to reduce the THCA content therein to a level within a selected target range in reference to a THCA standard, thereby producing a standardized solvent-solubilized crude extract;
3. adding and mixing into the standardized solvent-solubilized crude extract, a selected volume of a selected amine whereby the amine reacts with THCA in an acid-base reaction, thereby forming and precipitating a crude THCA-amine salt;
4. separating and recovering the precipitated crude THCA-amine salt from the standardized solvent-solubilized crude extract;
5. washing the recovered crude THCA-amine salt with a selected second organic solvent one or more times to thereby produce a washed THCA-amine salt;
6. re-solubilizing the washed THCA-amine salt in a selected third organic solvent;
7 crystallizing the solubilized THCA-amine salt by cooling, and optionally adding a selected antisolvent, to thereby produce a purified crystallized THCA-amine salt;
8. re-solubilizing the purified THCA-amine salt in the third selected organic solvent;
9. acidifying the solubilized purified THCA-amine salt to partition therefrom an organic layer containing the highly purified THCA in the form of an oil, and an aqueous layer containing the amine;
12. separating the aqueous layer from the organic layer containing the highly purified THCA; and
13a. concentrating the highly purified THCA by volatilization of the third organic solvent therefrom to thereby produce highly purified THCA; or alternatively
13b. placing the THCA under a negative pressure to reduce traces of remaining solvent thereby producing highly purified THCA precipitate.

According to an aspect, a suitable first organic solvent for use in step 2 may be a C5-C7 hydrocarbon such as an alkane or a low b.p. petroleum ether. Particularly suitable alkanes include such as heptane, hexane, pentane, their isomers, and the like. It is optional if so desired, to solubilize the crude *C. sativa* extract in a selected volume of the first organic solvent prior to assaying the crude *C. sativa* extract in step 1.

According to an aspect, a suitable target range for adjusting the THCA content to in step 2 may be from about 20 mg/mL to about 150 mg/mL. A particularly suitable target range may be from about 30 mg/mL to about 70 mg/mL. A preferred target range may be from about 31 mg/mL to about 47 mg/mL.

According to another aspect, a suitable amine for use in step 3 may be a N,N-dialkylethanolamine such as DMEA, piperidineethanol, and the like. Alternatively, a suitable amine may be a 1,3-diamine such as TMEDA, DABCO, and the like. Alternatively, a suitable amine may be DBN, DBU, dicyclohexylamine, Hunig's base, triethylamine, quinine, and the like.

According to another aspect, the standardized solvent-solubilized crude extract may be spiked with a selected volume of denatured alcohol prior to step 3 of adding and mixing the selected amine thereinto. A suitable volume of denatured alcohol may be selected from a range of about 2% to about 10% by volume of the standardized solvent-solubilized crude extract. Alternatively, the standardized solvent-solubilized crude extract may be spiked with a selected volume of acetone prior to adding and mixing the selected amine thereinto. A suitable volume of acetone may be selected from a range of about 4% to about 20% by volume of the standardized solvent-solubilized crude extract.

According to another aspect, a suitable second solvent for washing the recovered crude THCA-amine salt in step 5, may be a C5-C7 hydrocarbon solvent such as an alkane or a petroleum ether. Suitable alkanes include heptane, hexane, pentane, their isomers, and the like. Particularly suitable alkanes are heptane and hexane.

According to another aspect, a suitable third solvent for resolubilizing the washed THCA-amine salt in step 6, may be one of ethyl acetate, ethanol, methanol, dichloromethane, toluene, and the like. A particularly suitable solvent for resolubilizing the washed THCA-amine salt in step 7, may be ethyl acetate heated to about 60° C.

According to another aspect, a suitable antisolvent for recrystallizing the solubilized THCA salt in step 7, may be an alkane such as one of heptane, hexane, pentane, and the like.

According to an embodiment, DMEA may be added to and commingled with a solvent-solubilized crude *C. sativa* extract to precipitate therefrom a THCA-amine salt having a chemical structure shown in (4):

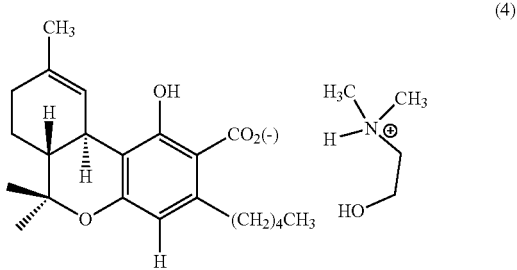

(4)

The precipitated THCA-DMEA salt may be washed with a selected organic solvent to thereby produce a purified THCA-DMEA salt.

According to another embodiment, piperidineethanol may be added to and commingled with a solvent-solubilized crude *C. sativa* extract to precipitate therefrom a THCA-amine salt having a chemical structure shown in (5):

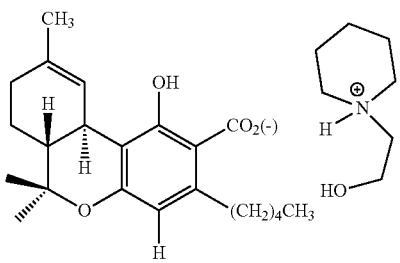

(5)

The precipitated THCA-piperidineethanol salt may be washed with a selected organic solvent to thereby produce a purified THCA-piperidineethanol salt.

According to another embodiment, triethylamine may be added to and commingled with a solvent-solubilized crude *C. sativa* extract to precipitate therefrom a THCA-amine salt having a chemical structure shown in (6):

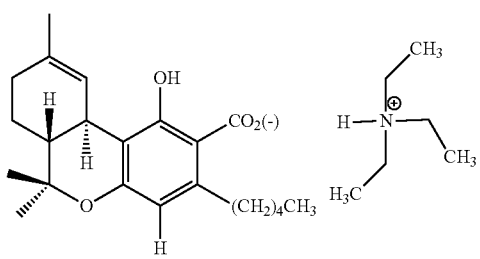

(6)

The precipitated THCA-triethylamine salt may be washed with a selected organic solvent to thereby produce a purified THCA-triethylamine salt.

According to another embodiment, ethyldiisopropylamine (Hunig's salt) may be added to and commingled with a solvent-solubilized crude *C. sativa* extract to precipitate therefrom a THCA-amine salt having a chemical structure shown in (7):

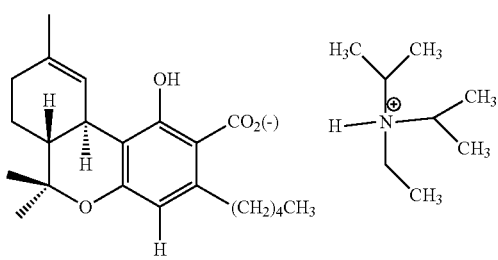

(7)

The precipitated THCA-ethyldiisopropylamine salt may be washed with a selected organic solvent to thereby produce a purified THCA-ethyldiisopropylamine salt.

According to another embodiment, DABCO may be added to and commingled with a solvent-solubilized crude *C. sativa* extract to precipitate therefrom a THCA-amine salt having a chemical structure shown in (8):

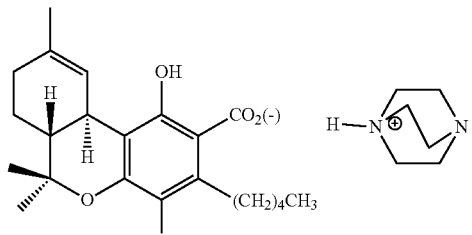

(8)

The precipitated THCA-DABCO salt may be washed with a selected organic solvent to thereby produce a purified THCA-DABCO salt.

According to another embodiment, DBN may be added to and commingled with a solvent-solubilized crude *C. sativa* extract to precipitate therefrom a THCA-amine salt having a chemical structure shown in (9):

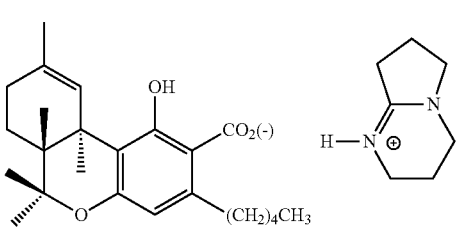

(9)

The precipitated THCA-DBN salt may be washed with a selected organic solvent to thereby produce a purified THCA-DBN salt.

According to another embodiment, DBU may be added to and commingled with a solvent-solubilized crude *C. sativa* extract to precipitate therefrom a THCA-amine salt having a chemical structure shown in (10):

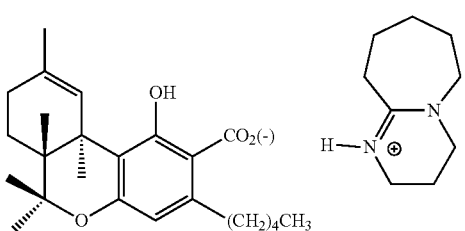

(10)

The precipitated THCA-DBU salt may be washed with a selected organic solvent to thereby produce a purified THCA-DBU salt.

According to another embodiment, TMEDA may be added to and commingled with a solvent-solubilized crude *C. sativa* extract to precipitate therefrom a THCA-amine salt having a chemical structure shown in (11):

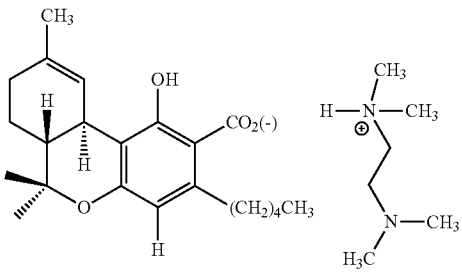

(11)

The precipitated THCA-TMEDA salt may be washed with a selected organic solvent to thereby produce a purified THCA-TMEDA salt.

According to another embodiment, quinine may be added to and commingled with a solvent-solubilized crude *C. sativa* extract to precipitate therefrom a THCA-amine salt having a chemical structure shown in (12):

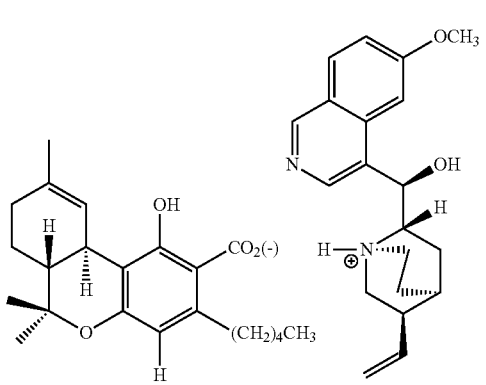

(12)

The precipitated THCA-quinine salt may be washed with a selected organic solvent to thereby produce a purified THCA-quinine salt.

According to another embodiment, dicyclohexylamine may be added to and commingled with a solvent-solubilized crude *C. sativa* extract to precipitate therefrom a THCA-amine salt having a chemical structure shown in (13):

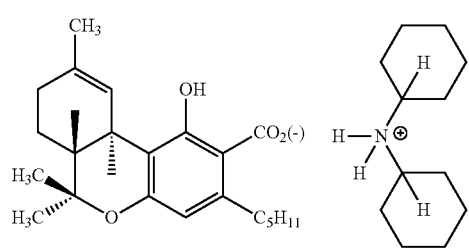

(13)

The precipitated THCA-dicyclohexylamine salt may be washed with a selected organic solvent to thereby produce a purified THCA-dicyclohexylamine salt.

The following examples are provided to more fully describe the invention and are presented for non-limiting illustrative purposes.

EXAMPLES

Example 1

Figure 1B:
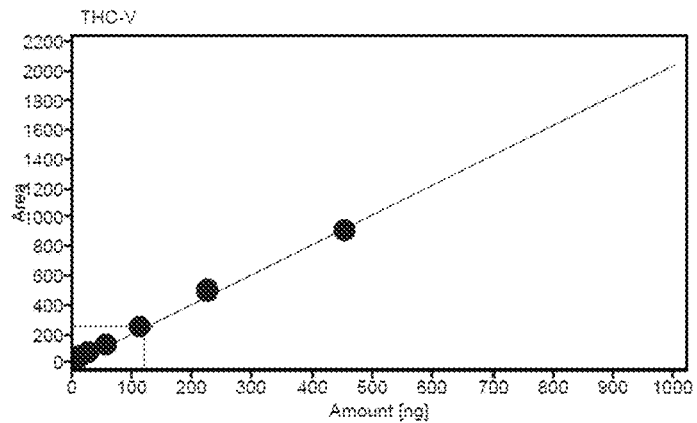
FIG. 1B is a chart showing a linear calibration curve for tetrahydrocannbidivarin (THCV)
Figure 1C:
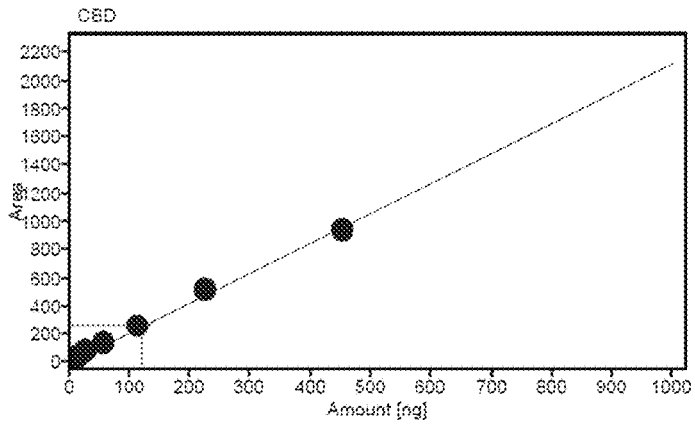
FIG. 1C is a chart showing a linear calibration curve for cannabidiol (CBD)
Figure 2A:
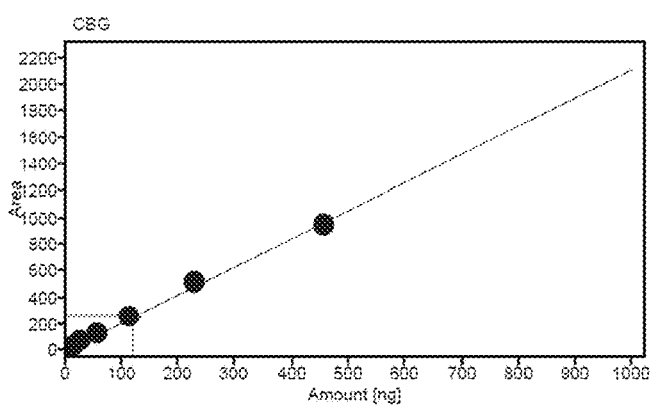
FIG. 2A is a chart showing a linear calibration curve for cannabigerol (CBG)
Figure 2B:
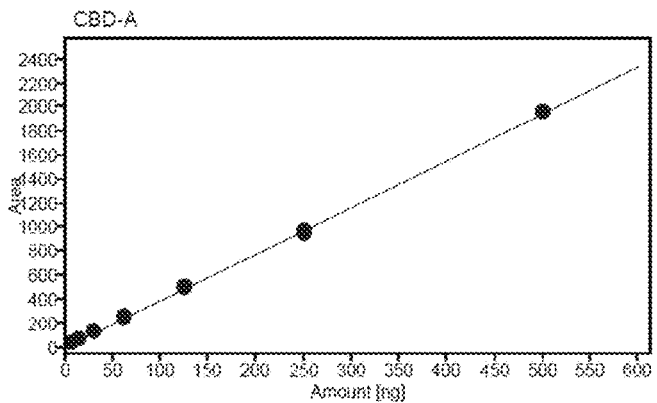
FIG. 2B is a chart showing a linear calibration curve for cannabidiolic acid (CBDA)
Figure 2C:
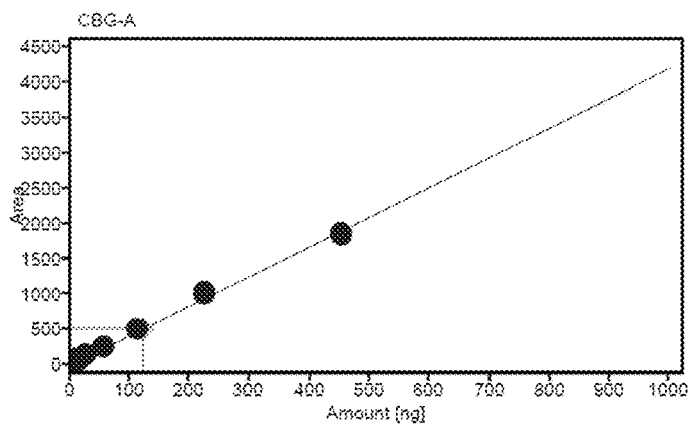
FIG. 2C is a chart showing a linear calibration curve for cannabigerolic acid (CBGA)
Figure 3A:
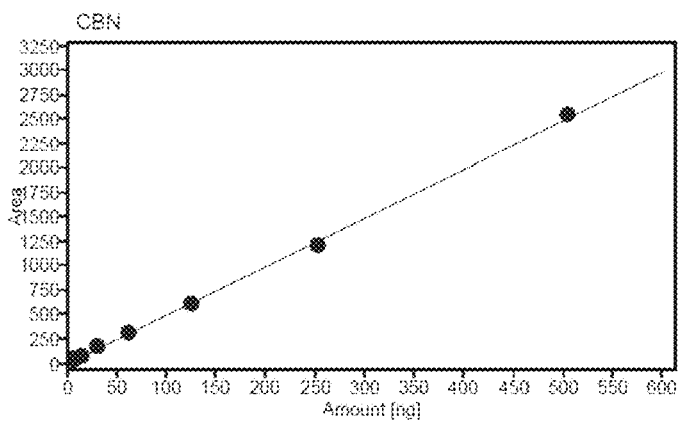
FIG. 3A is a chart showing a linear calibration curve for cannabinol (CBN)
Figure 3B:
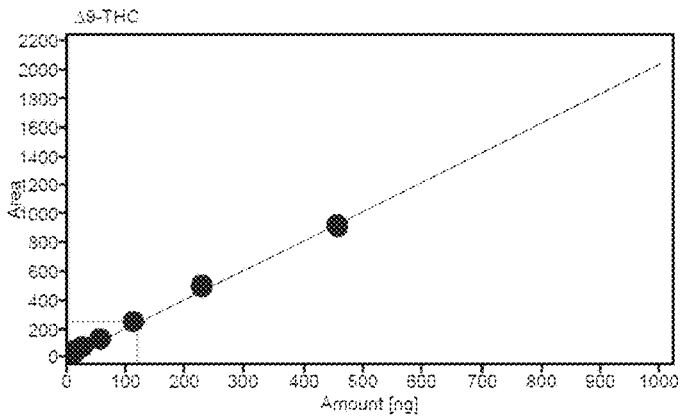
FIG. 3B is a chart showing a linear calibration curve for $\Delta^9$-tetrahydrocannabinol ($\Delta^9$-THC)
Figure 3C:
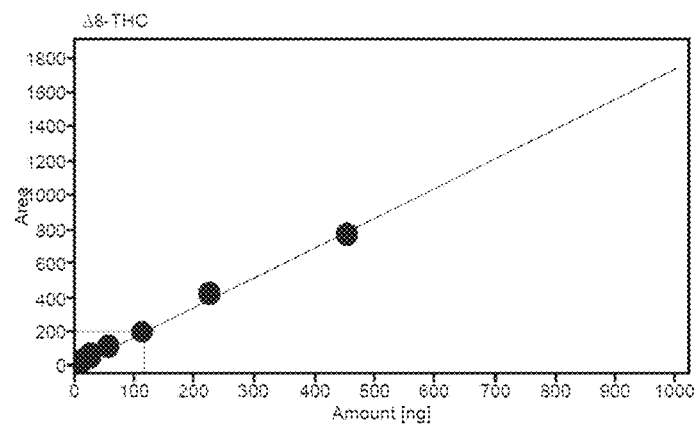
FIG. 3C is a chart showing a linear calibration curve for $\Delta^8$-tetrahydrocannabinol ($\Delta^8$-THC)
Figure 4A:
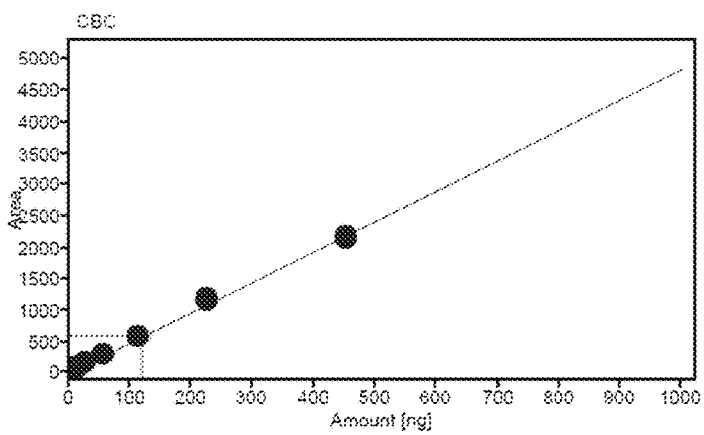
FIG. 4A is a chart showing a linear calibration curve for cannabichromene (CBC)
Figure 4B:
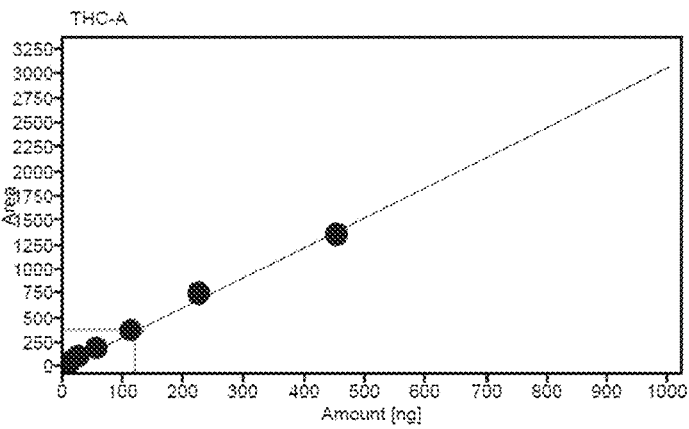
FIG. 4B is a chart showing a linear calibration curve for (−)-Trans-$\Delta^9$-tetrahydrocannabinolic acid (THCA)
Figure 5:
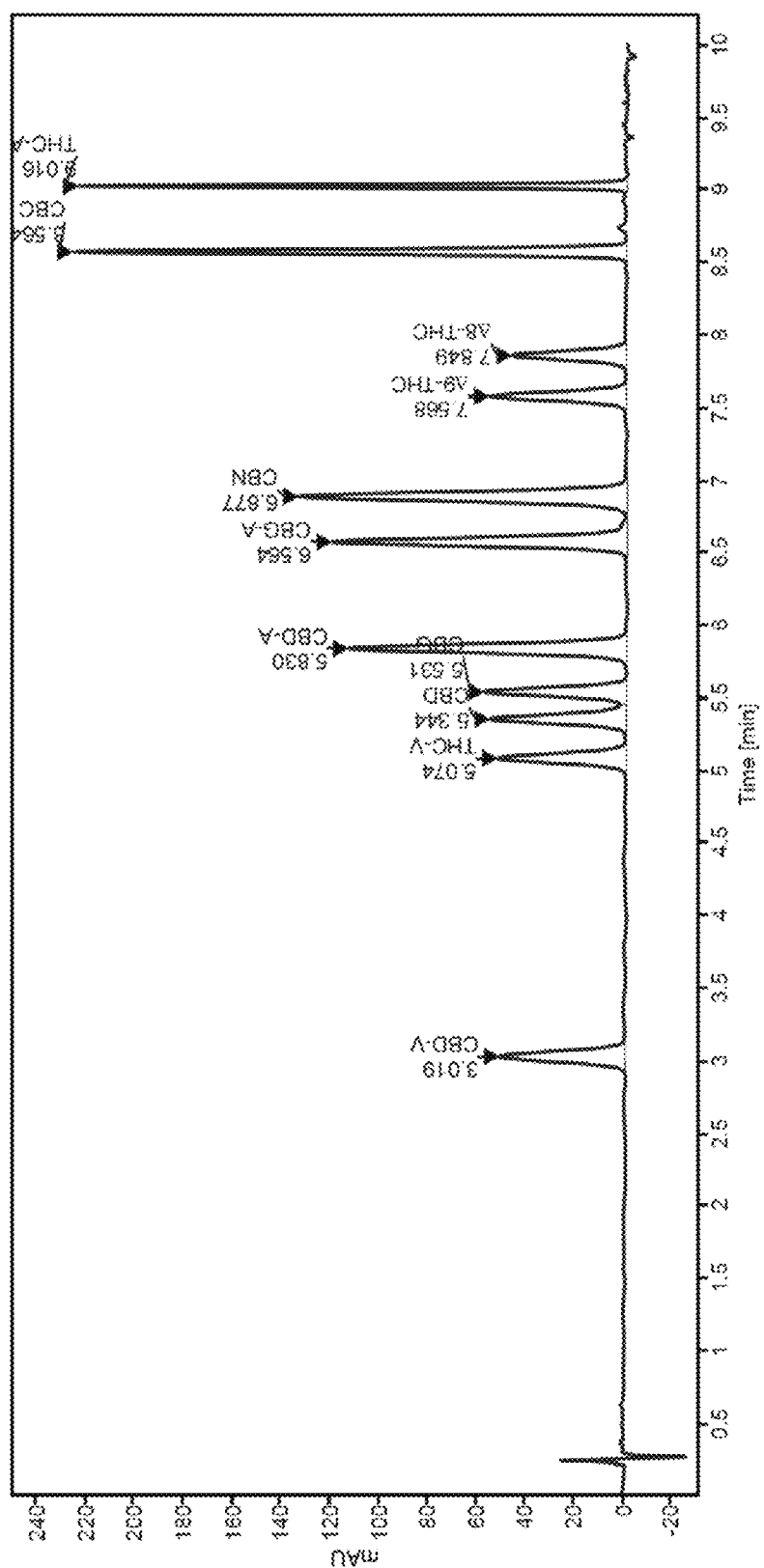
FIG. 5 is an HPLC chromatogram showing separation of a standardized reference mixture of the eleven cannabinoid phytochemicals shown in FIGS. 1A-4B.

Prior to assessing and refining the methods disclosed herein, an internal method for detecting and quantifying individual THC and CBD phytochemicals based on use of HPLC methods and equipment, was developed and tested for sensitivity, precision, and reproducibility. Eleven naturally occurring purified cannabinoid phytochemical compounds were purchased from Mandel Scientific Inc. (Guelph, ON, CA). Specifically, cannabidivarin (CBDV), tetrahydrocannbidivarin (THCV), cannabidiol (CBD), cannabigerol (CBG), cannabidiolic acid (CBDA), cannabigerolic acid (CBGA), cannabinol (CBN), (−)-trans-$\Delta^9$-tetrahydrocannabinol ($\Delta^9$-THC), cannabichromene (CBC), tetrahydrocannabinolic acid ($\Delta^8$-THCA). Seven dilutions (1.42 μg/mL, 2.84 μg/mL, 5.68 μg/mL, 11.36 μg/mL, 22.73 μg/mL, 45.45 μg/mL, 90.90 μg/mL) of each cannabinoid standard were prepared and analyzed in triplicate following the instructions in the Agilent Application Note "Dedicated Cannabinoid Potency Testing Using the Agilent 1220 Infinity II LC System" (downloaded from www.agilent.com/chem). The average of the three measurements for each of the seven dilutions was used to create a linear calibration curve for each of the eleven cannabinoid phytochemical compounds: FIG. 1A, CBDV; FIG. 1B, THCV; FIG. 1C, CBD; FIG. 2A, CBG; FIG. 2B, CBD-A; FIG. 2C, CBGA; FIG. 3A, CBN, FIG. 3B, $\Delta^9$-THC, FIG. 3C, $\Delta^8$-THC, FIG. 4A CBC; FIG. 4B, THCA. A mixture containing 22.73 μg/mL of each of the eleven above-noted cannabinoid phytochemical compounds was prepared and then analyzed with the Agilent 1220 Infinity II LC System. The HPLC analysis of the mixture is shown in FIG. 5 and summarized below in Table 1.

TABLE 1

| Name | RT | Peak Area % | Amount [ng] | Concentration [μg/mL] |
|---|---|---|---|---|
| CBD-V | 3.019 | 6.49 | 114.983 | 22.9965 |
| THC-V | 5.074 | 6.13 | 121.932 | 24.3865 |
| CBD | 5.344 | 6.34 | 121.629 | 24.3257 |
| CBG | 5.531 | 6.24 | 120.126 | 24.0252 |
| CBD-A | 5.830 | 12.32 | 125.316 | 25.0633 |
| CBG-A | 6.564 | 12.75 | 123.143 | 24.6285 |
| CBN | 6.877 | 15.31 | 120.991 | 24.1982 |
| Δ9-THC | 7.568 | 6.12 | 121.963 | 24.3925 |
| Δ8-THC | 7.849 | 5.05 | 118.237 | 23.6473 |
| CBC | 8.564 | 14.13 | 119.110 | 23.8221 |
| THC-A | 9.016 | 9.10 | 120.688 | 24.1376 |

Example 2

Figure 6A:
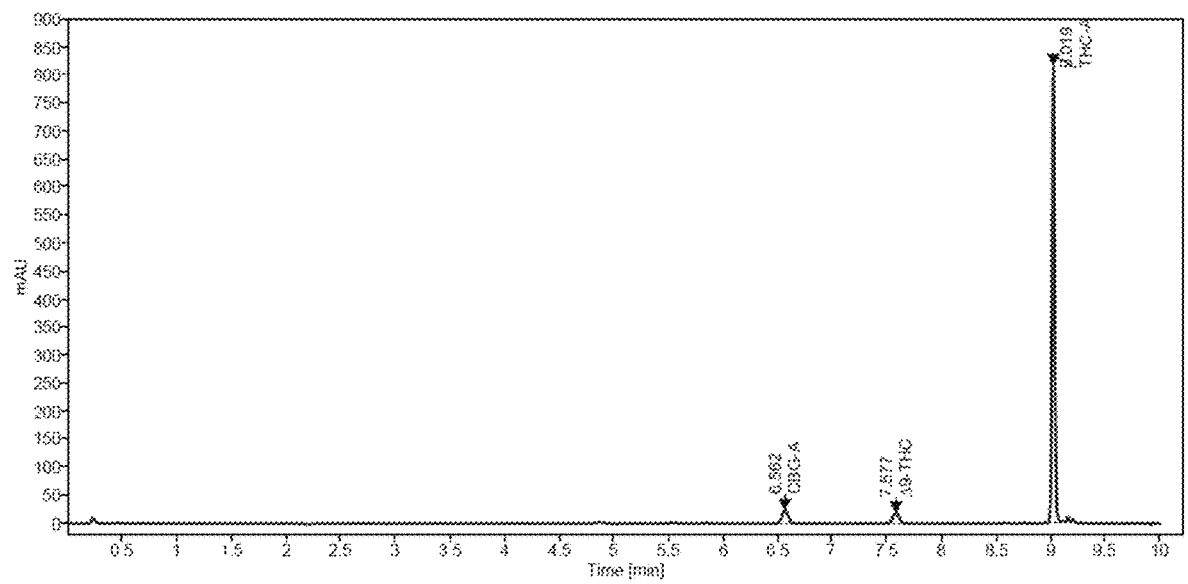
FIG. 6A is an HPLC chromatogram showing separation of cannabinoids from a solvent-solubilized crude *C. sativa* extract from Example 2.

In this example, 75.942 grams of a high-THC strain of *C. sativa* biomass were ground to a fine powder and added to heptane in a 1:3 mass/volume ratio, and then stirred continuously for 30 min at ambient room temperature. A crude extract of cannabinoids in the heptane solvent was separated from the spent *C. sativa* biomass by filtration and then analyzed with an Agilent HPLC system to determine its cannabinoid composition (FIG. 6A; Table 2).

TABLE 2

| Name | RT | Peak Area % | Amount [ng] | Concentration [µg/mL] |
|---|---|---|---|---|
| CBG-A | 6.562 | 6.33 | 22.125 | 4.4249 |
| Δ9-THC | 7.577 | 5.63 | 40.399 | 8.0797 |
| THC-A | 9.019 | 86.06 | 411.942 | 82.3883 |

The heptane solvent was removed from the crude extract by distillation to thereby produce a crude resin containing therein the $\Delta^9$-THC and THCA cannabinoids (21.02 g). The crude resin was solubilized in fresh heptane at a 20:1 volume/mass ratio thereby producing a solvent-solubilized crude extract.

Figure 6B:
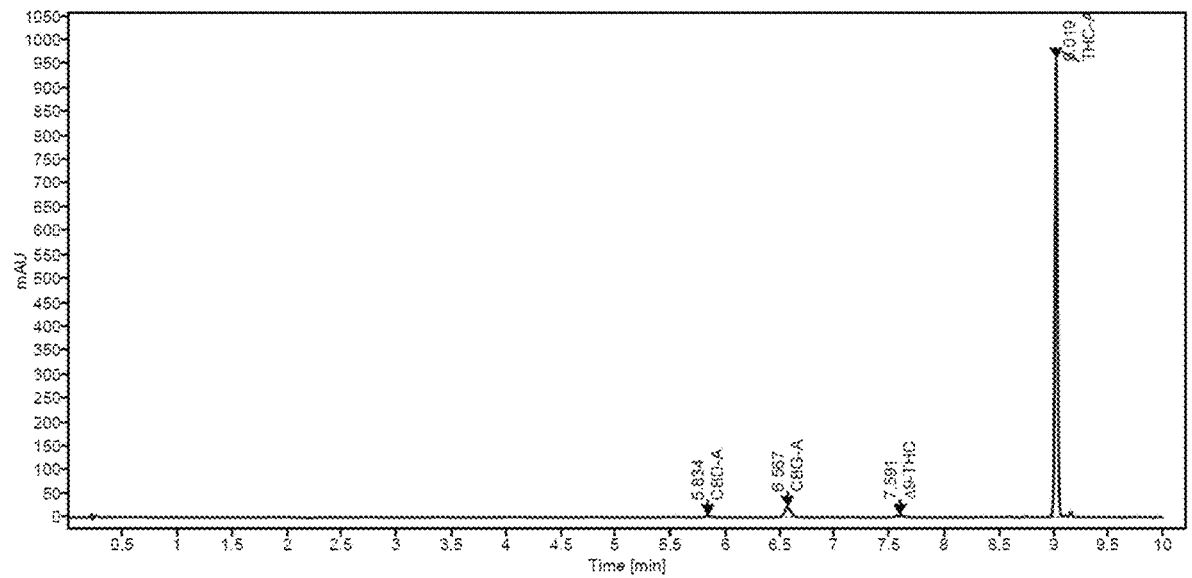
FIG. 6B is an HPLC chromatogram showing a washed crude THCA-DMEA salt precipitated and recovered from the solvent-solubilized crude *C. sativa* extract shown in FIG. 6A.

DMEA was dissolved in heptane at a 1.5:1 DMEA:THCA molar ratio, and then was added into the solvent-solubilized crude extract under a nitrogen environment (i.e., oxygen-free environment) with constant mixing thereby causing precipitation of a solid crude THCA-DMEA salt from the crude extract. The precipitated crude THCA-DMEA salt was separated and recovered by pressure filtration under a nitrogen environment, and then dried under nitrogen. The crude THCA-DMEA salt was re-suspended in heptane (5:1 volume/mass) and washed while stirring under nitrogen, and then separated from the heptane by pressure filtration under nitrogen. The crude THCA-DMEA salt was washed two more times with heptane (5:1 volume/mass) under nitrogen, and then dried under nitrogen (18.88 g). An aliquot of the washed crude THCA-DMEA was solubilized in methanol and then assayed by HPLC (FIG. 6B; Table 3).

TABLE 3

| Name | RT | Peak Area % | Amount [ng] | Concentration [µg/mL] |
|---|---|---|---|---|
| CBD-A | 5.834 | 0.67 | 2.708 | 0.5416 |
| CBG-A | 6.567 | 5.08 | 19.299 | 3.8597 |
| Δ9-THC | 7.591 | 1.17 | 9.156 | 1.8313 |
| THC-A | 9.019 | 92.13 | 479.237 | 95.8473 |

Figure 6C:
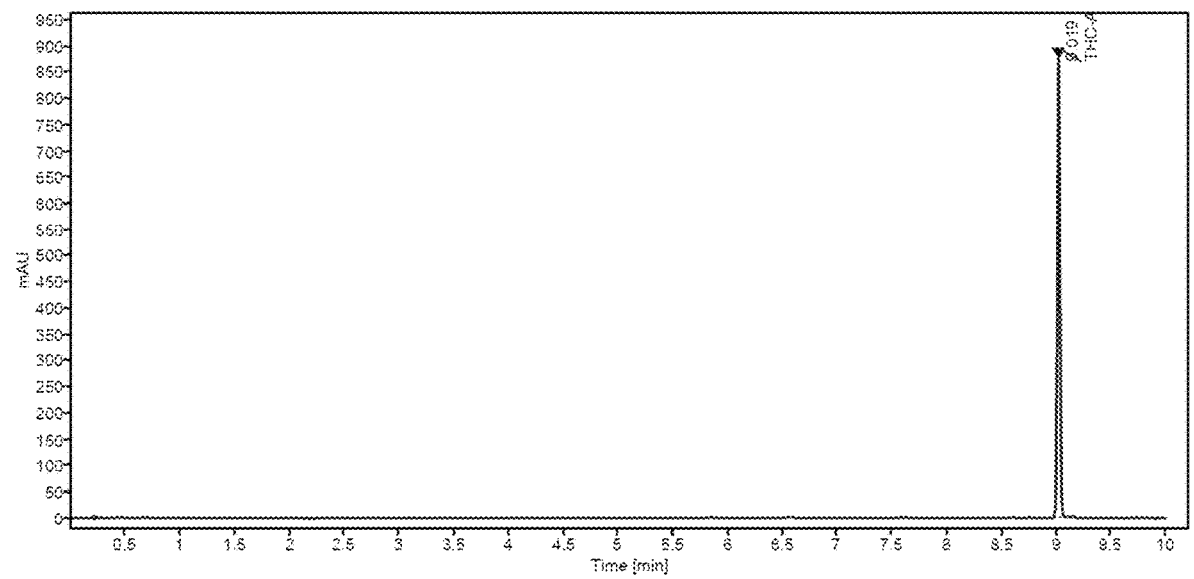
FIG. 6C is an HPLC chromatogram showing a purified THCA-DMEA salt after recrystallization of the crude THCA-DMEA salt shown in FIG. 6B.

The washed crude THCA-DMEA salt (18.88 g) was dissolved into ethyl acetate warmed to 50° C. (1:3 mass/volume) after which, the solution was cooled to about 30° C. Then, heptane was added into the warm THCA-DMEA ethyl acetate solution in a ratio of 1:3 THCA:heptane (mass/volume), thereby causing precipitation, i.e., recrystallization of the THCA-DMEA salt. The mixture was then placed into a −20° C. freezer for at least 30 min. The recrystallized THCA-DMEA salt was recovered from the liquid phase by vacuum filtration. The recrystallized THCA-DMEA salt was washed with fresh heptane solvent (3:1 vol/mass) and dried to produce a recrystallized purified THCA salt (10.16 g). An aliquot of the recrystallized purified THCA-DMEA was solubilized in methanol and then assayed by HPLC (FIG. 6C, Table 4).

TABLE 4

| Name | RT | Peak Area % | Amount [ng] | Concentration [µg/mL] |
|---|---|---|---|---|
| THC-A | 9.019 | 100.00 | 434.405 | 86.8810 |

Figure 6D:
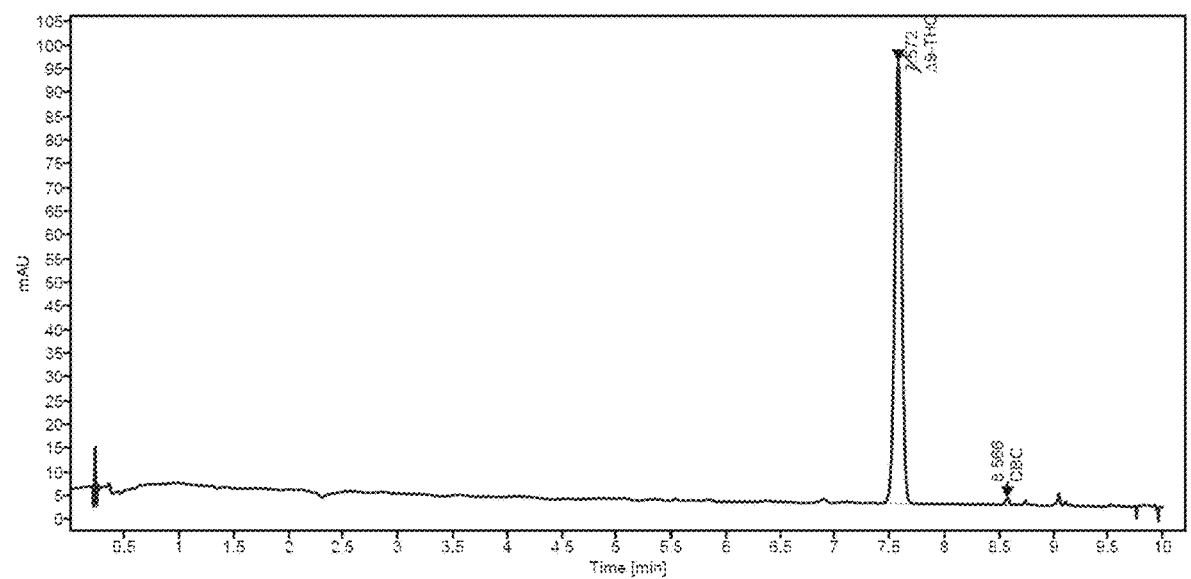
FIG. 6D is an HPLC chromatogram showing a highly purified $\Delta^9$-THC oil product after decarboxylation and partitioning of the purified THCA-DMEA salt shown in FIG. 6C.

A portion of the purified THCA-DMEA salt (4.0 g) was decarboxylated by the addition of 45 mL of a 2.5% sodium carbonate ($Na_2CO_3$) solution (10:1, vol/mass) followed by heating at about 100° C. in a rotary evaporator for about 4 hr. After the 4-hr decarboxylation process, the solution was cooled to about 60° C. after which, about 90 mL of heptane were added under constant stirring to dissolve the decarboxylated $\Delta^9$-THC and amine into the organic oil phase and partitioned the $Na_2CO_3$ solution into the aqueous phase. The mixture was allowed to cool to ambient room temperature over a 12-hr period under constant stirring. After separation of the $Na_2CO_3$ aqueous phase, the amine was recovered by adding an aqueous HCl to the recovered organic phase thereby partitioning the amine into the aqueous phase while the $\Delta^9$-THC remained in the organic phase. After removal of the aqueous phase, the heptane was distilled from the organic phase thereby producing a highly purified $\Delta^9$-THC oil product (3.46 g) (FIG. 6D, Table 5).

TABLE 5

| Name | RT | Peak Area % | Amount [ng] | Concentration [µg/mL] |
|---|---|---|---|---|
| Δ9-THC | 7.572 | 99.02 | 204.398 | 40.8797 |
| CBC | 8.566 | 0.98 | 0.848 | 0.1696 |

Example 3

Figure 7A:
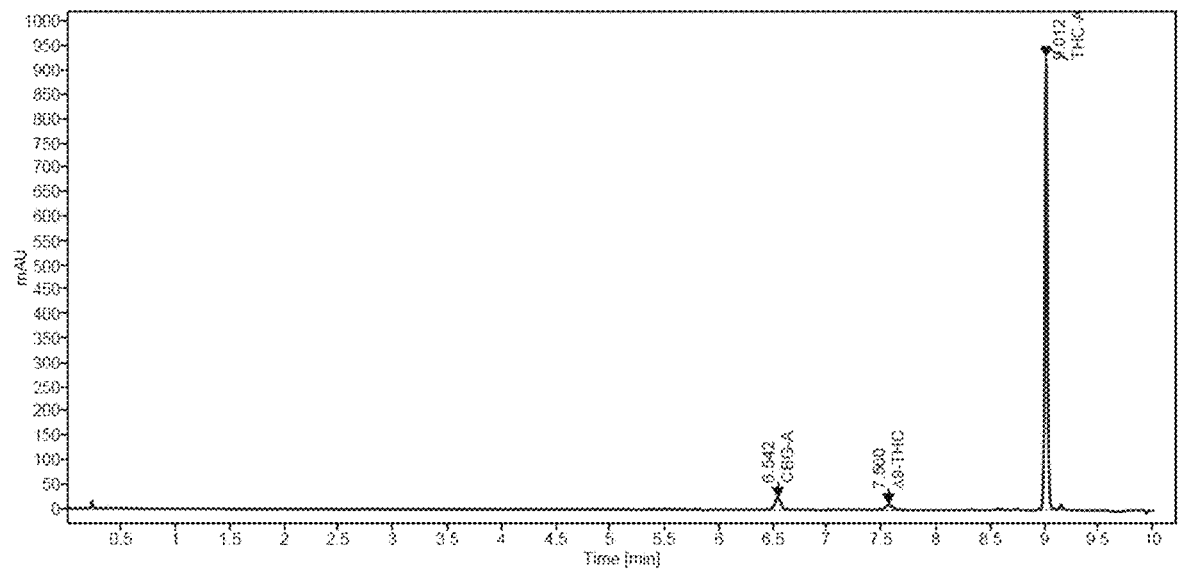
FIG. 7A is an HPLC chromatogram showing cannabinoids present in a finely ground *C. sativa* trichome biomass from Example 3.

Dried trichomes separated from a high-THC *C. sativa* biomass were ground to a fine powder. A 200-mg subsample of the trichome powder was extracted with HPLC-grade methanol. A 1-ml aliquot of the extract was centrifuged in a microfuge tube, after which, a 50-µL aliquot was diluted with 950 µL of HPLC-grade methanol thereby producing a final 50× diluted sample for analysis with an Agilent 1220 II Infinity LC Gradient UV/DAD High-Pressure Liquid Chromatography System (HPLC) in reference to the standards mixture analysis shown in Example 1. The cannabinoid composition of the *C. sativa* trichome powder comprised CBGA (5.85%), $\Delta^9$-THC (3.04%), and THCA (91.11%) (FIG. 7A; Table 6).

TABLE 6

| Name | RT | Peak Area % | Amount [ng] | Concentration [µg/mL] |
|---|---|---|---|---|
| CBG-A | 6.542 | 5.85 | 22.318 | 4.4635 |
| Δ9-THC | 7.560 | 3.04 | 23.837 | 4.7674 |
| THC-A | 9.012 | 91.11 | 476.082 | 95.2163 |

Figure 7B:
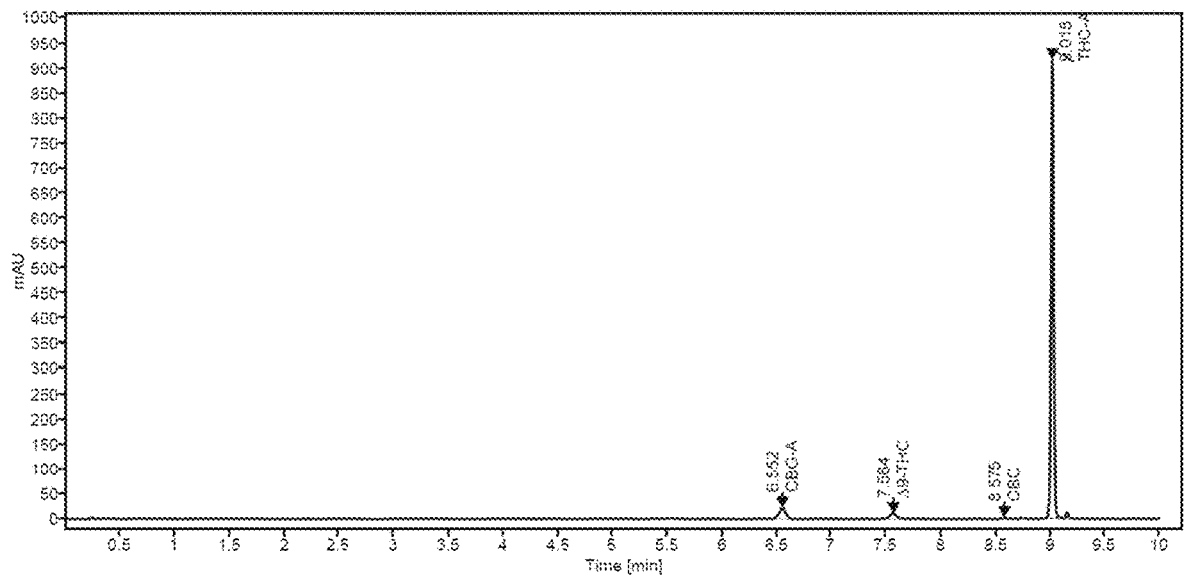
FIG. 7B is an HPLC chromatogram showing separation of cannabinoids from a solvent-solubilized crude extract prepared from the finely ground trichome biomass shown in FIG. 7A.

Then, 75.04 g of the trichome powder were extracted using 605 mL of heptane in a 1:8 mass/volume ratio to produce a solubilized resinous extract. The heptane solvent was removed by rotary evaporator to produce 20.16 g of a viscous resin. The resin was then re-solubilized in 403 mL of heptane to produce a 20:1 volume/mass standardized solvent-solubilized extract solution. A 20-µL sample of the standardized solvent-solubilized extract solution was then analyzed with the Agilent HPLC system in reference to the standards mixture analysis shown in Example 1. The cannabinoid contents of the standardized solvent-solubilized extract included CBGA (5.41%), $\Delta^9$-THC (2.88%), CBC (0.41%) and THCA (91.31%) (FIG. 7B; Table 7).

TABLE 7

| Name | RT | Peak Area % | Amount [ng] | Concentration [µg/mL] |
|---|---|---|---|---|
| CBG-A | 6.552 | 5.41 | 20.217 | 4.0434 |
| Δ9-THC | 7.564 | 2.88 | 22.072 | 4.4144 |

TABLE 7-continued

| Name  | RT    | Peak Area % | Amount [ng] | Concentration [µg/mL] |
|-------|-------|-------------|-------------|-----------------------|
| CBC   | 8.575 | 0.41        | 1.326       | 0.2652                |
| THC-A | 9.018 | 91.31       | 467.155     | 93.4311               |

Figure 7C:
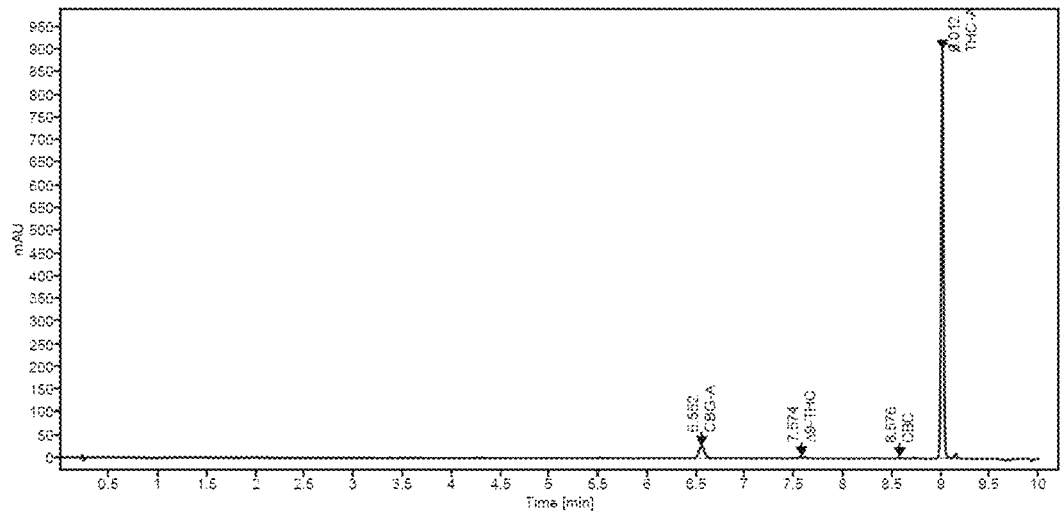
FIG. 7C is an HPLC chromatogram showing a crude THCA-DMEA salt precipitated and recovered from the solvent-solubilized crude extract shown in FIG. 7B.

DMEA was added dropwise to the standardized solvent-solubilized extract solution at a ratio of 1.5:1 molar ratio DMEA/THCA under constant mixing in a dynamic nitrogen environment thereby precipitating therefrom a solid crude THCA-DMEA salt. The crude THCA-DMEA salt was separated from the liquid phase by pressure filtration, washed with cold heptane (4° C.), and then dried under nitrogen to produce 19.52 g of crude THCA-DMEA salt. A sample of the crude THCA-DMEA salt was solubilized in methanol and analyzed with the Agilent HPLC system in reference to the standards mixture analysis shown in Example 1. The cannabinoid phytochemical contents of the crude THCA-DMEA salt included CBGA (6.66%), $\Delta^9$-THC (1.07%), CBC (0.31%), and THCA (91.65%) (FIG. 7C, Table 8).

TABLE 8

| Name   | RT    | Peak Area % | Amount [ng] | Concentration [µg/mL] |
|--------|-------|-------------|-------------|-----------------------|
| CBG-A  | 6.552 | 6.66        | 24.442      | 4.8884                |
| Δ9-THC | 7.574 | 1.07        | 8.050       | 1.6099                |
| CBC    | 8.576 | 0.31        | 0.996       | 0.1991                |
| THC-A  | 9.012 | 91.65       | 460.863     | 92.1726               |

Figure 7D:
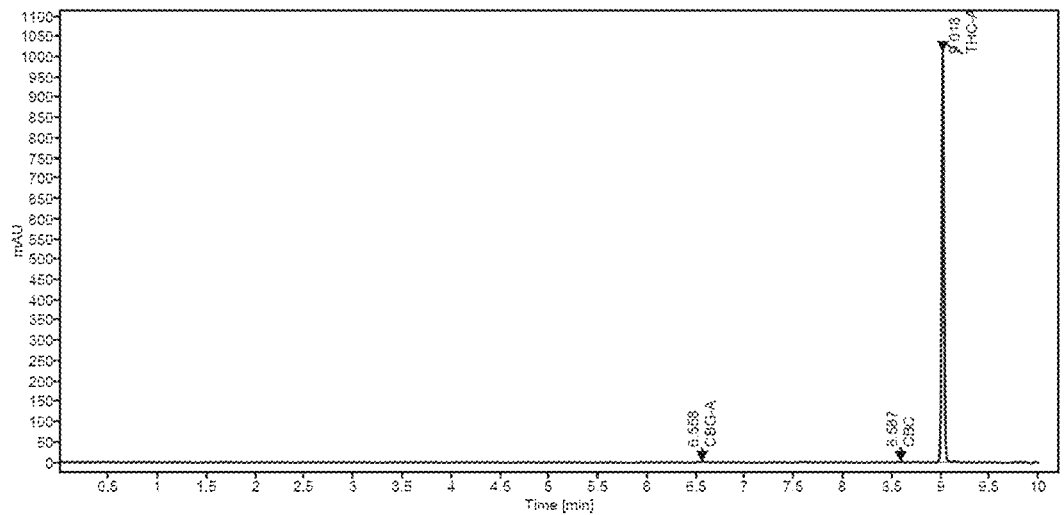
FIG. 7D is an HPLC chromatogram showing a purified THCA salt recrystallized from the crude THCA-DMEA salt shown in FIG. 7C.

The crude THCA-DMEA salt dissolved into ethyl acetate warmed to 60° C. (1:3 mass/volume) after which, the solution was cooled to about 30° C. Then under gentle mixing, ambient temperature heptane antisolvent was added to the solution in a 1:3 mass/volume ratio to recrystallize THCA-DMEA salt therefrom. The recrystallization mixture was then sealed and stored for about 10 h at −20° C. The recrystallized THCA-DMEA salt was recovered by vacuum filtration, washed with cold heptane (4° C.), recovered again by vacuum filtration, and then dried to produce 8.49 g of purified THCA-DMEA salt. A sample of the purified THCA-DMEA salt was analyzed with the Agilent HPLC system in reference to the standards mixture analysis shown in Example 1. FIG. 7D and Table 9 show that its content were 99.08% THCA and trace amounts of CBGA (0.32%) and CBC (0.30%).

TABLE 9

| Name  | RT    | Peak Area % | Amount [ng] | Concentration [µg/mL] |
|-------|-------|-------------|-------------|-----------------------|
| CBG-A | 6.558 | 0.62        | 2.349       | 0.4698                |
| CBC   | 8.587 | 0.30        | 1.000       | 0.1999                |
| THC-A | 9.018 | 99.08       | 516.625     | 103.3249              |

Figure 7E:
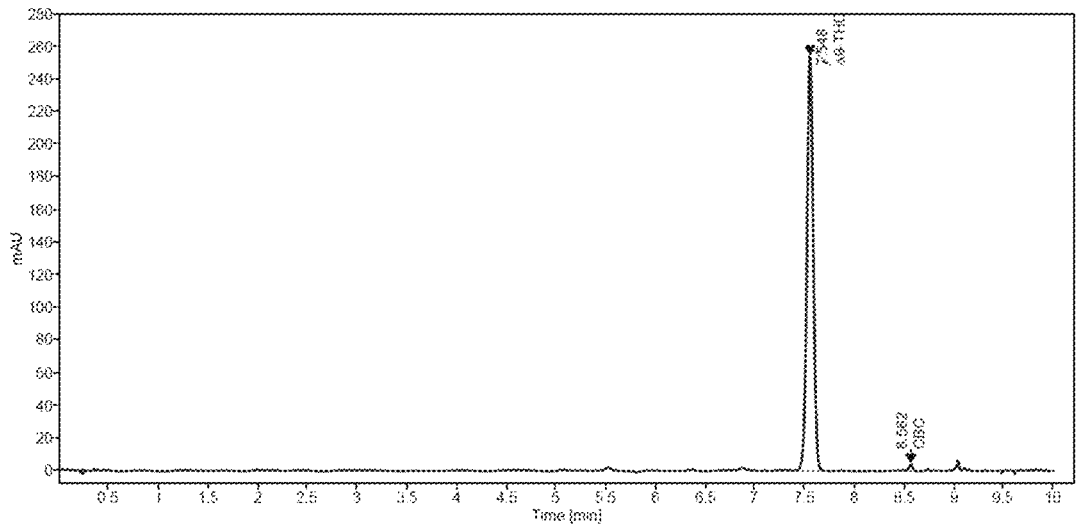
FIG. 7E is an HPLC chromatogram showing a highly purified $\Delta^9$-THC oil product prepared from the recrystallized THCA salt shown in FIG. 7D.

The purified THCA-DMEA salt was decarboxylated by dissolution in 86 mL of 2.5% $Na_2CO_3$ solution and then constantly mixed under controlled heating at about 101° C. for 4 hours to produce a mixture of decarboxylated THC, oil amine, and $Na_2CO_3$ solution. Then, about 40 mL of heptane was added to the mixture thereby dissolving $\Delta^9$-THC and amine into the organic phase and partitioning therefrom the aqueous $Na_2CO_3$ phase. The aqueous phase was then separated from the organic phase and the organic layer was washed twice with 40 mL of a 5% HCl solution. The $\Delta^9$-THC was separated from the amine whereby the $\Delta^9$-THC remained in the organic phase and the amine and HCl were partitioned into the aqueous phase. The aqueous layer was separated from $\Delta^9$-THC organic phase after which, the $\Delta^9$-THC-containing organic phase was dried over magnesium sulfate. Heptane was then removed from the $\Delta^9$-THC organic phase by distillation thereby producing 5.74 g of highly purified $\Delta^9$-THC oil. A sample of the $\Delta^9$-THC oil was analyzed with the Agilent HPLC system in reference to the standards mixture analysis shown in Example 1. FIG. 7E and Table 10 show its content was 99% purified $\Delta^9$-THC.

TABLE 10

| Name   | RT    | Peak Area % | Amount [ng] | Concentration [µg/mL] |
|--------|-------|-------------|-------------|-----------------------|
| Δ9-THC | 7.548 | 99.00       | 511.029     | 102.2058              |
| CBC    | 8.562 | 1.00        | 2.184       | 0.4368                |

Example 4

This study assessed the ability of twenty two selected amines to precipitate THCA-amine salts from THCA dissolved in an organic solvent. The THCA stock solution for this study was prepared as follows. First, a 23.15-g sample of finely ground *C. sativa* flower buds was extracted twice with 100 mL of hexane. Then, the solvent was removed under reduced pressure using a rotary evaporator to thereby produce 8.3 g of oil which was 36% of the weight of ground flower buds. The 8.3 g of oil were dissolved in 83 mL of hexane thereby producing a stock solution having a crude extract concentration of 100 mg/mL.

The following amines were assessed in this study:
Group A: Primary Amines
  1. tert-butylamine
  2. cyclohexylamine
  3. benzylamine
Group B: Secondary Amines
  4. pyrrolidine
  5. diisopropylamine
  6. dicyclohexylamine
  7. isopropylcyclohexylamine
Group C: Tertiary Amines
  8. triethylamine
  9. tripropylamine
  10. tributylamine
  11. ethyldiisopropylamime (Hunig's base)
  12. N-Methyldicyclohexylamine
  13. quinine
Group D: Amino Alcohols
  14. dimethylethanolamine (DMEA)
  15. piperidineethanol
Group E: Diamines
  16. 1,8-diazabicyclo[5.4.0]undec-7-ene (DBU)
  17. 1,5-diazabicyclo[4.3.0]non-5-ene (DBN)
  18. 1,4-diazabicyclo[2.2.2]octane (DABCO)
  19. tetramethylethylenediamine (TMEDA)
  20. N-methylpiperazine
Group F: Aromatic Amines
  21. aniline
  22. N,N-dimethylaniline Each of the above twenty two amines was solubilized in an organic solvent and then assessed for its potential to crystallize (i.e. precipitate) THCA salts by dropwise addition of an amine into a 4 mL volume of the stock solution. Each of the amines was dissolved in 1 mL of hexane, except for (i) DABCO which was dissolved in 2 mL of diethyl ether, and (ii) quinine which was dissolved in 2 mL of dichloromethane.

For each amine that precipitated a THCA-amine salt, each of the salt products was separated from the amine/hexane mixture, and then each recovered salt was washed with hexane, dried, and weighed. The results are shown in Table 11.

TABLE 11

| Amine | Salt precipitated | Yield (mg) | Yield (mmol) |
|---|---|---|---|
| Primary amines | | | |
| 1. t-butylamine | No | — | |
| 2. cyclohexylamine | No | — | |
| 3. benzylamine | No | — | |
| Seconary amines | | | |
| 4. pyrrolidine | No | | |
| 5. diisopropylamine | No | | |
| 6. isopropylcyclohexylamine | No | | |
| 7. dicyclohexylamine | Yes | 303 | 0.56 |
| Tertiary amines | | | |
| 8. triethylamine | Yes | 222 | 0.48 |
| 9. tripropylamine | No | | |
| 10. tribuytlamine | No | | |
| 11. N-ethyldiisopropylamine | Yes | 320 | 0.66 |
| 12. N-methyldicyclohexylamine | No | | |
| 13. Quinine * | Yes | NA | |
| Aminoethanols | | | |
| 14. N,N-dimethyaminoethanol | Yes | 273 | 0.62 |
| 15. piperidineethanol | Yes | 308 | 0.63 |
| Diamines | | | |
| 16. DBN | Yes | 342 | 070 |
| 17. DABCO | Yes | 322 | 0.69 |
| 18. DBU | Yes | 358 | 0.74 |
| 19. Tetramethylethylenediamine | yes | ND | |
| 20. N-methylpiperazine | No | | |
| Aromatic amines | | | |
| 21. Aniline | No | | |
| 22. N,N-dimethylaniline | No | | |

* NMR analysis showed mixture of THCA-quinine salt plus excess quinine. A pure sample of salt was obtained by recrystallization from ethyl acetate and hexane.
NA not applicable
ND not determined In this study, the following amines precipitated THCA-amine salts from an organic solvent containing solubilized THCA, as follows (listed in descending order in reference to the amount of THC-amine salts in mmol that crystallized from the THCA solutions):

1. DBU
2. DBN
3. DABCO
4. N-ethyldiisopropylamine (Hunig's base)
5. piperidineethanol
6. dicyclohexylamine
7. dimethylaminoethanol
8. triethylamine
9. quinine
10. TMEDA For most of the amines tested in this study, the yield of salt ranged from 0.62 to 0.70 mmole suggesting very similar efficiencies in precipitating the THC acid present in the plant extract.

Example 5

The THCA-amine salts produced in Example 4 were characterized by taking their $^1$H NMR spectra in CDCl$_3$ solvent and recorded with a spectrometer at 400 MHz. Six key peaks of the THC carboxylate portion (see structure A), are reported starting with the most deshielded peak due to 1H followed by 2H, continuing with peaks due to and ending with peaks to the methyl groups 3, 4, 5, and 6. The first five peaks were singlets with relative integration 1:1:3:3:3. The last reported peak integrating for 3H, is a triplet due to the terminal methyl group of the C5 side chain. Key peaks due to the ammonium ion were also identified and listed in order of increasing field strength. The relative integration of the peaks due to specific hydrogens in the THCA carboxylate and the ammonium ion indicate a 1:1 ratio of the two species (structure 14):

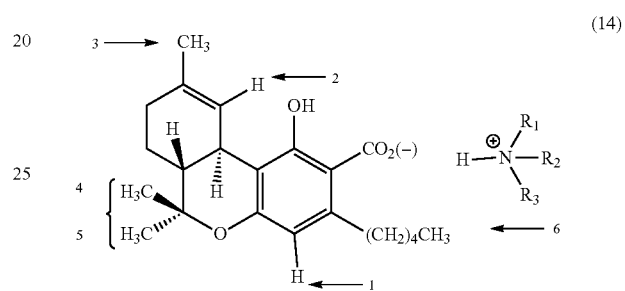

(14)

1. THCA-1,8-diazabicyclo[5.4.0]undec-7-ene salt (DBU)

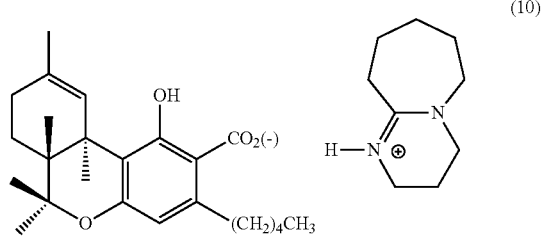

(10)

$^1$H NMR (400 Hz, CDCl$_3$) THC carboxylate. δ: 6.53, 6.06, 1.62, 1.38, 1.06, 0.82
Ammonium ion δ: 3.45 (t, 2H), 3.36 (m, 6H)

2. THCA-1,5-diazabicyclo[4.3.0]non-5-ene salt (DBN)

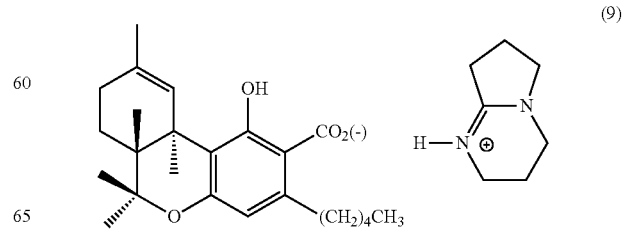

(9)

¹H NMR (400 Hz, CDCl₃) THC carboxylate. δ: 6.52, 6.06, 1.62, 1.38, 1.05, 0.83

Ammonium ion δ: 3.70 (m, 4H), 3.35 (t, 2H), 1.08 (t, 2H)

3. THCA-1,4-diazobicylcooctane salt (DABCO)

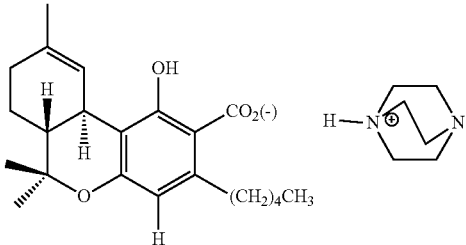
(8)

¹H NMR (400 Hz, CDCl₃) THC carboxylate. δ: 6.47, 6.11, 1.63, 1.38, 1.06, 0.85

Ammonium ion δ: 3.04 (s, 12H, CH₂-N+)

4. THCA-N-ethyldiisiopropylamine salt (Hunig's Base)

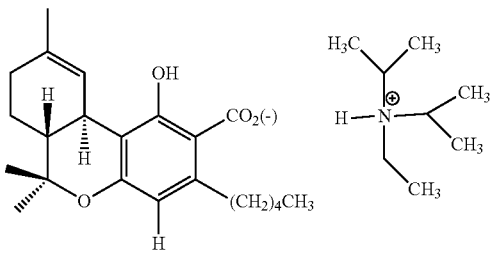
(7)

¹H NMR (400 Hz, CDCl₃) THC carboxylate. δ: 6.5, 6.08, 1.63, 1.38, 1.06, 0.83

Ammonium ion δ: 3.64 (m, 2H, N—CH(CH₃)₂), 3.04 (q, 2H, N—CH₂—CH₃)

5. THCA-piperidineethanol salt

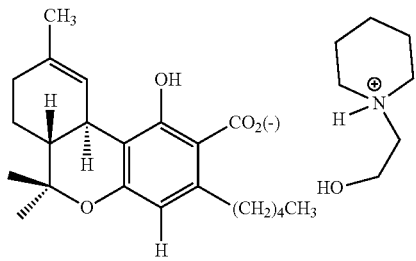
(5)

¹H NMR (400 Hz, CDCl₃) THC carboxylate. δ: 6.48, 6.11, 1.63, 1.39, 1.06, 0.84

Ammonium ion δ: 3.92 (m, 2H, CH₂—OH), 3.03 (m, 2H, CH₂—N)

6. THCA-dicyclohexylamine salt

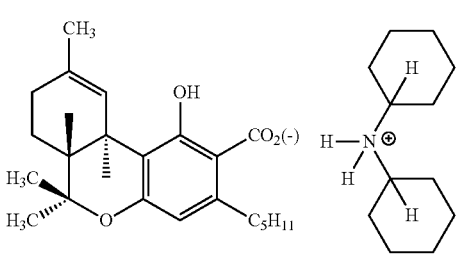
(13)

¹H NMR (400 Hz, CDCl₃) THC carboxylate. δ: 6.49, 6.13, 1.65, 1.40, 1.08, 0.86

Ammonium ion δ: 2.98 (m, 2H, N—CH)

7. THCA-dimethylethanolamine salt (DMEA)

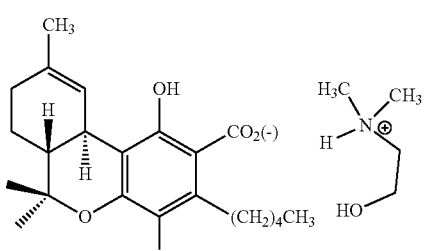
(4)

¹H NMR (400 Hz, CDCl₃) THC carboxylate. δ: 6.46, 6.12, 1.64, 1.39, 1.06, 0.84

Ammonium ion δ: 3.91 (m, 2H, CH₂—OH), 3.08 (m, 2H, CH₂—N), 2.75 (s, 6H, N—CH₃)

8. THCA-triethylamine salt

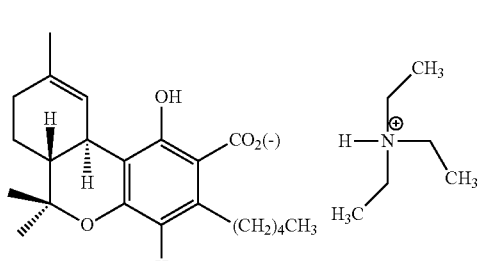
(6)

¹H NMR (400 Hz, CDCl₃) THC carboxylate. δ: 6.52, 6.09, 1.63, 1.38, 1.06, 0.84

Amine δ: 3.05 (q, 6H, N—CH₂), 1.28 (t, 9H, CH₂—CH₃)

9. THCA-quinine salt

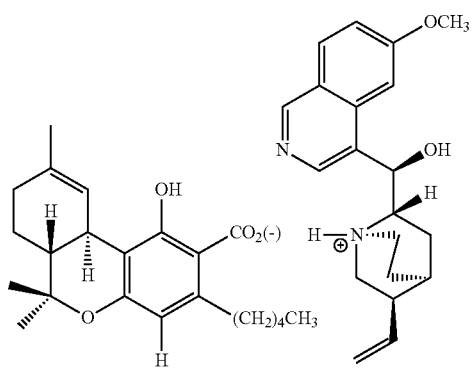

$^1$H NMR (400 Hz, CDCl$_3$) THC carboxylate. δ: 6.45, 6.13, 1.60, 1.30, 1.05, 0.76

Ammonium ion δ: [5 aromatic H: 8.64 (d, 1H), 7.93 (d, 1H), 7.55 (d, 1), 7.57 (s, 1H), 7.12 (d, 1H)], 3.73 (s, 3H, OCH$_3$)

NOTE the initial NMR analysis showed that the precipitated TCHA-quinine salt produced in Example 4 was a mixture of THCA-quinine salt and quinine. The salt was resolubilized in warmed ethyl acetate and then recrystallized by the addition of hexane to produce a solid THCA-quinine salt.

10. THCA-tetramethylethylenediamine salt (TMEDA)

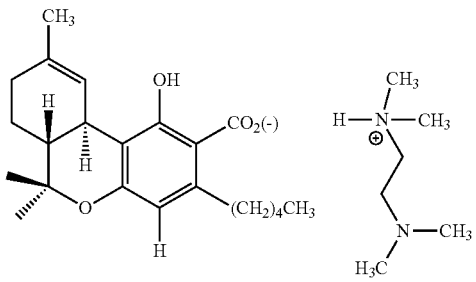

$^1$H NMR (400 Hz, CDCl$_3$) THC carboxylate. δ: 6.49, 6.11, 1.64, 1.39, 1.06, 0.85

Amine δ: 2.81 (s, 4H, N—CH$_2$—CH$_2$—N), 2.47 (s, 12H, N—CH$_3$)

Example 6

Figure 8:
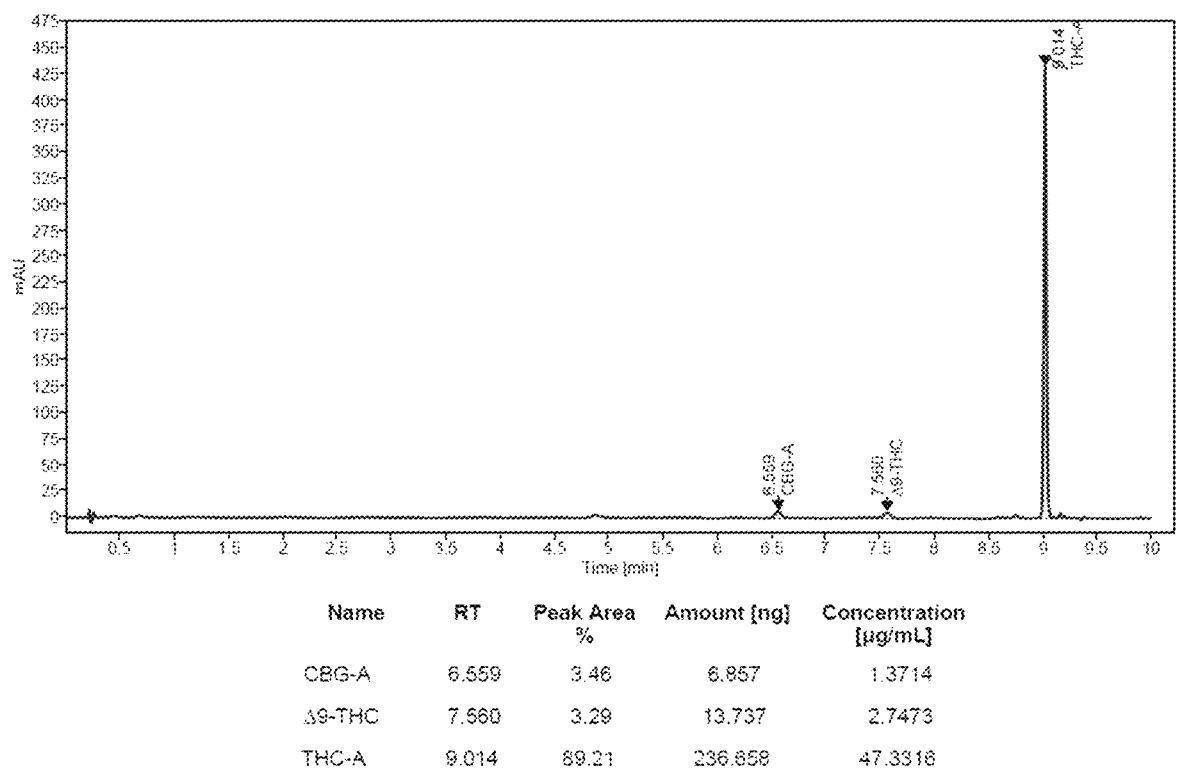
FIG. 8 is an HPLC chromatogram of a crude THCA stock solution prepared for Example 6.

This study further assessed the ability of six selected amines to precipitate THCA-amine salts from a crude extract recovered from *C. sativa* finely ground flower buds with heptane solvent. The crude extract was adjusted with additional heptane to provide a crude THCA stock solution containing 47.332 mg/mL THCA. HPLC analysis indicated that the crude THCA stock solution also contained small amounts of CBGA and Δ$^9$-THC (FIG. 8).

The following amines were assessed in this study:

| | |
|---|---|
| 1. | TMEDA |
| 2. | DABCO |
| 3. | DBN |
| 4. | DBU |
| 5. | 1-piperidineethanol |
| 6. | quinine |

Figure 9A:
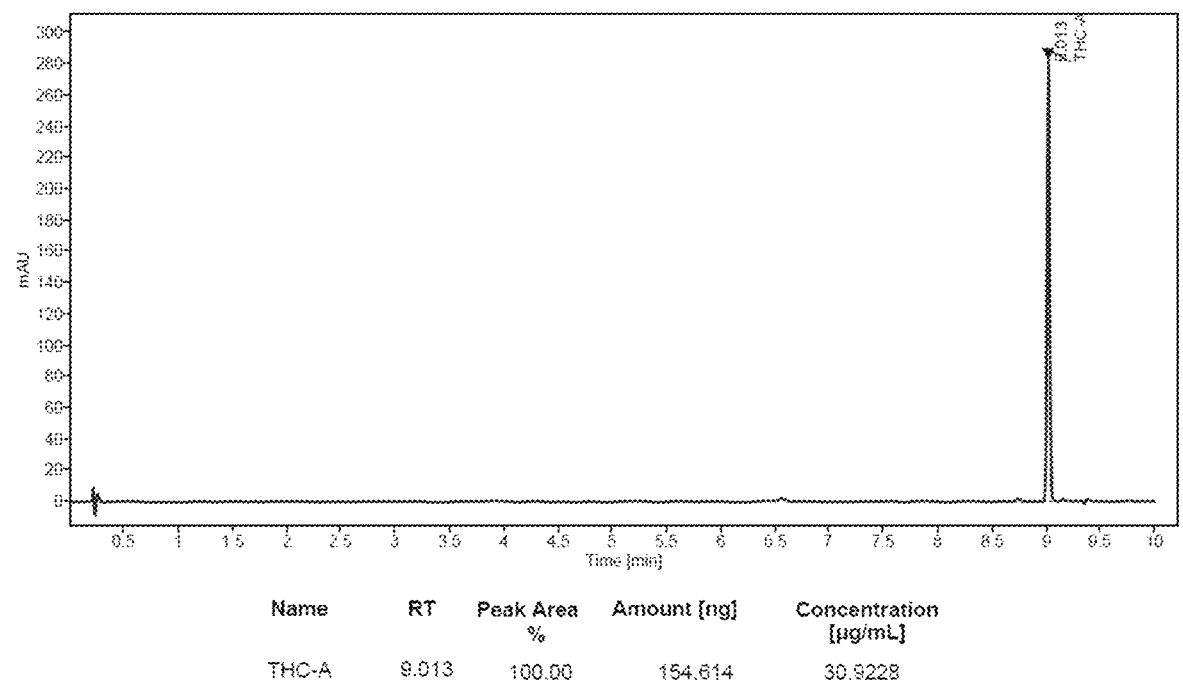
FIG. 9A is an HPLC chromatogram of a washed crude THCA-TMEDA salt prepared from the crude THCA stock solution shown in FIG. 8.
Figure 9B:
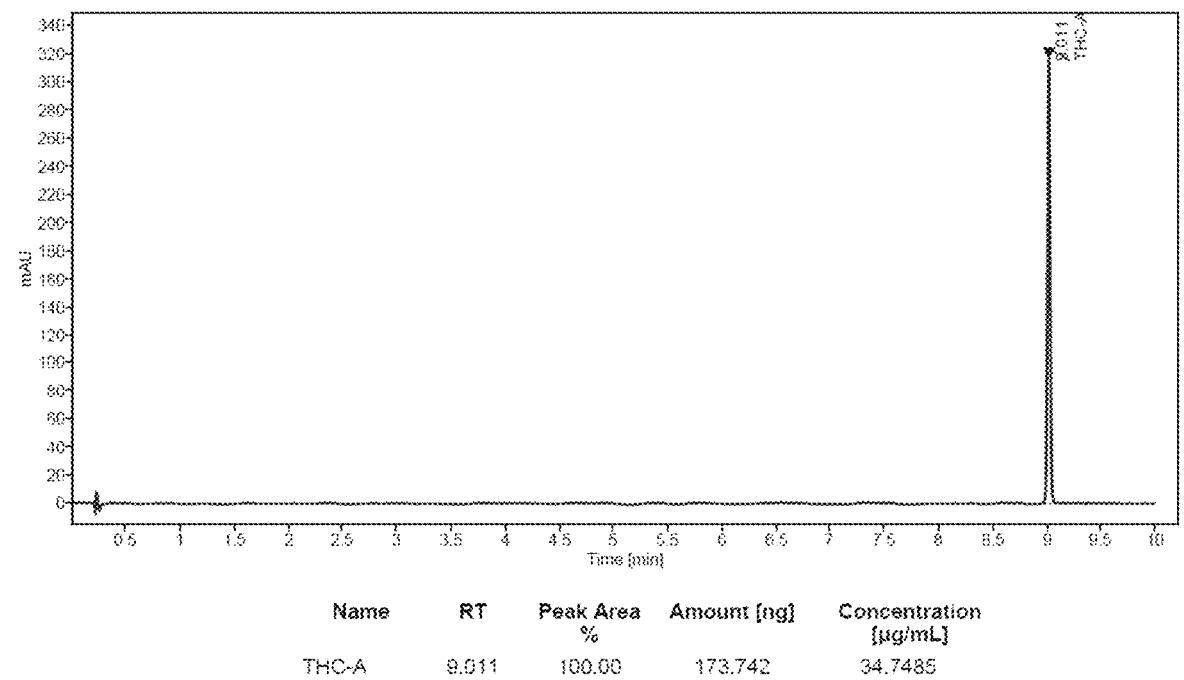
FIG. 9B is an HPLC chromatogram of a purified THCA-TMEDA salt recrystallized from the crude salt shown in FIG. 9A.
Figure 10A:
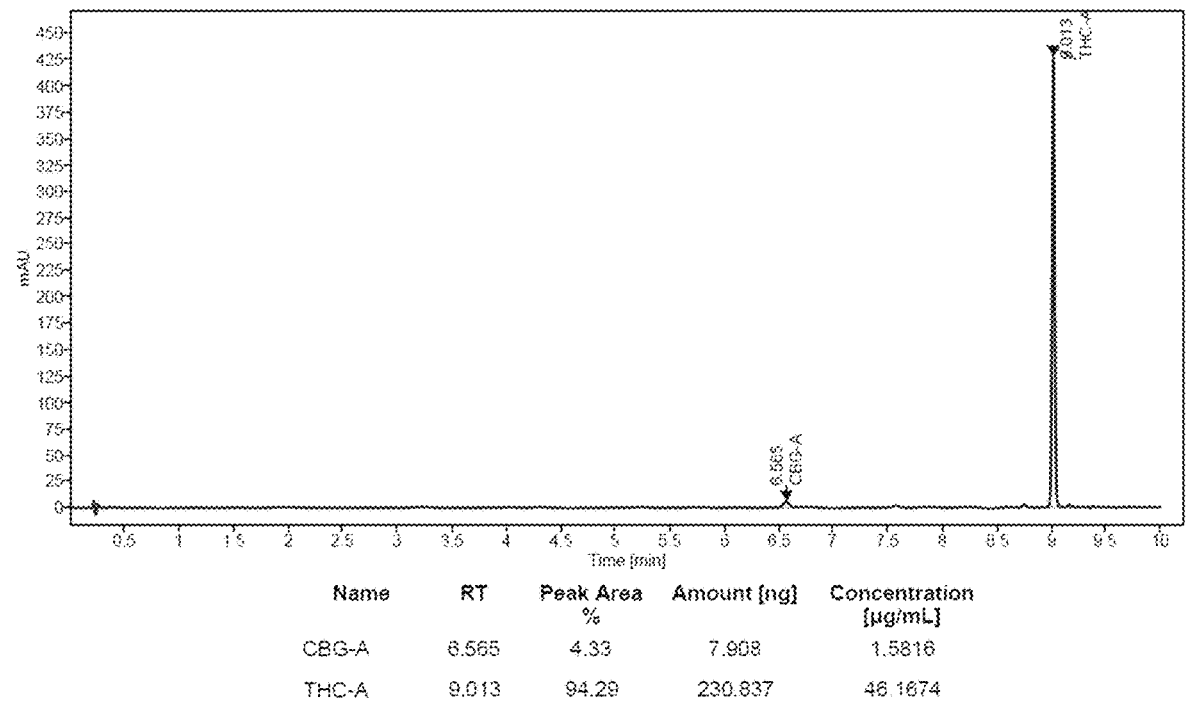
FIG. 10A is an HPLC chromatogram of a washed crude THCA-DABCO salt prepared from the crude THCA stock solution shown in FIG. 8.
Figure 11A:
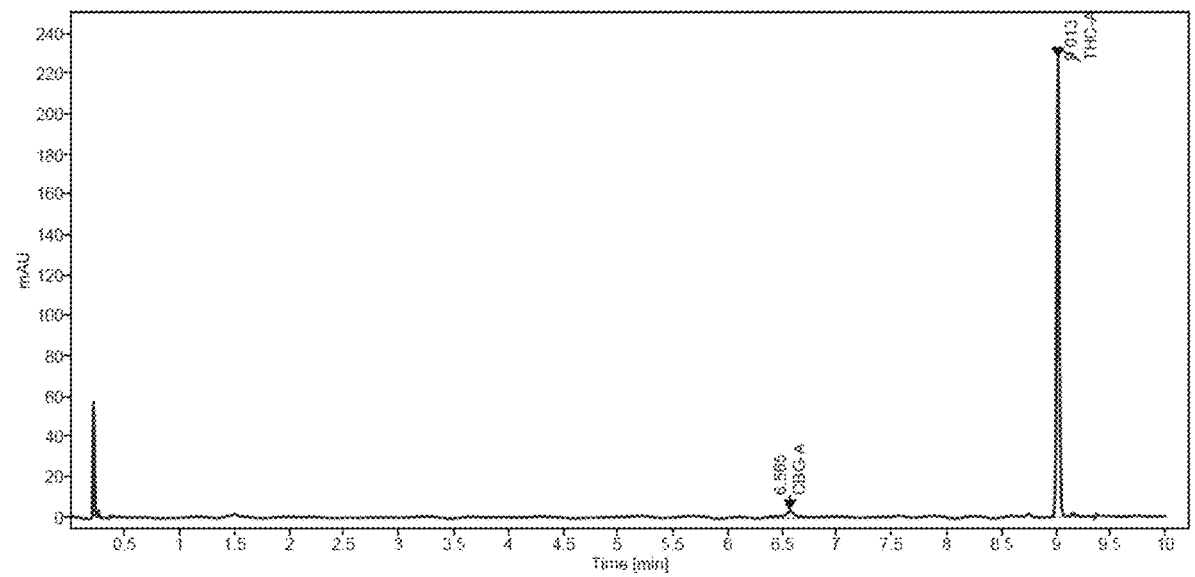
FIG. 11A is an HPLC chromatogram of a washed crude THCA-DBN salt prepared from the crude THCA stock solution shown in FIG. 8.
Figure 12A:
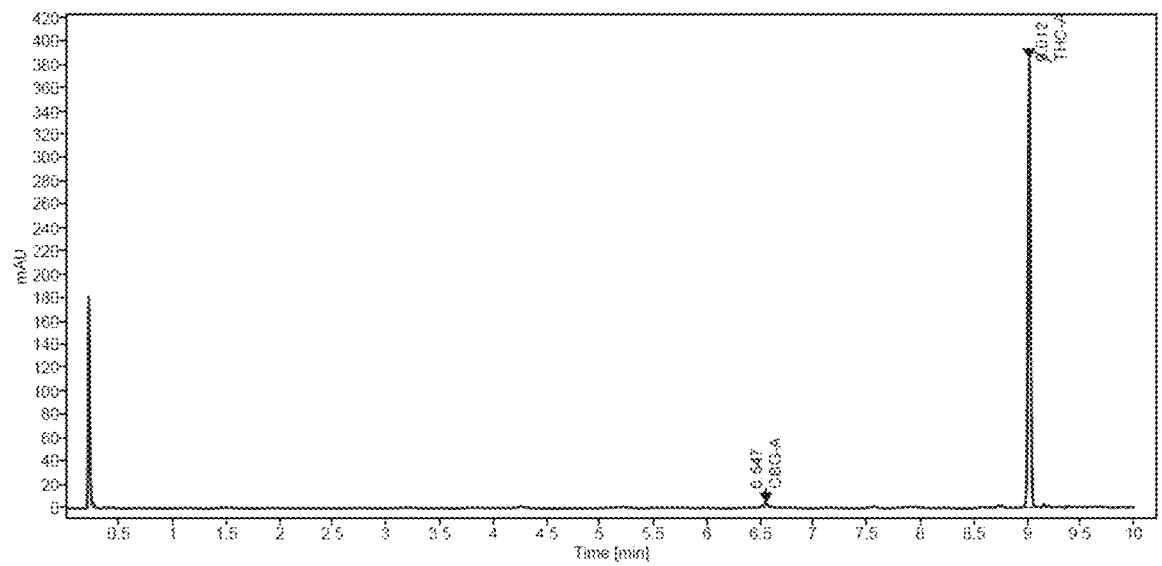
FIG. 12A is an HPLC chromatogram of a washed crude THCA-DBU salt prepared from the crude THCA stock solution shown in FIG. 8.
Figure 13A:
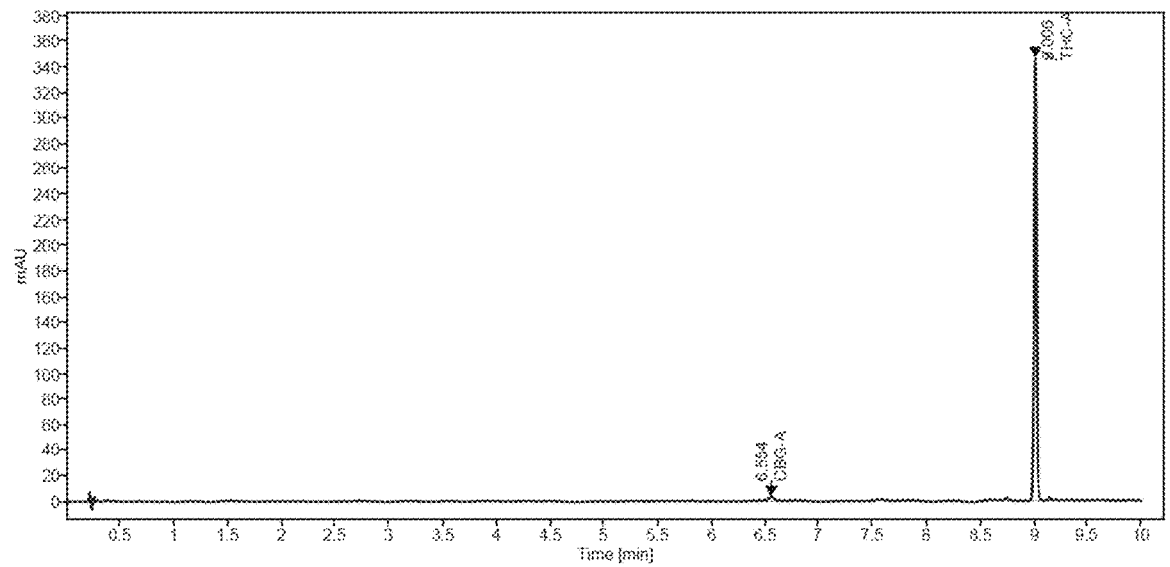
FIG. 13A is an HPLC chromatogram of a washed crude THCA-piperidineethanol salt.
Figure 14A:
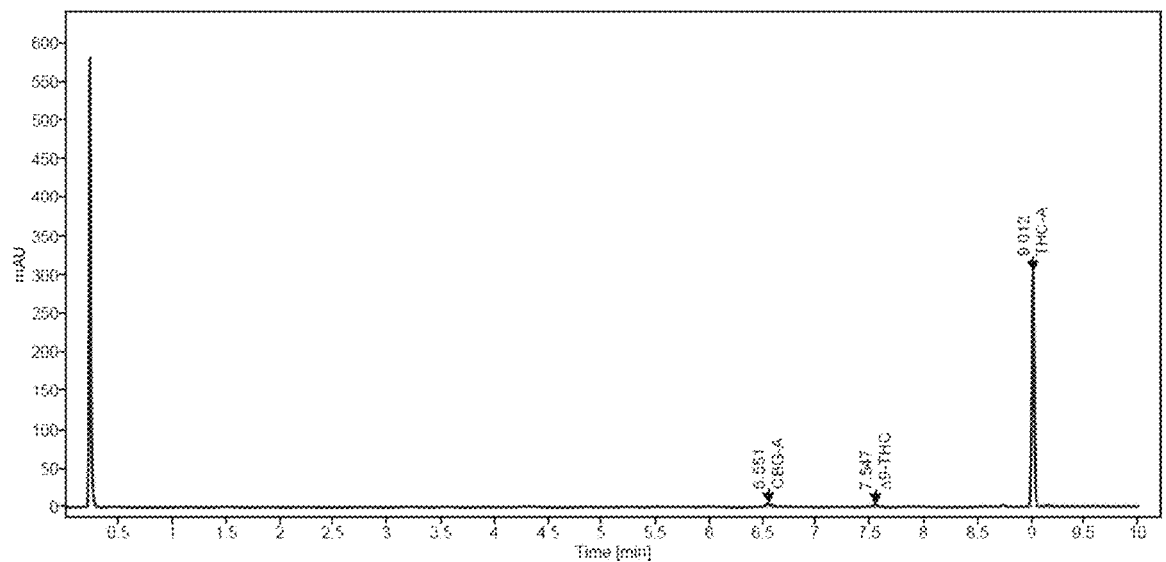
FIG. 14A is an HPLC chromatogram of a washed crude THCA-quinine salt prepared from the crude THCA stock solution shown in FIG. 8.

A 3:1 molar ratio of each amine was added dropwise to duplicate 35-mL volumes of the crude THCA stock solution while mixing by sonication to thereby cause precipitation of a solid crude THCA-amine salt. Each of the amines assessed was dissolved in heptane prior to addition to the crude THCA stock solutions with the exception of DABCO which was solubilized in ethyl acetate and quinine which was solubilized in dichloromethane. Each 35-ml volume of the crude THCA stock solution contained 1.656 g of THCA. Precipitation was encouraged by cooling each reaction mixture to −20° C. for 1-24 hours. The precipitated solid THCA-amine salts formed in each 35-mL volume were separated from the liquid phase by vacuum filtration, washed with 40 mL cold heptane, dried under vacuum (Table 12), and then analyzed by HPLC (FIG. 9A, crude THCA-TMEDA salt; FIG. 10A, crude THCA-DABCO salt; FIG. 11A, crude THCA-DBN salt; FIG. 12A, crude THCA-DBU salt; FIG. 13A, crude THCA-piperidineethanol salt; FIG. 14A, crude THCA-quinine salt).

TABLE 12

| Amine | THCA mass in crude stock (g) | Mass of amine (g) | Crude THCA-amine salt (g) | Purified THCA-amine salt (g) |
|---|---|---|---|---|
| TMEDA | 3.313 | 3.070 | 4.756 | 2.142 |
| DABCO | 3.313 | 3.000 | 4.886 | 2.809 |
| DBN | 3.313 | 3.300 | 7.444 | 5.439 |
| DBU | 3.313 | 4.030 | 6.990 | 3.269 |
| PiperidineEtOH | 3.313 | 3.500 | 5.204 | 3.522 |
| Quinine | 3.313 | 4.380 | 6.941 | 5.323 |

Figure 10B:
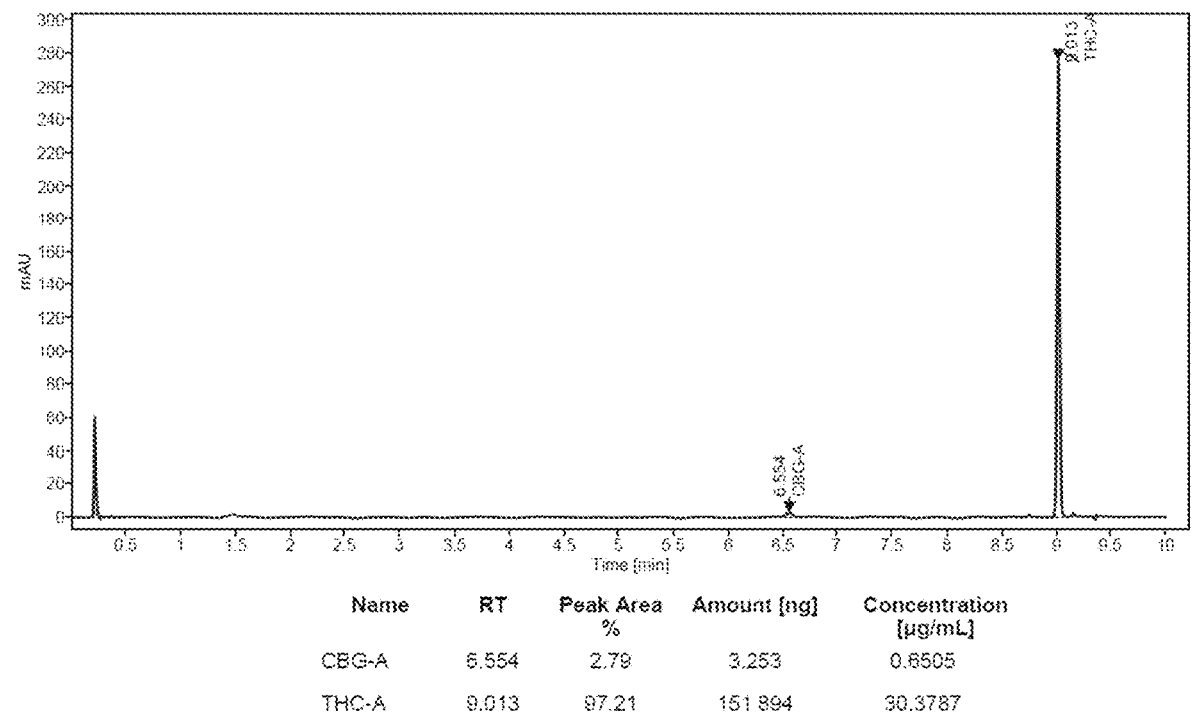
FIG. 10B is an HPLC chromatogram of a purified THCA-DABCO salt recrystallized from the crude salt shown in FIG. 10A.
Figure 11B:
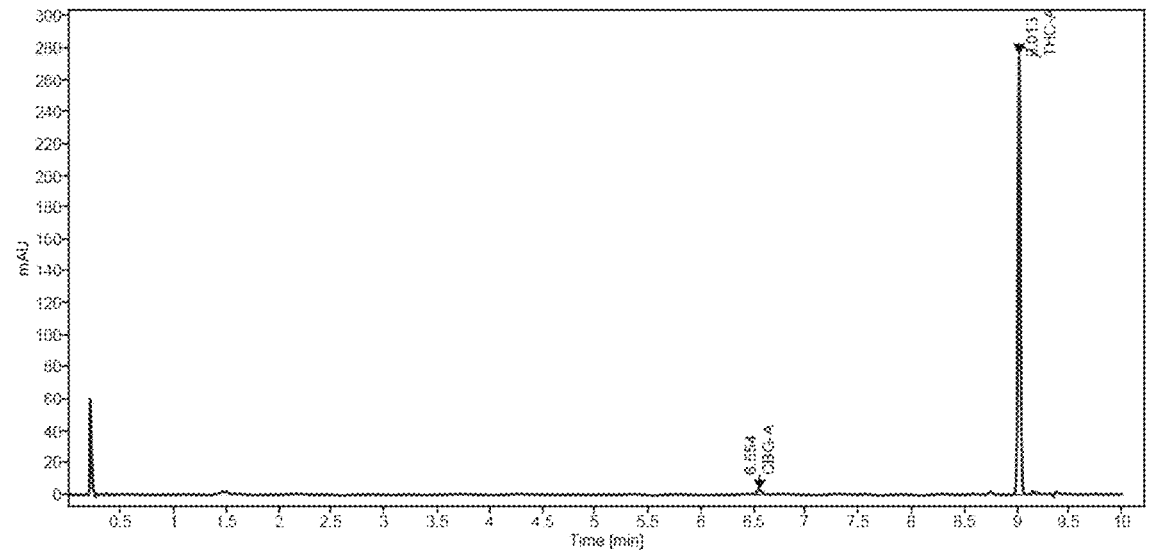
FIG. 11B is an HPLC chromatogram of a purified THCA-DBN salt recrystallized from the crude salt shown in FIG. 11A.
Figure 12B:
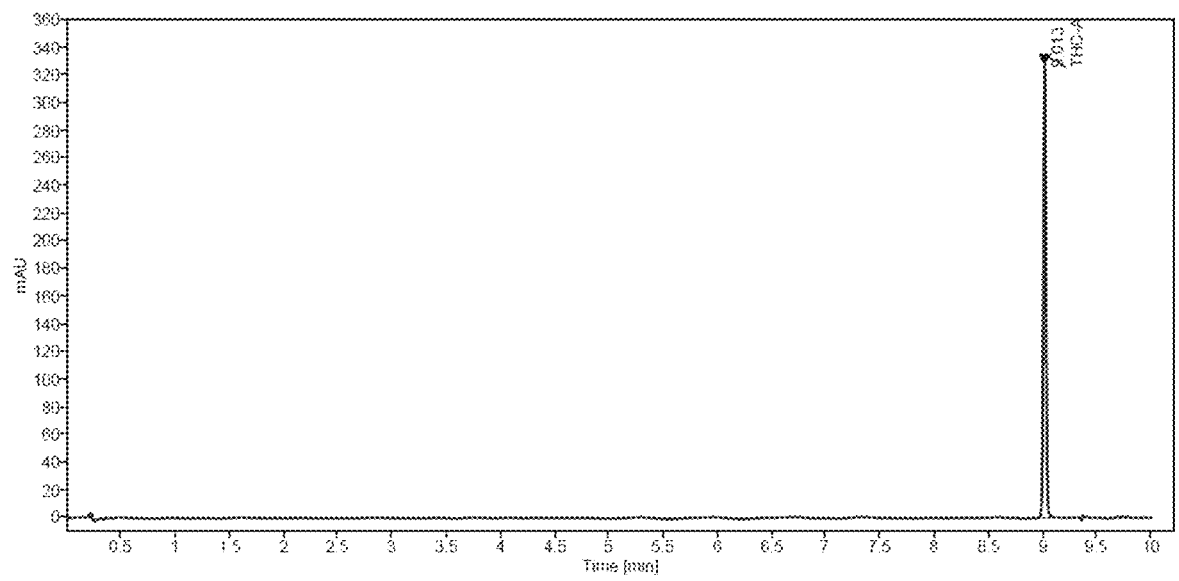
FIG. 12B is an HPLC chromatogram of a purified THCA-DBU salt recrystallized from the crude salt shown in FIG. 12A.
Figure 13B:
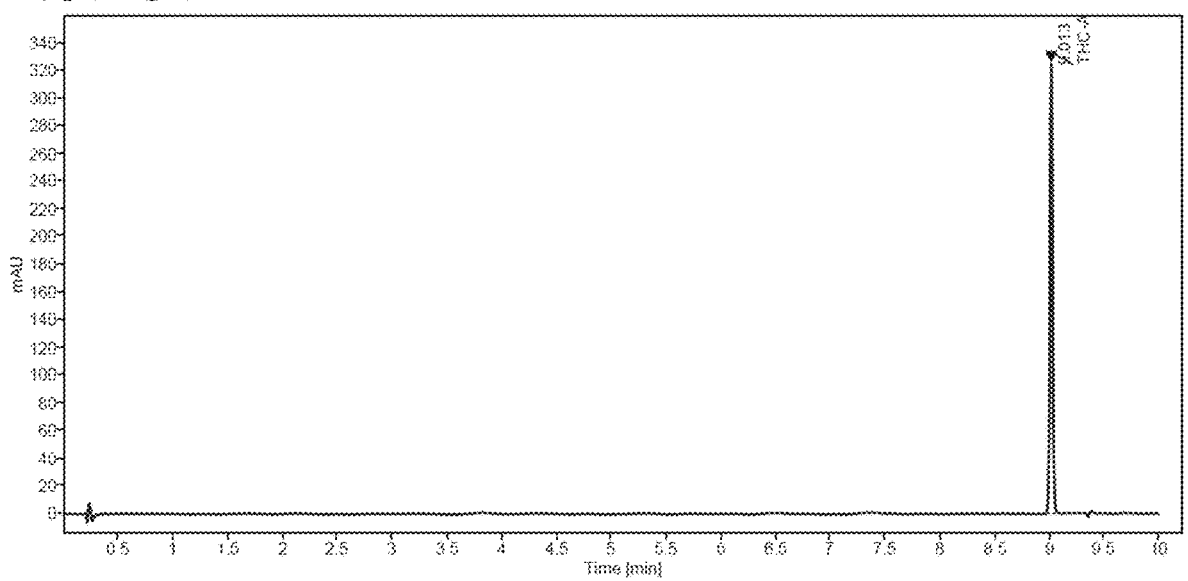
FIG. 13B is an HPLC chromatogram of a purified THCA-piperidineethanol salt recrystallized from the crude salt shown in FIG. 13A.
Figure 14B:
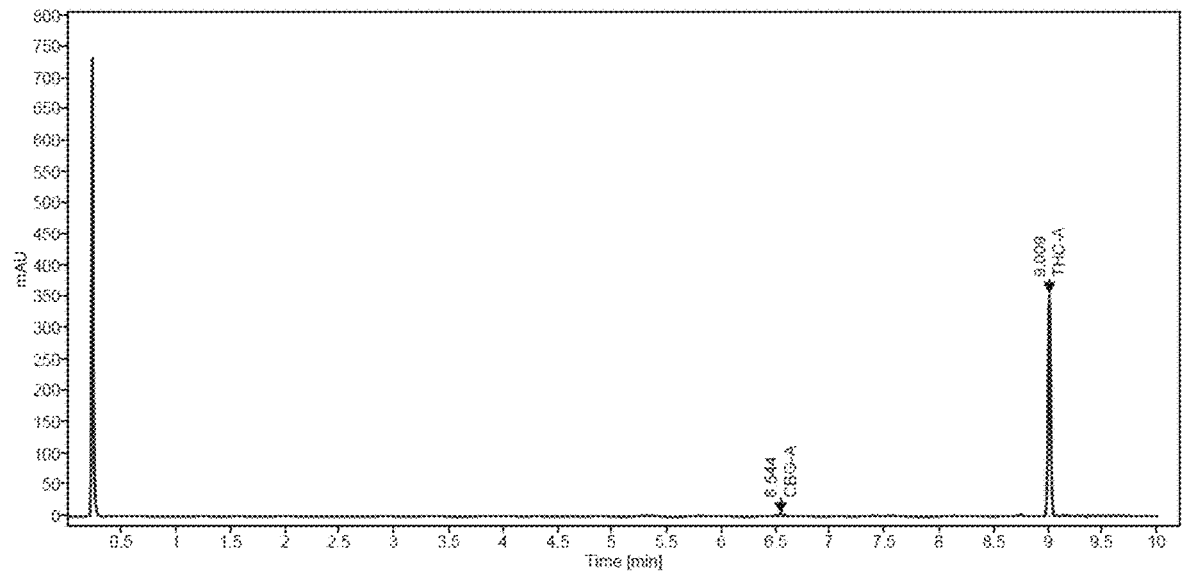
FIG. 14B is an HPLC chromatogram of a purified THCA-quinine salt recrystallized from the crude salt shown in FIG. 14A.

The duplicate solid THCA-amine salt samples precipitated from the two 35-mL volumes of stock solution with each amine, were combined and then dissolved in 5-40 mL ethyl acetate under refluxing conditions until dissolution was complete. The dissolved THCA-amine salts were recrystallized by cooling the solution under ambient conditions to about 30° C. The recrystallizing THCA-amine solutions were then cooled at 4° C. for about 2 hr, and then stored at −20° C. for 12-18 hr to complete the recrystallization processes. Each of the recrystallized purified THCA-amine salts was then separated from their liquid phases by vacuum filtration, washed with 40 mL of cold heptane, dried under vacuum (Table 12), and then analyzed by HPLC (9B, purified THCA-TMEDA salt; FIG. 10B, purified THCA-DABCO salt; FIG. 11B, purified THCA-DBN salt; FIG. 12B, purified THCA-DBU salt; FIG. 13B, purified THCA-piperidineethanol salt; FIG. 14B, purified THCA-quinine salt).

In summary, all six amines assessed in this study produced highly purified THCA-amine salts. TMEDA, DBU, and piperidineethanol produced 100% pure THCA-amine salts.

Example 7

Portions of the six purified THCA-amine salts produced in the study disclosed in in Example 6 were further processed to produce highly purified $\Delta^9$-THC. First, each of the THCA-amine salts was decarboxylated by addition into and commingling with a 2.5% $Na_3CO_2$ solution at a 10:1 volume/mass ratio followed by heating of the reaction mixture at refluxing conditions (about 100° C.±3° C.) for 4 hrs. The resulting biphasic solution consisting of an upper organic oil layer and lower aqueous layer was cooled to 70° C. and then, the upper organic layer was solubilized with a 1:1 v/v ratio of heptane to $Na_3CO_2$ solution. The organic upper organic layer was separated from the aqueous layer and then, the organic layer was washed twice with a 1:1 v/v ratio of 5% HCl and dried over magnesium sulfate. The heptane was then removed from the organic layer by distillation to thereby produce an oil containing highly purified $\Delta^9$-THC (Table 13).

TABLE 13

| THCA-amine salt | Purified THCA-amine salt (g) | Mass of decarboxylated $\Delta^9$-THC oil (g) | Purified peak area % |
|---|---|---|---|
| THCA-TMEDA salt | 1.922 | 1.481 | 98.1% |
| THCA-DABCO salt | 2.766 | 1.683 | 90.1% |
| THCA-DBN salt | 5.439 | 1.783 | 71.1% |
| THCA-DBU salt | 3.265 | 0.352 | 65.2% |
| THCA-piperidineethanol salt | 2.329 | 2.101 | 81.0% |
| THCA-quinine salt | 5.147 | 0.193 | 82.8% |

Example 8

Figure 15A:
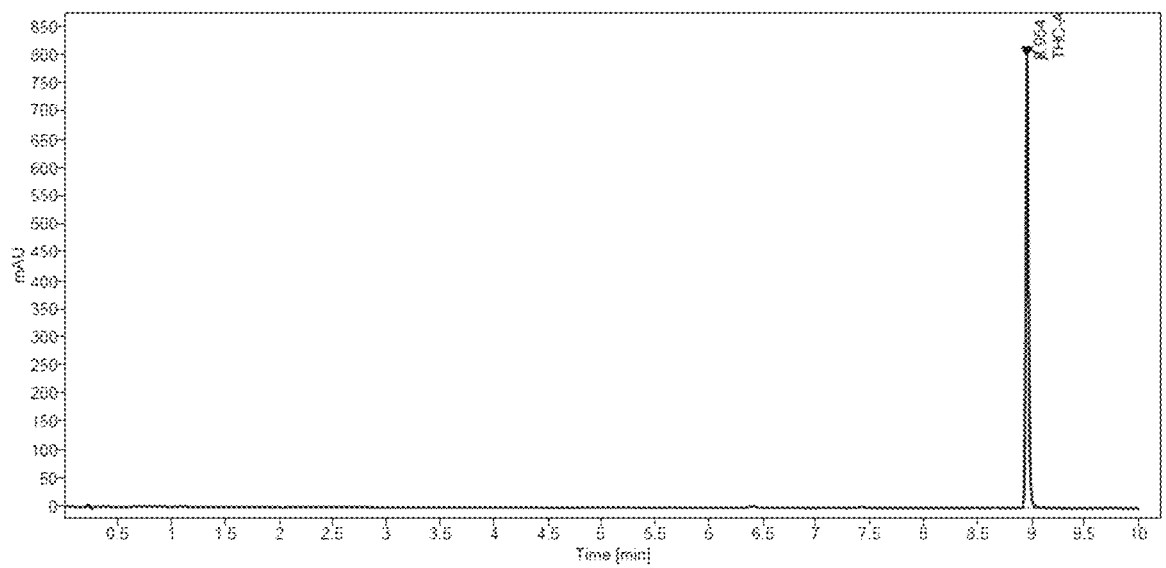
FIG. 15A is an HPLC chromatogram of a purified THCA-DMEA from Example 8.
Figure 15B:
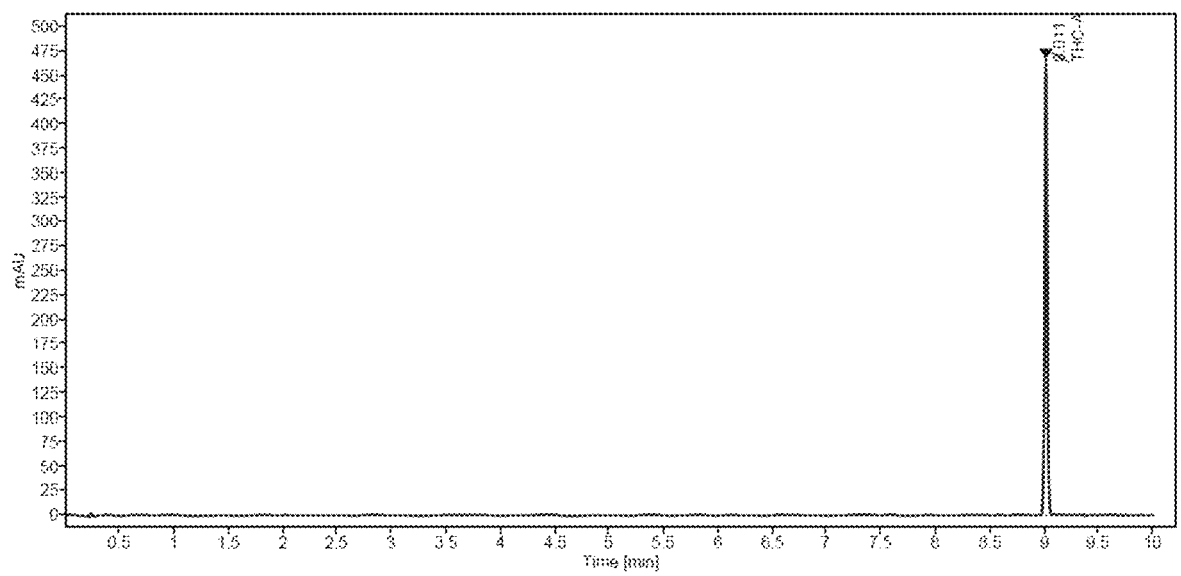
FIG. 15B is an HPLC chromatogram of a highly pure crystalline THCA recovered from the purified THCA-DMEA salt shown in FIG. 15A.

This study assessed separation and recovery of highly purified crystalline THCA from a purified THCA-DMEA salt. 4.74 g of recrystallized purified THCA-DMEA salt (FIG. 15A) was dissolved in 24 mL of dichloromethane at ambient temperature at a ratio of 1:6 mass/volume. The THCA-DMEA salt solution was acidified by the addition of 2.5 mL of a 5% HCl solution and thoroughly mixed in a separatory funnel thereby partitioning the mixture into an upper organic layer and a lower aqueous layer. The aqueous layer containing the DMEA-hydrochloride was separated from the organic layer containing the THCA. The organic layer was dried over magnesium sulfate and then was gravity filtered. The dichloromethane was removed by distillation to yield 3.44 g of a crystalline THCA (FIG. 15B).

Example 9

Figure 16A:
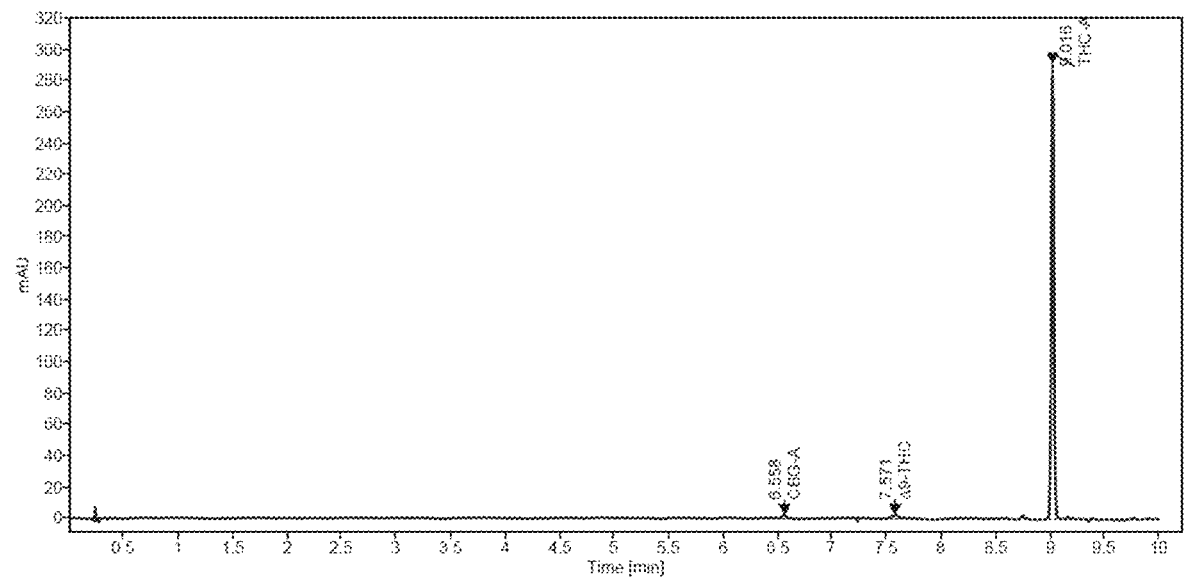
FIG. 16A is an HPLC chromatogram showing separation of cannabinoids present in a standardized solvent-solubilized C. sativa extract prepared for assessment of the effects of spiking with denatured ethanol in Example 9.

This study assessed the effects of spiking a standardized solvent solubilized crude C. sativa extract on the precipitation of a THCA-amine salt from the extract. A 170-mL solution of a C. sativa extract in heptane, was prepared and standardized to contain 31.940 mg/mL THCA (FIG. 16A; 20-uL sample volume). 10-mL aliquots of the standardized solution were spiked with 0 mL (control), 0.350 mL, or 0.525 mL of denatured ethanol (84.15% v/v ethanol, 15% v/v methanol, 0.85% v/v ethyl acetate). Next a 3:1 molar ratio of DMEA (0.292 mL) was added to each of the four extract solutions, and the mixtures were vortexed for 10 seconds thereby producing crude THCA-DMEA salts. Each salt was washed twice with 10 mL cold heptane, separated from the liquid phase by vacuum filtration, dried, and weighed (Table 14).

TABLE 14

| THCA mass (g) | DMEA vol. (mL) | THCA-DMEA salt (g) | Precipitate yield (%) |
|---|---|---|---|
| 0.319 | 0 | 0.518 | 98.8% |
| 0.319 | 0.350 | 0.472 | 97.6% |
| 0.319 | 0.525 | 0.444 | 94.3% |

Figure 16B:
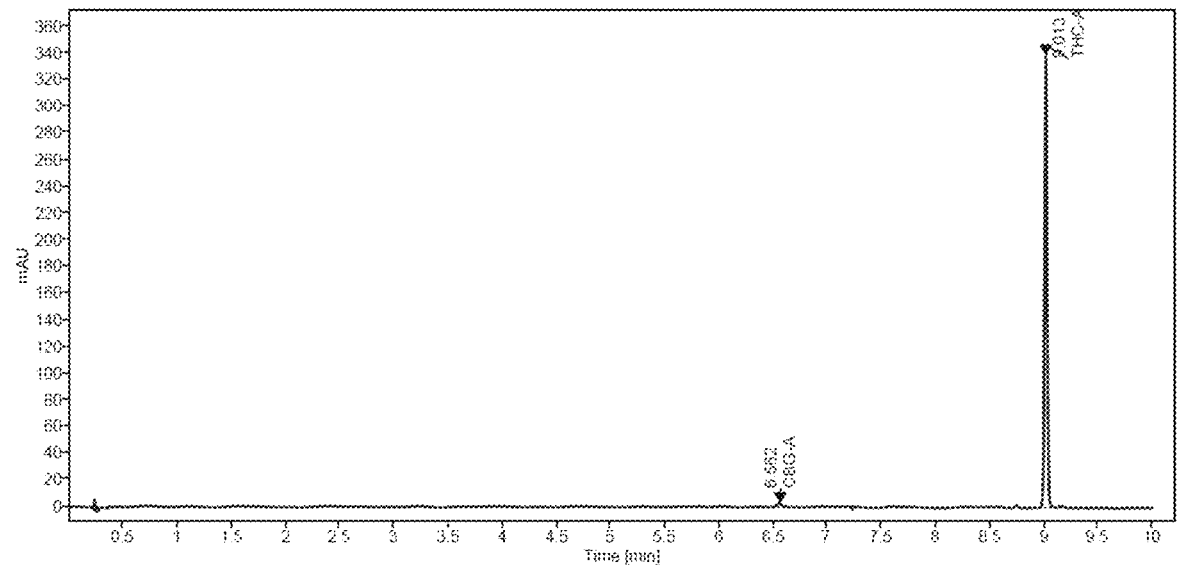
FIG. 16B is an HPLC chromatogram of a washed crude THCA-DMEA salt recovered from the standardized solvent-solubilized C. sativa extract shown in FIG. 16A.
Figure 16C:
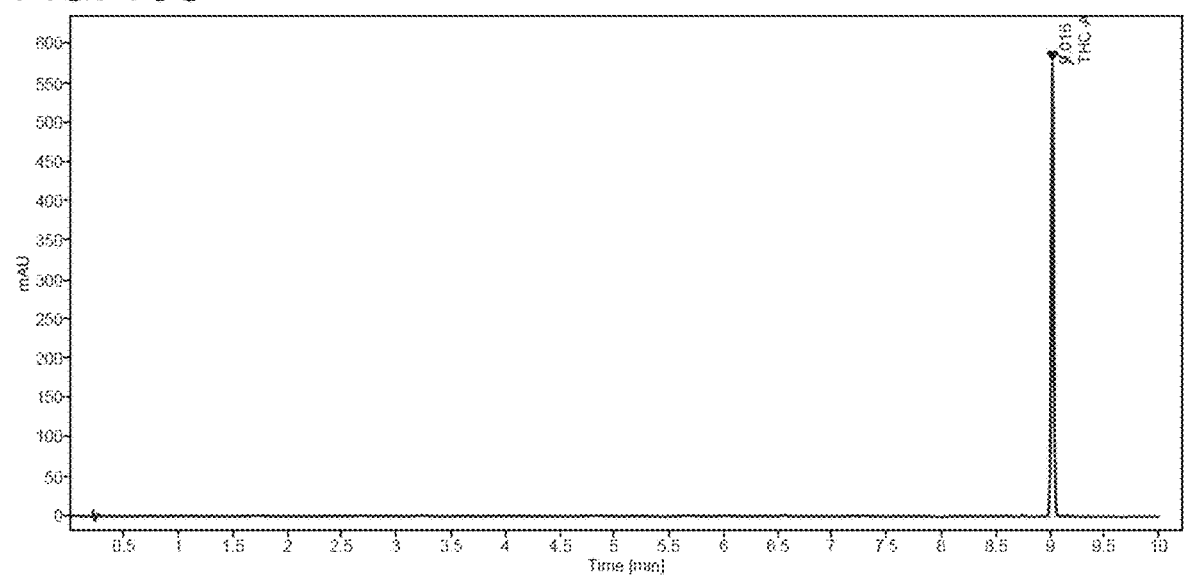
FIG. 16C is an HPLC chromatogram showing the effects of a 0.350-mL denatured alcohol spike prior to adding DMEA to the standardized solvent-solubilized C. sativa extract shown in FIG. 16A, on the separation of THCA-DMEA salt.
Figure 16D:
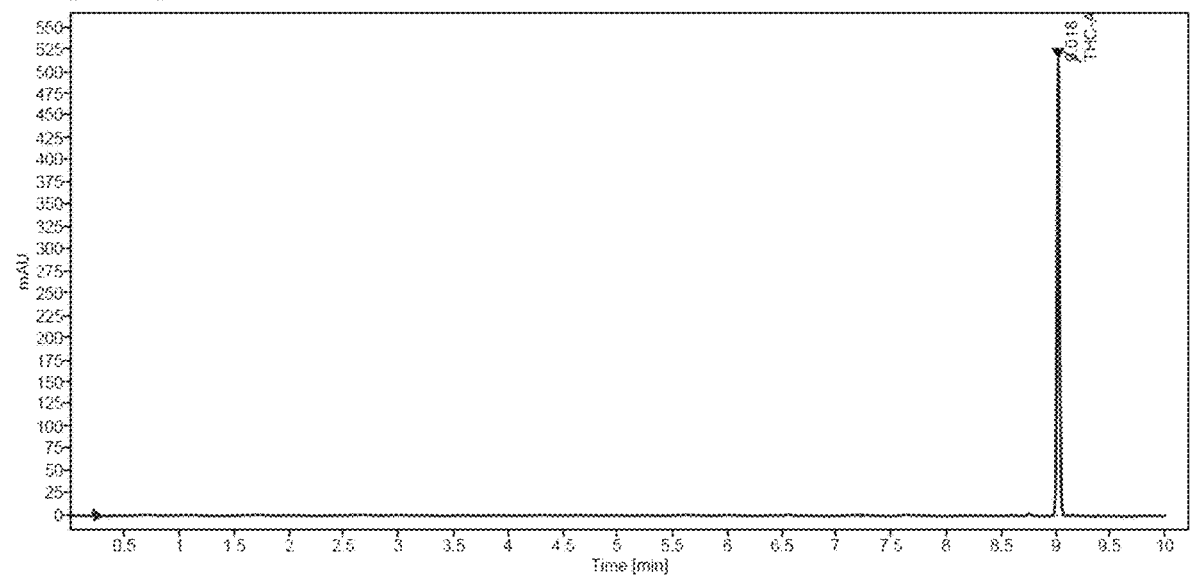
FIG. 16D is an HPLC chromatogram showing the effects of a 0.525-mL denatured alcohol spike prior to adding DMEA to the standardized solvent-solubilized C. sativa extract shown in FIG. 16A, on the separation of THCA-DMEA salt.

A sample of the each dried THCA-DMEA salt was solubilized in methanol and assayed by HPLC (FIG. 16B, control; FIG. 16C spiked with 0.350 mL denatured ethanol; FIG. 16D spiked with 0.525 mL denatured ethanol). The data in Table 14 indicate that although the THCA-DMEA salt yield decreased slightly as the amount of denatured ethanol spike was increased in this study, the data in FIGS. 16B-16D show that the purity of the precipitated THCA-DMEA increased as the amount of denatured ethanol spike was increased.

Example 10

Figure 17A:
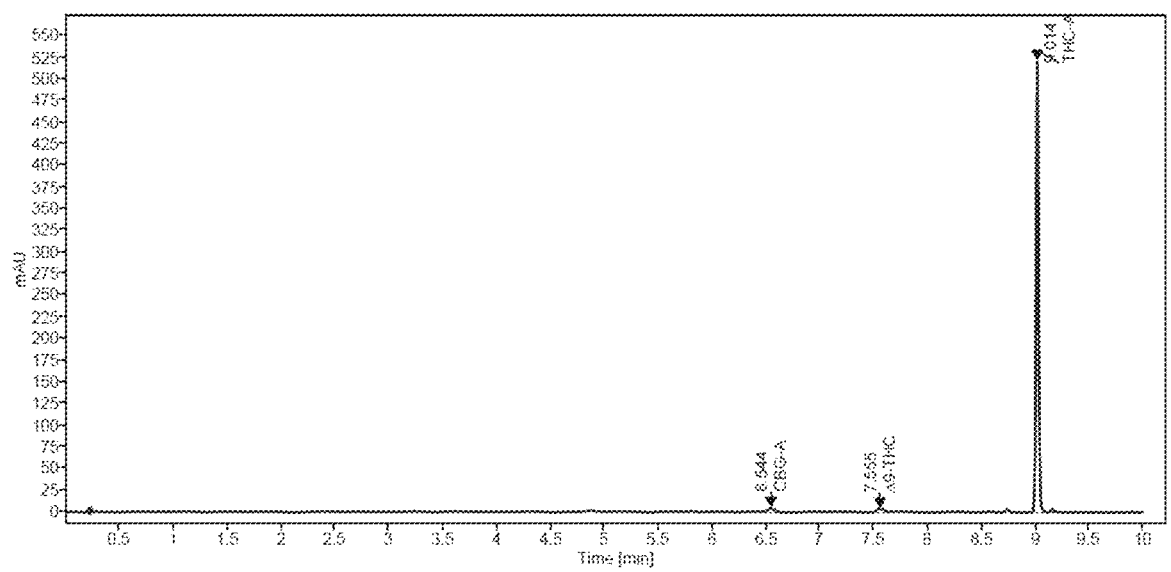
FIG. 17A is an HPLC chromatogram showing separation of cannabinoids present in a standardized solvent-solubilized C. sativa extract prepared for assessment of the effects of spiking with denatured ethanol in Example 10.

This study assessed the effects of spiking a standardized solvent solubilized crude C. sativa extract on the precipitation of a THCA-amine salt from the extract. A solution of C. sativa extract in heptane was prepared and standardized to contain 143.118 mg/mL THCA (FIG. 17A; 20-uL sample volume). 10-mL aliquots of the standardized solution were spiked with 0 mL (control) or 0.525 mL denatured ethanol (84.15% v/v ethanol, 15% v/v methanol, 0.85% v/v ethyl acetate). Next a 3:1 molar ratio of DMEA (1.10 mL) was added to each extract solution and the mixtures were vortexed for 10 seconds thereby producing crude THCA-DMEA salts. Each salt was washed twice with 10 mL cold heptane, separated from the liquid phase by vacuum filtration, dried, and weighed (Table 15).

TABLE 15

| THCA mass (g) | DMEA vol. (mL) | THCA-DMEA salt (g) | Precipitate yield (%) |
|---|---|---|---|
| 1.431 | 0 | 1.966 | 99.4% |
| 1.431 | 0.525 | 1.858 | 98.8% |

Figure 17B:
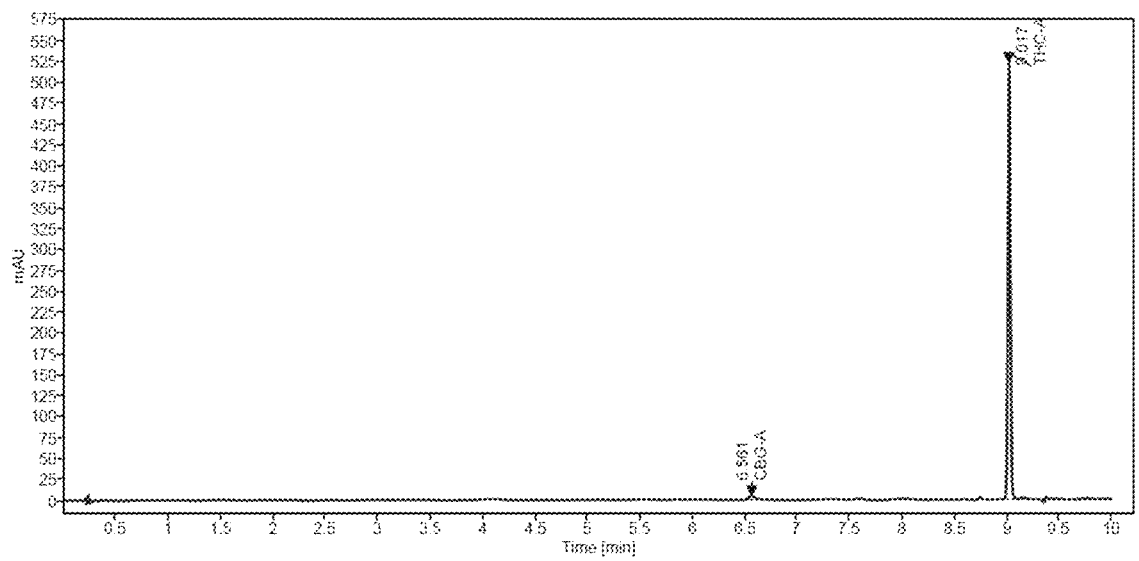
FIG. 17B is an HPLC chromatogram of a washed crude THCA-DMEA salt recovered from the standardized solvent-solubilized C. sativa extract shown in FIG. 17A.
Figure 17C:
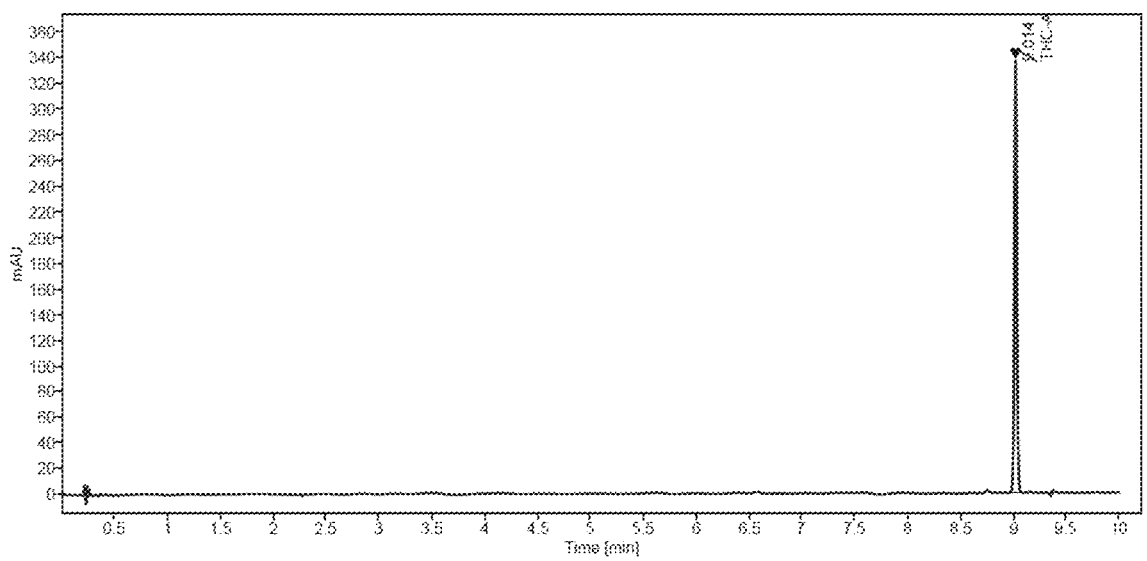
FIG. 17C is an HPLC chromatogram showing the effects of a 0.525-mL denatured alcohol spike prior to adding DMEA to the standardized solvent-solubilized C. sativa extract shown in FIG. 17A, on the separation of THCA-DMEA salt.

A sample of the each dried THCA-DMEA salt was solubilized in methanol and assayed by HPLC (FIG. 17B, control; FIG. 17C spiked with 0.525 mL denatured ethanol). The data in Table 14 indicate that while THCA-DMEA salt yield decreased slightly when the solvent-solubilized crude C. sativa extract was spiked with denatured ethanol, the data in FIG. 17C show that the purity of the precipitated THCA-DMEA was increased.

Example 11

Figure 18A:
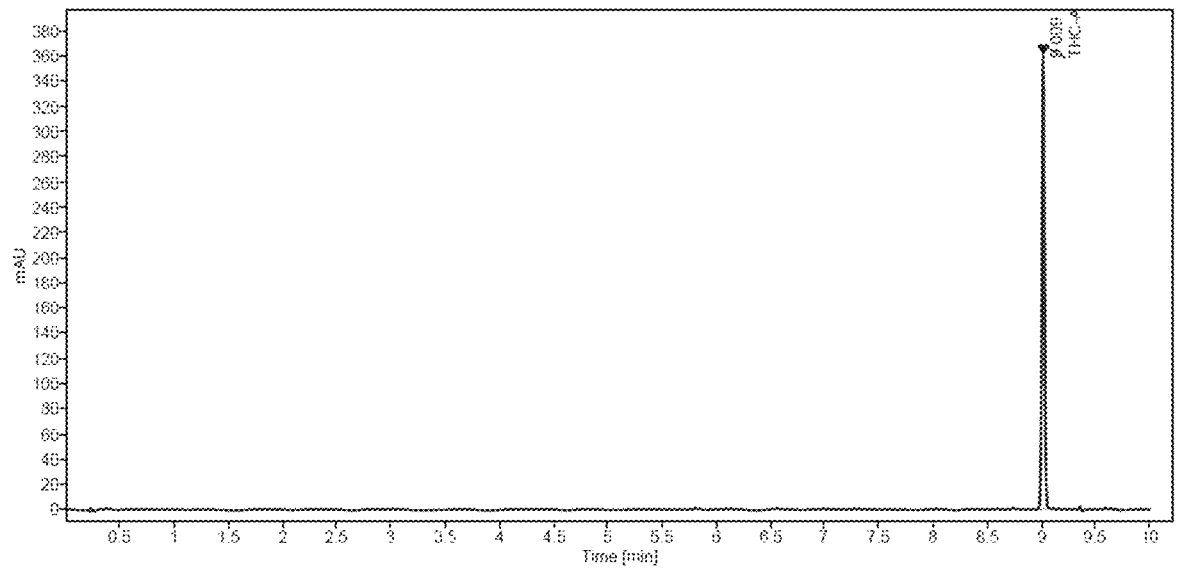
FIG. 18A is an HPLC chromatogram showing the composition of a purified THCA-DMEA salt used in Example 11.
Figure 18B:
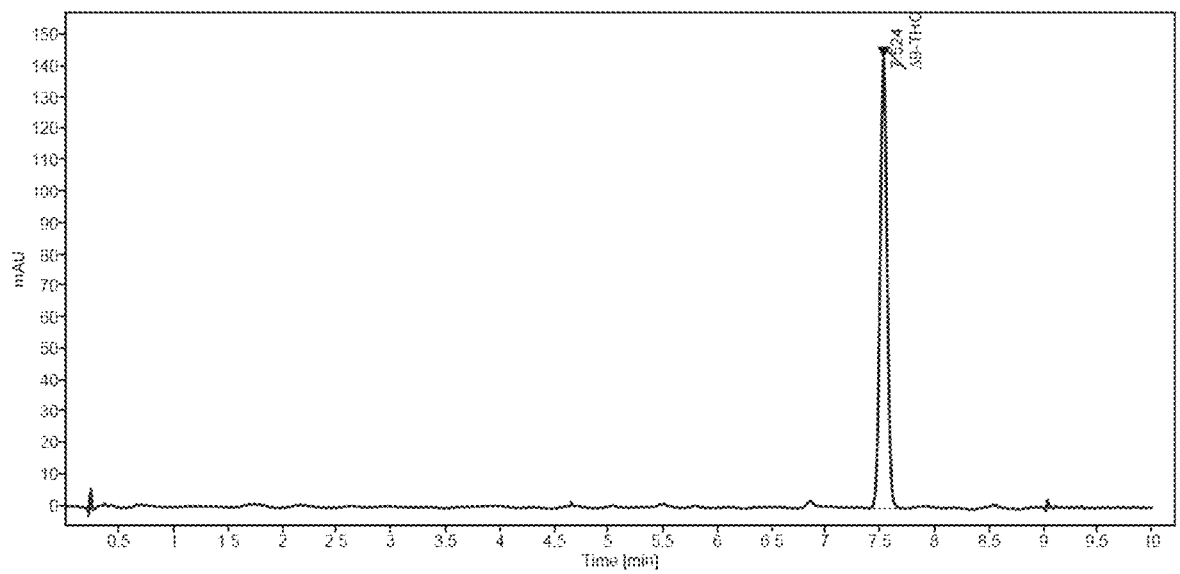
FIG. 18B is an HPLC chromatogram showing the composition of a purified $\Delta^9$-THC prepared from the THCA-DMEA salt shown in FIG. 18A.

5.0768 g of a recrystallized purified THCA-DMEA salt (FIG. 18A) were decarboxylated by the addition of a 2.5:1 volume mass of a 10% $Na_2CO_3$ solution (12.75 mL) followed by heating the reaction mixture to refluxing conditions (about 100° C.±3° C.) for about 4 hr. After the 4-hr decarboxylation period, the resulting biphasic solution consisting of an upper organic layer containing $\Delta^9$-THC and DMEA and a lower aqueous layer containing the $Na_2CO_3$ solution, was cooled to 70° C. after which, the organic layer was separated and recovered. 50 mL of heptane were added to the organic layer to dissolve the $\Delta^9$-THC and DMEA thereinto. The DMEA was separated from the $\Delta^9$-THC by the addition of a 5% HCl solution at a ratio of 1:1 (v/v) thereby producing a biphasic solution consisting of an upper organic layer containing therein $\Delta^9$-THC and a lower aqueous layer containing the DMEA. After separation, recovery, drying of the organic layer over magnesium sulfate, the heptane was removed by distillation thereby producing a highly purified $\Delta^9$-THC (FIG. 18B).

Example 12

Figure 19A:
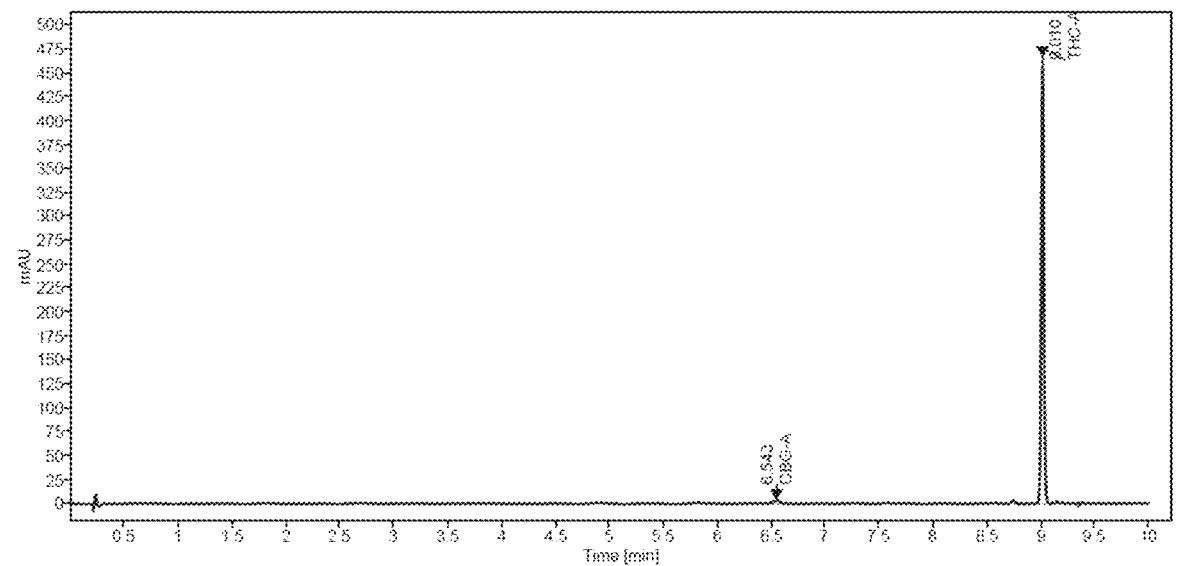
FIG. 19A is an HPLC chromatogram showing the composition of a crude THCA-DMEA salt used in Example 12.

50 mL of a standardized heptane-solubilized *C. sativa* extract containing 131.88 mg/mL THCA, was reacted with a 3:1 molar ratio volume of DMEA (5.80 mL) to produce a crude THCA-DMEA salt precipitate. The crude THCA-DMEA salt was separated from the liquid phase by vacuum filtration, washed with 50 mL of cold heptane (4° C.) followed by a second wash with 100 mL of cold pentane, and dried under vacuum to yield 10.182 g of solid crude THCA-DMEA salt. The crude THCA-DMEA salt was analyzed by HPLC (FIG. 19A).

About 1.0-g samples of the crude THCA-DMEA salt were recrystallized by dissolving in (i) a 1:1 volume/mass ratio of dichloromethane, (ii) a 1.5:1 volume/mass ratio of dichloromethane, or (iii) a 2:1 volume/mass ratio of dicholoromethane (DCM) at room temperature (Table 16). The solubilized THCA-DMEA salts were recrystallized by the addition of (iv) 0.75 mL of heptane at ambient temperature (33% heptane), or (v) 2 mL of heptane (50% heptane). A control sample did not receive any heptane. The samples were mixed thoroughly and then incubated at 4° C. for 10 hours during which time purified THCA-DMEA salts were recrystallized. Each of the recrystallized purified THCA-DMEA salts was then separated from its liquid phase by vacuum filtration, washed with 20 mL of cold heptane (4° C.), dried under vacuum, and analyzed by HPLC.

TABLE 16

| Vol. of DCM solvent (mL) | Vol. of heptane antisolvent (mL) | % antisolvent | Mass of crude THCA-DMEA (g) | Mass of purified THCA-DMEA (g) |
|---|---|---|---|---|
| 1.0 | 0 | 0 | 0.974 | 0.402 |
| 1.5 | 0.75 | 33.3% | 1.021 | 0.271 |
| 2 | 2.0 | 50.0% | 0.974 | 0.389 |

Figure 19B:
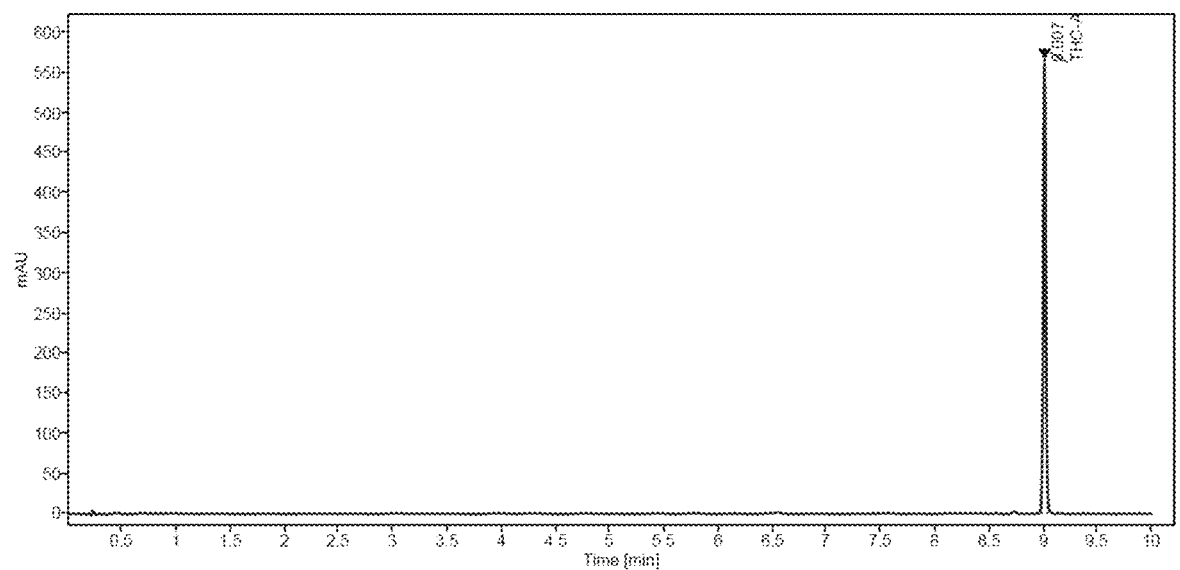
FIG. 19B is an HPLC chromatogram showing the composition of a purified THCA-DMEA salt produced from the crude THCA-DMEA salt shown in FIG. 19A by dissolution in dichloromethane and recrystallization at 4° C.
Figure 19C:
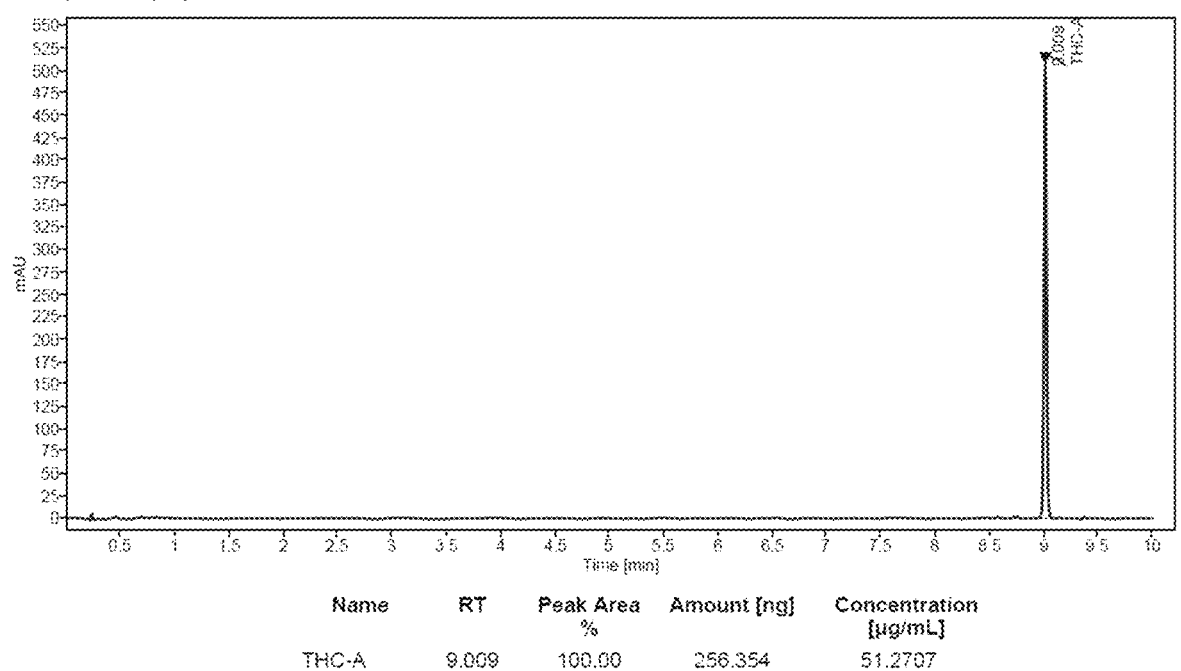
FIG. 19C is an HPLC chromatogram showing the composition of a purified THCA-DMEA salt produced from the crude THCA-DMEA salt shown in FIG. 19A by dissolution in dichloromethane with a spike of 33% heptane and recrystallization at 4° C.
Figure 19D:
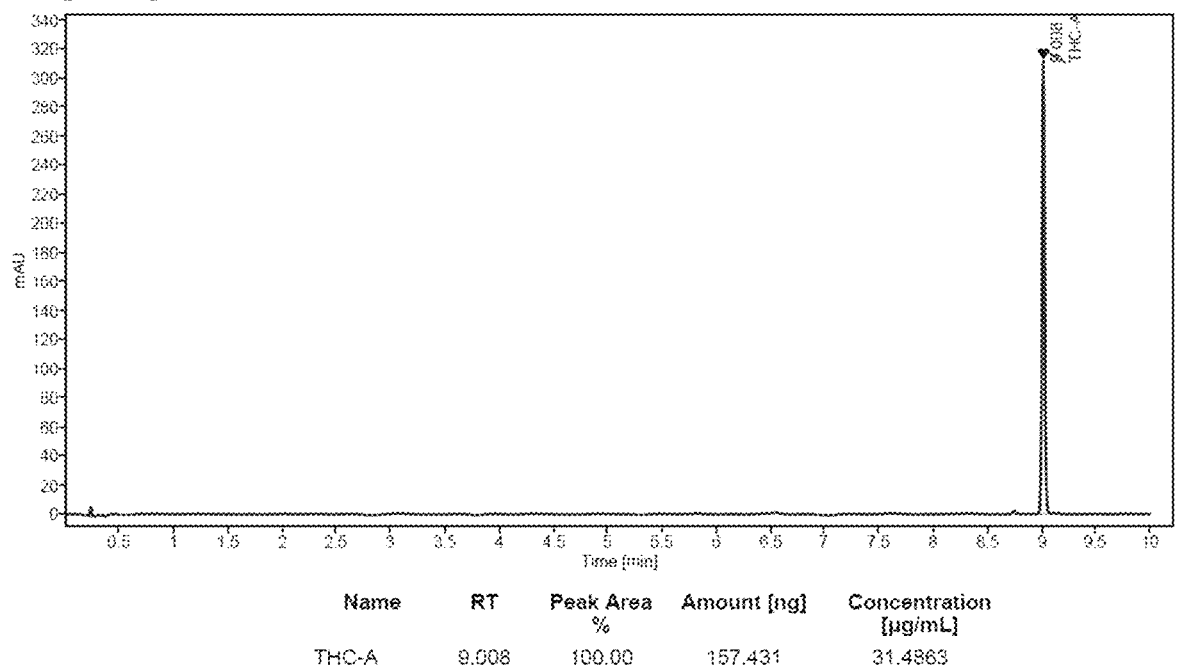
FIG. 19D is an HPLC chromatogram showing the composition of a purified THCA-DMEA salt produced from the crude THCA-DMEA salt shown in FIG. 19A by dissolution in dichloromethane with a spike of 50% heptane and recrystallization at 4° C.

FIG. 19B shows the HPLC analysis of the purified THCA-DMEA salt produced by dissolution in DCM and recrystallization at 4° C. (control). FIG. 19C shows the HPLC analysis of the purified THCA-DMEA salt produced by dissolution in DCM, and recrystallized with a spike of 33% heptane at 4° C. FIG. 19D shows the HPLC analysis of the purified THCA-DMEA salt produced by dissolution in DCM, and recrystallized with a spike of 50% heptane at 4° C.

Example 13

Figure 20:
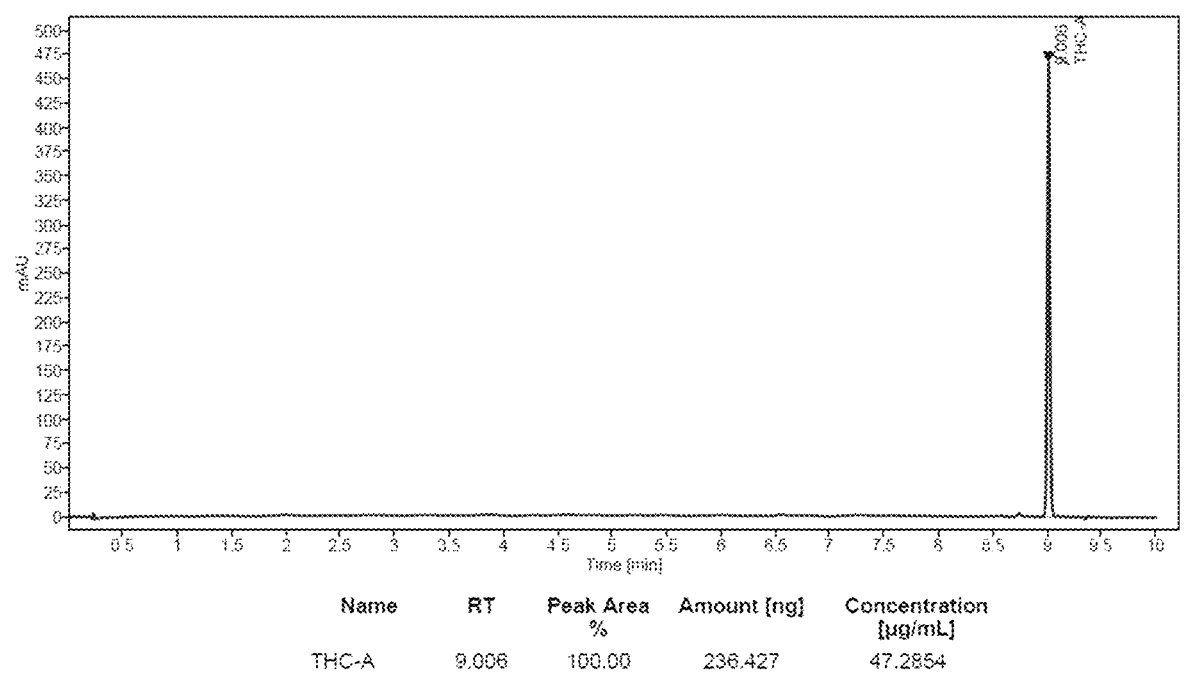
FIG. 20 is an HPLC chromatogram showing the composition of a purified crystalline THCA separated and recovered from the blended purified THCA-DMEA salts produced in Example 12 (FIGS. 19B, 19C, 19D)

This study assessed the production of purified crystalline THCA from the purified THCA-DMEA salts produced in Example 12 (FIGS. 19B-19D). The three masses were blended together and then a 0.775-g portion was dissolved in 4.5 mL of dichloromethane (6:1 volume/mass ratio). The solution was acidified by the addition of 2.6 mL of a 5% HCl solution and thoroughly mixed in a separatory funnel to thereby produce a biphasic solution with the aqueous layer containing the DMEA-hydrochloride and the organic layer containing the THCA. After removal of the aqueous layer, the organic layer was dried over magnesium sulfate, then vacuum filtered. The dichloromethane was removed by distillation thereby producing 0.499 g of crystalline THCA. HPLC analysis confirmed that the THCA was 100% pure (FIG. 20).

Example 14

The crude THCA-DMEA salt prepared and used in Example 12 (FIG. 19A), was also used as the starting point for this study.

About 1-g samples of the crude THCA-DMEA salt were recrystallized by dissolving in (i) a 2:1 volume/mass ratio of a denatured ethanol (dEtOH), (ii) a 3:1 volume/mass of denatured ethanol (2 samples), or (iii) a 4:1 volume/mass of denatured ethanol (3 samples) at about 54° C. with intensive stirring (Table 17).

The dissolved THCA-DMEA salt solutions were cooled to room temperature, after which the THCA-DMEA salts were recrystallized by the addition of, i.e. spiking with (iv) 0.15 mL of distilled $H_2O$ (4.7%), (v) 0.3 mL of distilled $H_2O$ (9.1%), (vi) 0.4 mL of distilled $H_2O$ (12.1%), and (vii) 1.0 mL of distilled $H_2O$ (20.0%). A control sample did not receive a distilled $H_2O$ spike (Table 17). After spiking, the THCA-DMEA solutions were stored at 4° C. for about 10 hr during which time recrystallization of purified THCA-DMEA salts occurred. The recrystallized salts were then separated from their liquid phases, washed with 20 mL of heptane, dried under vacuum, weighed (Table 17), and analyzed by HPLC.

TABLE 17

| Volume of dEtOH solvent (mL) | Volume of $dH_2O$ antisolvent (mL) | % antisolvent | Mass of crude THCA-DMEA (g) | Mass of purified THCA-DMEA (g) |
|---|---|---|---|---|
| 2 | 0 | 0 | 0.985 | 0.770 |
| 3 | 0.15 | 4.7% | 0.976 | 0.684 |
| 3 | 0.30 | 9.1% | 0.992 | 0.604 |
| 4 | 0 | 0 | 0.959 | 0.681 |
| 4 | 0.4 | 9.1% | 0.958 | 0.338 |
| 4 | 1.0 | 20.0% | 1.008 | 0.320 |

Figure 21A:
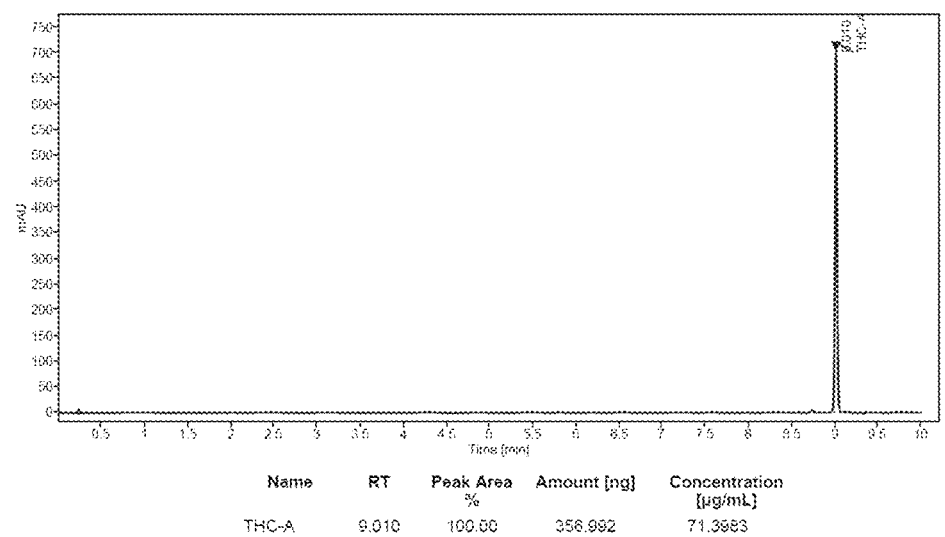
FIG. 21A is an HPLC chromatogram showing the composition of a purified THCA-DMEA salt produced from the crude THCA-DMEA salt shown in FIG. 19A, by dissolution in 2.0 mL of denatured alcohol and recrystallized at 4° C. in Example 13.
Figure 21B:
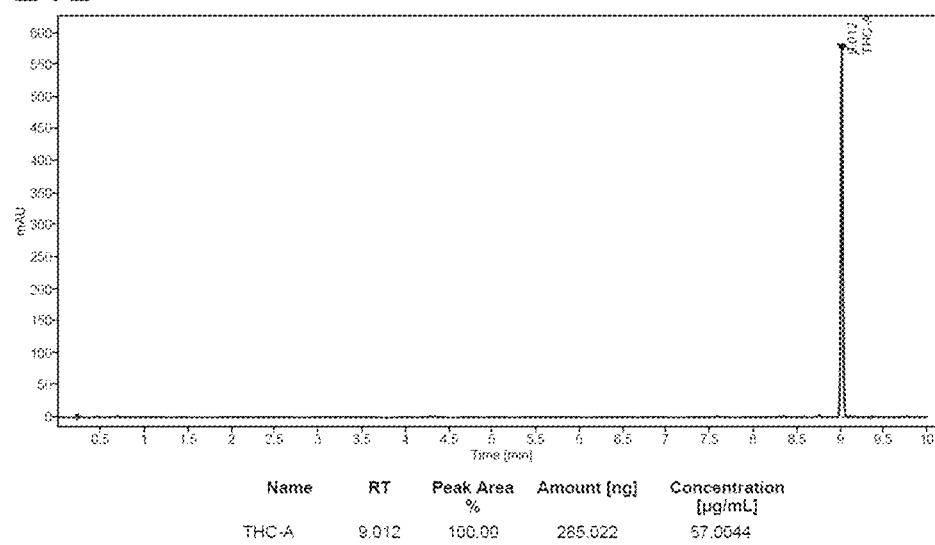
FIG. 21B is an HPLC chromatogram showing the composition of a purified THCA-DMEA salt produced from the crude THCA-DMEA salt shown in FIG. 19A, by dissolution in 3.0 mL of denatured alcohol and recrystallized with a spike of 4.7% of distilled $H_2O$ at 4° C.
Figure 21C:
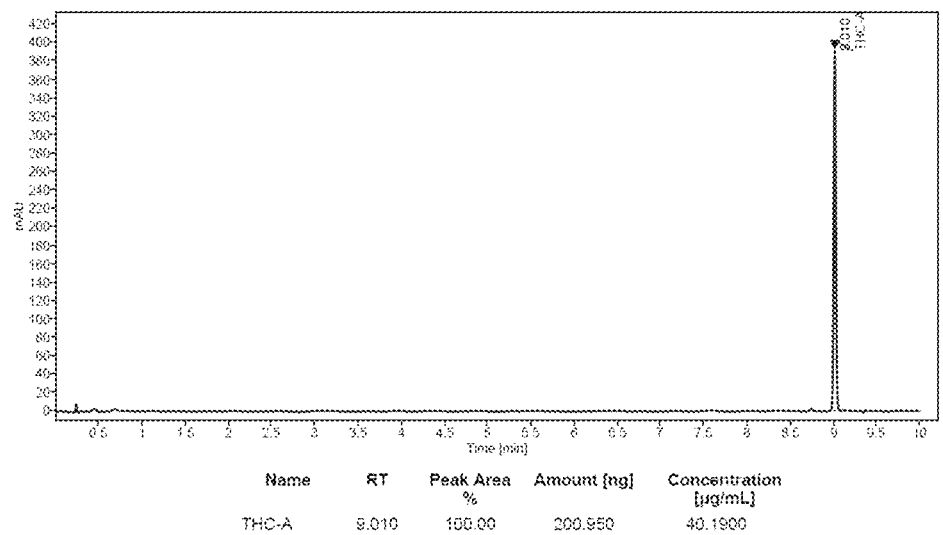
FIG. 21C is an HPLC chromatogram showing the composition of a purified THCA-DMEA salt produced from the crude THCA-DMEA salt shown in FIG. 19A, by dissolution in 3.0 mL of denatured alcohol and recrystallized with a spike of 9.1% of distilled $H_2O$ at 4° C.
Figure 21D:
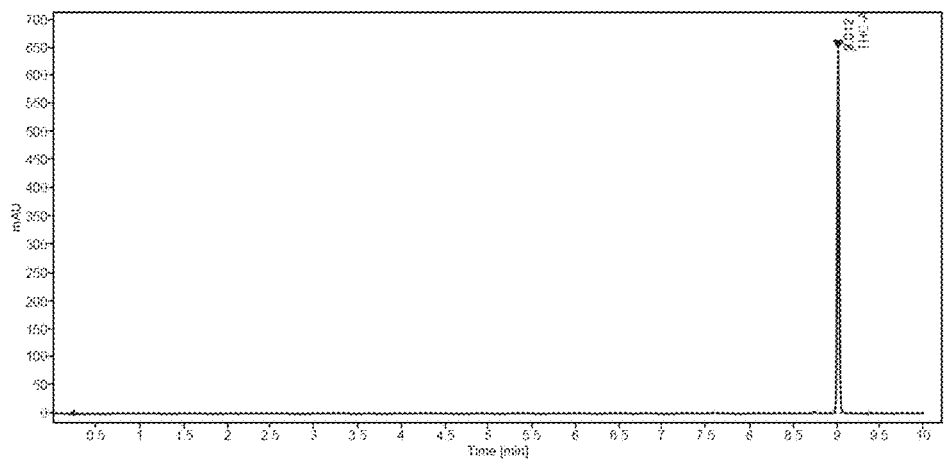
FIG. 21D is an HPLC chromatogram showing the composition of a purified THCA-DMEA salt produced from the crude THCA-DMEA salt shown in FIG. 19A, by dissolution in 3.0 mL of denatured alcohol and at 4° C. (control)
Figure 21E:
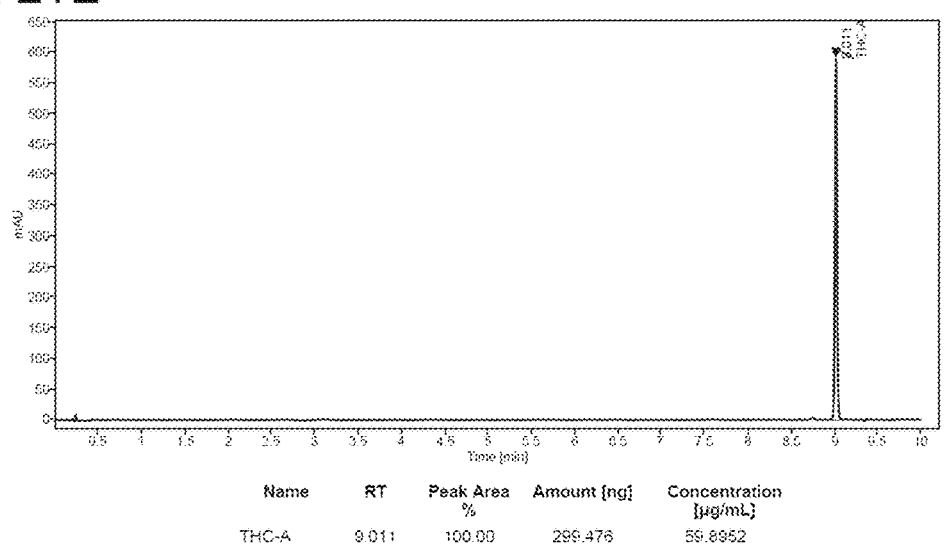
FIG. 21E is an HPLC chromatogram showing the composition of a purified THCA-DMEA salt produced from the crude THCA-DMEA salt shown in FIG. 19A, by dissolution in 3.0 mL of denatured alcohol and recrystallized with a spike of 9.1% of distilled $H_2O$ at 4° C.
Figure 21F:
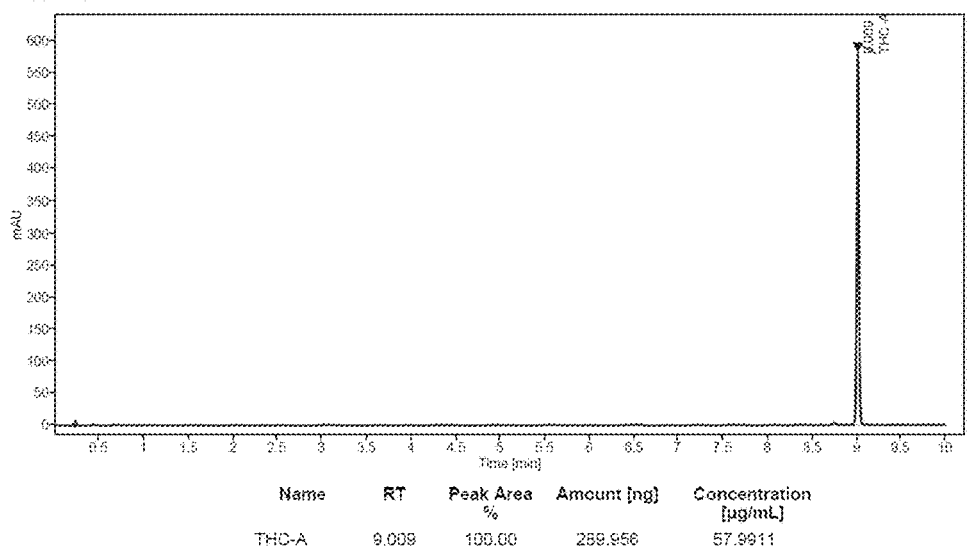
FIG. 21F is an HPLC chromatogram showing the composition of a purified THCA-DMEA salt produced from the crude THCA-DMEA salt shown in FIG. 19A, by dissolution in 3.0 mL of denatured alcohol and recrystallized with a spike of 20.0% of distilled $H_2O$ at 4° C.

FIG. 21A shows the HPLC analysis of the purified THCA-DMEA salt produced by dissolution in 2.0 mL of denatured alcohol and recrystallized at 4° C. (control). FIG. 21B shows the HPLC analysis of the purified THCA-DMEA salt produced by dissolution in 3.0 mL of denatured alcohol, and recrystallized with a spike of 4.7% of distilled $H_2O$ at 4° C. FIG. 21C shows the HPLC analysis of the purified THCA-DMEA salt produced by dissolution in 3.0 mL of denatured alcohol, and recrystallized with a spike of 9.1% of distilled $H_2O$ at 4° C. FIG. 21D shows the HPLC analysis of the purified THCA-DMEA salt produced by dissolution in 4.0 mL of denatured alcohol and recrystallized at 4° C. (control). FIG. 21E shows the HPLC analysis of the purified THCA-DMEA salt produced by dissolution in 4.0 mL of denatured alcohol, and recrystallized with a spike of 9.1% of distilled $H_2O$ at 4° C. FIG. 21F shows the HPLC analysis of the purified THCA-DMEA salt produced by dissolution in 4.0 mL of denatured alcohol, and recrystallized with a spike of 20.0% of distilled $H_2O$ at 4° C.

These data indicated that highly purified THCA-DMEA salt may be produced by dissolving crude THCA-DMEA salt in smaller volumes of denatured alcohol with or without a spike of distilled water.

Example 15

This study assessed recovery of a purified crystalline THCA from a purified THCA-DMEA salt that was produced by dissolution in warmed denatured ethanol, and then recrystallized by cooling and spiking with distilled water.

Figure 22:
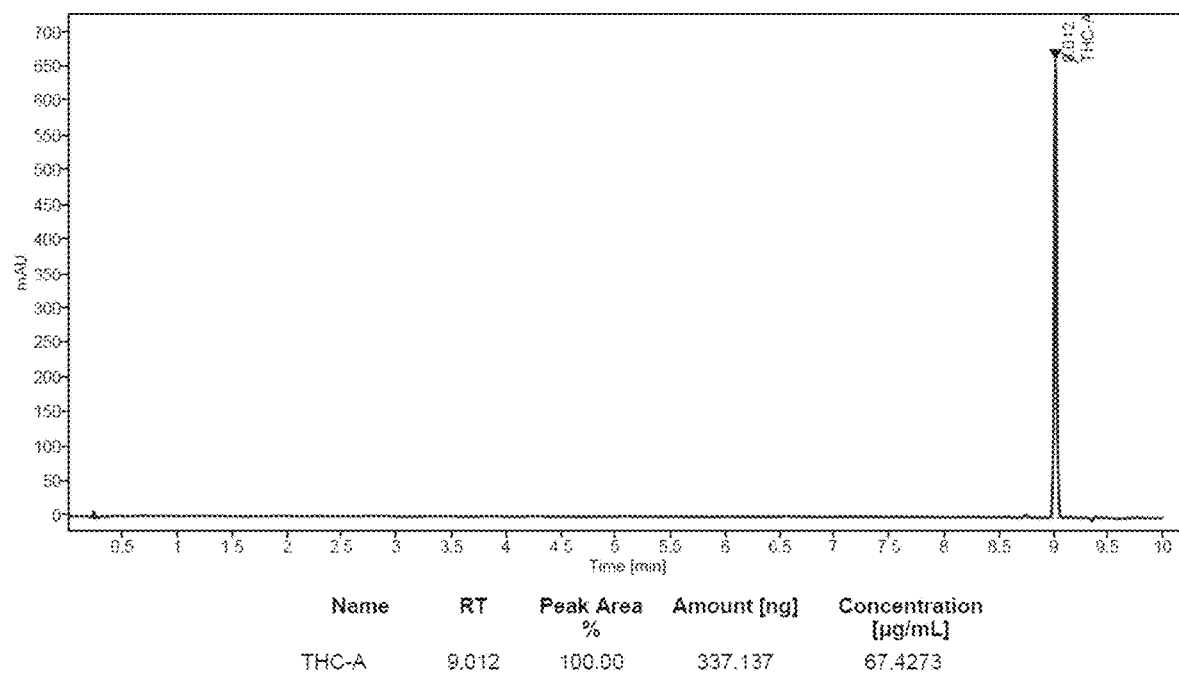
FIG. 22 is an HPLC chromatogram showing the composition of a purified crystalline THCA separated and recovered from the blended purified THCA-DMEA salts produced in Example 12 (FIGS. 19B, 19C, 19D)

The purified THCA-DMEA salts produced in Example 14 (FIGS. 21A-21F) were blended together after which, a 2.411-g sample was dissolved in 15 mL of dichloromethane (6:1 volume/mass ratio). The solution was acidified with 8 mL of a 5% HCl solution and thoroughly mixed by shaking in a separatory funnel. The aqueous layer containing the DMEA-hydrochloride was separated from the organic layer containing the THCA. The organic layer was dried over magnesium sulfate, vacuum filtered and the dichloromethane was removed by distillation, producing 1.7958 grams of crystalline THCA (FIG. 22).

The invention claimed is:

1. A method for separating, recovering, and purifying tetrahydrocannabinolic acid (THCA) from an organic solvent solution comprising a mixture of cannabinoids, said method comprising:
   providing an organic solvent solution containing therein a complex mixture of cannabinoids;
   assaying the organic solvent solution to determine a first concentration of THCA therein;
      adding to the organic solvent solution a volume of a first organic solvent selected from pentane, hexane, and heptane, and commingling therewith to adjust the first THC A concentration to a target concentration value selected from a range of target concentrations, thereby producing a solvent-solubilized solution;
   adding a selected amine to the solvent-solubilized solution and commingling therewith to precipitate therefrom a THCA-amine salt, wherein said amine is:
      a diamine selected from one of 1,8-diazabicyclo[5.4.0]undec-7-ene (DBU), 1,5-diazabicyclo[4.3.0]non-5-ene (DBN), 1,4-diazabicyclo[2.2.2]octane (DABCO), and tetramethylethylenediamine (TMEDA), or
      an amino alcohol selected from one of dimethylethanolamine (DMEA), and piperidineethanol, or
      a tertiary amine selected from one of triethylamine, ethyldiisopropylamine (Hunig's base), and quinine, or
      dicyclohexylamine;
   washing the precipitated THCA-amine salt at least once with said first selected organic solvent and then drying the washed THCA-amine salt;
   dissolving the THCA-amine salt in a selected second organic solvent and commingling therewith;
   adding a volume of a selected antisolvent to the dissolved THCA-amine salt and commingling therewith to thereby recrystallize the THCA-amine salt therefrom; and
   washing the recrystallized THCA-amine salt at least once with said selected antisolvent to produce a purified THCA-amine salt, and then drying the purified THCA-amine salt.

2. The method according to claim 1, additionally comprising the steps of:
   decarboxylating the purified THCA-amine salt to produce an oil comprising 49-tetrahydrocannabinol (49-THC) and amine;
   solubilizing the oil comprising $\Delta^9$-THC in a selected third organic solvent to thereby partition therefrom an organic layer containing a highly purified $\Delta^9$-THC oil and the amine, and an aqueous layer;
   separating the aqueous layer from the organic layer containing the highly purified $\Delta^9$-THC and the amine;
   acidifying the organic layer with a mineral acid to partition therefrom an organic layer containing highly purified $\Delta^9$-THC in the form of an oil, and an aqueous layer containing the amine;
   separating the aqueous layer from the highly purified $\Delta^9$-THC oil; and
   concentrating the highly purified $\Delta^9$-THC oil by volatilization of the third organic solvent therefrom.

3. The method according to claim 1, wherein the organic solvent solution comprising the mixture of cannabinoids was prepared by:
   processing a *Cannabis sativa* biomass with a solvent to produce a solvent extract of cannabinoids therefrom,
   concentrating the *C. sativa* extract by removing the solvent therefrom, and
   solubilizing the *C. sativa* extract in the first organic solvent.

4. The method according to claim 1, wherein a selected volume of a denatured ethanol or acetone is added to and commingled with the solvent-solubilized solution prior to the addition of the selected amine.

5. The method according to claim 1, wherein the second organic solvent is one of ethyl acetate, methanol, ethanol, dichloromethane, and toluene.

6. The method according to claim 1, wherein the antisolvent is an alkane selected from pentane, hexane, heptane, petroleum ethers, and water.

7. The method according to claim 2, wherein decarboxylation of the purified THCA-amine salt comprises dissolution of the purified THCA-amine salt in a selected volume of a sodium carbonate solution and then heating the sodium carbonate solution at about 100° C. under constant mixing to thereby produce therein a mixture of $\Delta 9$-THC and the amine.

8. The method according to claim 7, wherein the sodium carbonate solution has a concentration selected from a range of 1% to 15% (w/v).

9. The method according to claim 2, wherein the third organic solvent is one of pentane, hexane, heptane, a low b.p. petroleum ether, and dichloromethane.

10. The method according to claim 2, wherein the mineral acid is HCl.

11. The method according to claim 1, additionally comprising the steps of:
   re-solubilizing the purified THCA-amine salt in the second selected organic solvent;
   acidifying the solubilized purified THCA-amine salt with a mineral acid to partition therefrom an organic layer containing a highly purified THCA in the form of an oil, and an aqueous layer containing the amine;
   separating the aqueous layer from the organic layer containing the highly purified THCA; and
   removing the second selected organic solvent to thereby produce a highly purified THCA powder.

12. A method for separating, recovering, and purifying a tetrahydrocannabinolic acid-amine salt (THCA-amine salt) from an organic solvent solution comprising a mixture of cannabinoids, said method comprising:
   providing an organic solvent solution containing therein a complex mixture of cannabinoids;
   assaying the organic solvent solution to determine a first concentration of THCA therein;
   adding a volume of an alkane solvent selected from pentane, hexane, heptane, and a low b.p. petroleum ether to the organic solvent solution and commingling therewith to adjust the first THCA concentration to a target concentration value selected from a range of target concentrations, thereby producing a solvent-solubilized solution;

adding an amine to the solvent-solubilized solution and commingling therewith to precipitate therefrom a THCA-amine salt, wherein said amine is selected from a group consisting of 1,8-diazabicyclo[5.4.0]undec-7-ene (DBU), 1,5-diazabicyclo[4.3.0]non-5-ene (DBN), 1,4-diazabicyclo[2.2.2]octane (DABCO), dimethylethanolamine (DMEA), piperidineethanol, dicyclohexylamine, triethylamine, ethyldiisopropylamime (Hunig's base), tetramethylethylenediamine (TMEDA), and quinine;

separating the precipitated THCA-amine salt solvent-solubilized solution;

washing the recovered THCA-amine salt at least once with said selected alkane solvent; and drying the washed THCA-amine salt to produce the THCA-amine salt.

13. The method according to claim 12, wherein a selected volume of denatured ethanol is added to and commingled with the solvent-solubilized solution prior to the addition of the selected amine.

14. The method according to claim 12, wherein the amine is DBU and the salt produced is a THCA-DBU salt.

15. The method according to claim 12, wherein the amine is DBN and the salt produced is a THCA-DBN salt.

16. The method according to claim 12, wherein the amine is DABCO and the salt produced is a THCA-DABCO salt.

17. The method according to claim 12, wherein the amine is DMEA and the salt produced is a THCA-DMEA salt.

18. The method according to claim 12, wherein the amine is piperidineethanol and the salt produced is a THCA-piperidineethanol salt.

19. The method according to claim 12, wherein the amine is dicyclohexylamine and the salt produced is a THCA-dicyclohexylamine salt.

20. The method according to claim 12, wherein the amine is triethylamine and the salt produced is a THCA-triethylamine salt.

21. The method according to claim 12, wherein the amine is Hunig's base and the salt produced is a THCA-Hunig's base salt.

22. The method according to claim 12, wherein the amine is TMEDA and the salt produced is a THCA-TMEDA salt.

23. The method according to claim 12, wherein the amine is quinine and the salt produced is a THCA-quinine salt.

24. A tetrahydrocannabinolic acid-amine salt having a chemical structure (4)

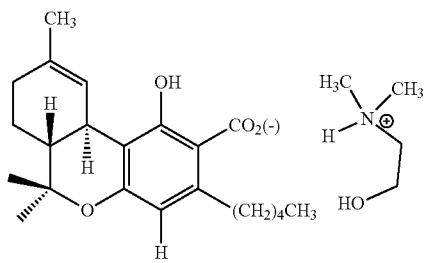

(THCA-dimethylethanolamine salt).

25. A tetrahydrocannabinolic acid-amine salt having a chemical structure (5)

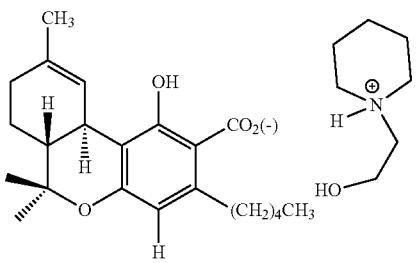

(THCA-piperidineethanol salt).

26. A tetrahydrocannabinolic acid-amine salt having a chemical structure (6)

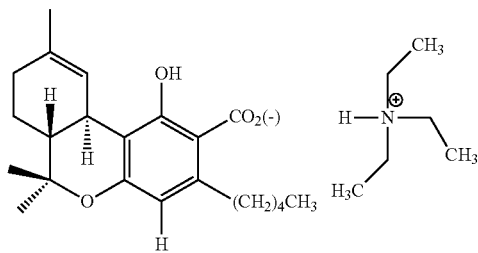

(THCA-triethylamine salt).

27. A tetrahydrocannabinolic acid-amine salt having a chemical structure (7)

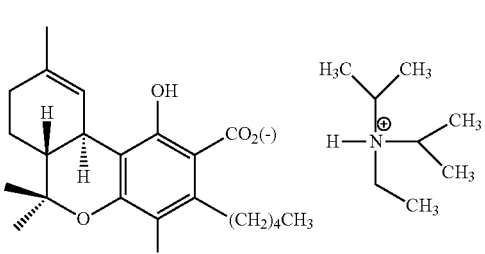

(THCA-N-ethyldiisiopropylamine salt).

28. A tetrahydrocannabinolic acid-amine salt having a chemical structure (8)

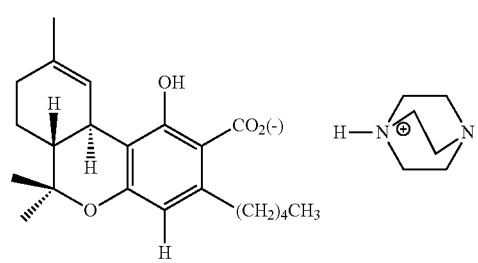

(THCA-1,4-diazobicylcooctane salt).

29. A tetrahydrocannabinolic acid-amine salt having a chemical structure (9)

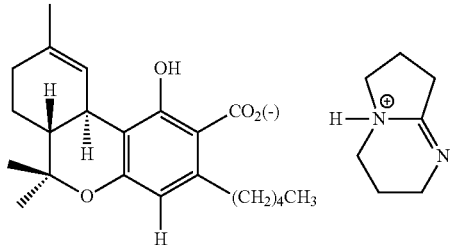

(THCA-1,5-diazabicylco[4.3.0]non-5-ene salt).

30. A tetrahydrocannabinolic acid-amine salt having a chemical structure (10)

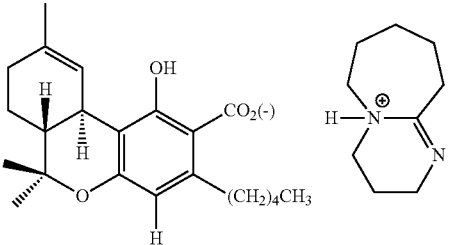

(THCA-1,8-diazabicyclo[5.4.0]undec-7-ene salt).

31. A tetrahydrocannabinolic acid-amine salt having a chemical structure (11)

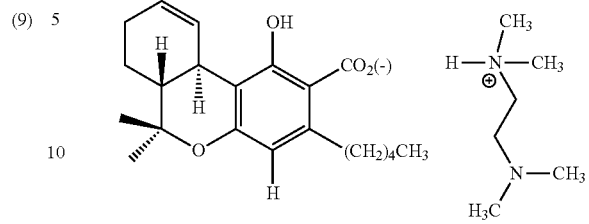

(THCA-tetramethylethylenediamine salt).

32. A tetrahydrocannabinolic acid-amine salt having a chemical structure (12)

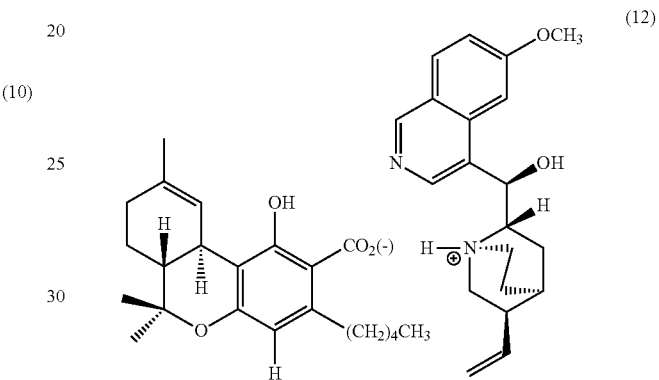

(THCA-quinine salt).

* * * * *